(12) United States Patent
Zurawski et al.

(10) Patent No.: US 7,786,267 B2
(45) Date of Patent: *Aug. 31, 2010

(54) MULTIVARIABLE ANTIGENS COMPLEXED WITH TARGETING HUMANIZED MONOCLONAL ANTIBODY

(75) Inventors: Gerard Zurawski, Midlothian, TX (US); Anne-Laure Flamar, Dallas, TX (US); Eynav Klechevsky, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/024,036

(22) Filed: Jan. 31, 2008

(65) Prior Publication Data

US 2008/0254044 A1 Oct. 16, 2008

Related U.S. Application Data

(60) Provisional application No. 60/888,029, filed on Feb. 2, 2007.

(51) Int. Cl.
*C07K 16/46* (2006.01)
*C07K 17/02* (2006.01)
*C07K 16/28* (2006.01)
*A61K 39/44* (2006.01)

(52) U.S. Cl. ............ 530/387.1; 530/387.3; 530/388.22; 530/350; 424/134.1; 424/143.1; 424/178.1; 424/181.1; 424/193.1

(58) Field of Classification Search ........................ None
See application file for complete search history.

(56) References Cited

U.S. PATENT DOCUMENTS

| | | | |
|---|---|---|---|
| 3,791,932 A | 2/1974 | Schuurs, et al. | |
| 3,949,064 A | 4/1976 | Bornstein et al. | |
| 4,174,384 A | 11/1979 | Ullman et al. | |
| 4,554,101 A | 11/1985 | Hopp | |
| 6,410,241 B1 | 6/2002 | Sykes et al. | |
| 6,541,011 B2 | 4/2003 | Punnonen et al. | |
| 2004/0265901 A1* | 12/2004 | Li | 435/7.1 |
| 2005/0064509 A1* | 3/2005 | Bradbury et al. | 435/7.1 |
| 2005/0106700 A1* | 5/2005 | Nomura et al. | 435/226 |

FOREIGN PATENT DOCUMENTS

| | | | |
|---|---|---|---|
| WO | 97/14789 A2 | | 4/1997 |
| WO | WO 00/63251 | * | 10/2000 |

OTHER PUBLICATIONS

Ding et al, J Bacteriology 182(17): 4915-1925, Sep. 2000.*
Kobrin et al, J Immunology 146: 2017-2020, 1991.*
Barrios et al, J Molecular Recognition 17: 332-338, 2004.*
Zhu et al, Investigational New Drugs 17: 195-212, 1999.*
Ding et al, Genetic Engineering 25: 209-225, 2003.*
Craig, et al., "Engineered Proteins Contain8ing the Cohesin and Dockerin Domains From Clostridium Thermocelium Provides a Reversible, High Affinity Interaction for Biotechnology Applications," J Biotechnology (2006), 121:165-173.
Carvalho, A. L, et al., "Cellulosome assembly revealed by the crystal structure of the cohesin—dockerin complex," PNAS (2003), 100:13809-13814.
Fierobe, H-P, et al., "Design and Production of Active Cellulosome Chimeras," J Biol Chem (2001), 276:21257-21261.
Frankel, A. F., "Increased Sophistication of Immunotoxins," Clin Can Res (2002), 8:942-944.
Starovasnik, M. A., et al., Structural mimicry of a native protein by a minimized binding domain, PNAS (1997), 94:10080-10085.

* cited by examiner

*Primary Examiner*—Phuong Huynh
(74) *Attorney, Agent, or Firm*—Edwin S. Flores; Daniel J. Chalker; Chalker Flores, LLP

(57) ABSTRACT

The present invention includes compositions and methods for designing, making and using modular recombinant antibodies or fragments thereof with one half of a cohesin-dockerin pair that permits the rapid assembly of multivariant antigen conjugates.

10 Claims, 15 Drawing Sheets

Single Targeting mAb-Antigen Fusion Proteins

Multivariable Targeting mAb-Antigen Complexes

Lane 1: mIgG2b~1 ug
Lane 2: anti-DCIR_2C9.doc 15 uL
Lane 3: anti-ASGPR_49C11.doc 15 uL
Lane 4: anti-DCSIGN/L_16E7.doc 15 uL
Lane 5: anti-LOXI_15C4.PSA 15 uL 1: Cohesin-hgp100-PeptideA
2: Cohesin-hMART-1-PeptideB
3: Cohesin-Flex-hMART-1-PeptideA

MULTIVARIABLE ANTIGENS COMPLEXED WITH TARGETING HUMANIZED MONOCLONAL ANTIBODY

CROSS-REFERENCE TO RELATED APPLICATIONS

This application claims priority to U.S. Provisional Application Ser. No. 60/888,029, filed Feb. 2, 2007, the contents of which is incorporated by reference herein in its entirety.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of novel vaccines, and more particularly, to the design, manufacture and use of multivariable antigens complexed with targeting humanized monoclonal antibodies.

BACKGROUND OF THE INVENTION

Without limiting the scope of the invention, its background is described in connection with vaccine development.

Protein engineering technology relating to monoclonal antibodies is highly advanced regarding humanization (i.e., rendering e.g., a rodent mAb sequence into a human mAb sequence while preserving specific antigen combining sites of the original mAb) and production (typically secreted from mammalian cell lines). In research and development are new applications of rAbs related to vaccination and are presently based on engineered rAb-antigen fusion proteins (typically with the antigen coding region placed in-frame with the C-terminal codon of the rAb heavy or H chain). A roadblock to this technology is the successful expression and production of fully functional rAb-antigen. In many, perhaps most, cases the desired antigen confounds secretion of the engineered rAb-antigen. Also, the likelihood of poor or null expression is increased if the desired entity includes multiple antigen coding regions.

SUMMARY OF THE INVENTION

The invention provides methods for the assembly of rAb antigen complexes in a controlled manner by simple mixing components and accommodates the ability to express and produce the rAb and antigen(s) in different expression—production systems that are best suited to the individual rAb and particular antigen. In addition, the invention demonstrates the novel application of the high affinity and high specificity cohesin-dockerin interaction to secreted mammalian expression systems, thus permitting the development of unique protein engineering formats and production of new protein tools for research and clinical application.

More particularly, the present invention uses the cohesin-dockerin protein domains and their surrounding linker. For example, the invention permits the controlled assembly of recombinant monoclonal antibodies (rAbs) complexed to antigens, toxins, or cellular activating agents. The invention has wide potential application in vaccination and cancer therapy. Also claimed are derivatives of this technology that permit the production of novel proteins with specific affinities for other proteins.

The invention is based on particular components of the well studied bacterial cellulose degrading protein complex called the cellulosome. Specifically, two protein domains (cohesin and dockerin) and natural protein linker sequences are utilized via the invention in novel contexts and applications.

The present invention is based on the discovery that particular cohesin and dockerin domains can be successfully and efficiently secreted from mammalian cells as fusion proteins while maintaining the specific and high affinity cohesin-dockerin protein-protein interaction. While the extensive cohesin-dockerin literature teaches the expectation that such fusion proteins should have this functionality, it does not describe production of such fusion proteins in mammalian secretion systems. The state of scientific knowledge does not allow the prediction of the discovery since the rules (other than features such as signal peptide) for successful secretion are not fully established. Furthermore, the cohesin linker regions are known to be glycosylated in their native bacteria, and the cohesin and dockerin domains contain predicted glycosylation sites. While this may actually favor secretion from mammalian cells, it is unclear if 'unnatural' glyosylation will perturb the cohesis-dockerin interaction.

While cohesin-dockerin interaction for various commercial applications has been published, the present invention is based on a previously unrealized potential for this interaction built around assembling specific protein complexes unrelated to the controlled assembly enzyme applications.

The invention includes the use of all cohesin-dockerin sequences from diverse cellulose degrading microbes, but describes the application of specific cohesin and dockerin and linker sequences from the microbe *Clostridium thermocellum*. For example, the sequence described herein encodes the H chain of a human IgG4 linked at the C-terminal codon to a *Clostridium thermocellum* dockerin sequence (called rAb-.doc). Other embodiments of rAb.doc proteins are described similarly with examples that are engineered by simply transferring the dockerin coding region as a DNA fragment to vectors encoding the different H chain entities.

More particularly, the present invention includes a modular rAb carrier that includes an antigen-specific binding domain linked to one or more antigen carrier domains and one half of a cohesin-dockerin binding pair. The antigen-specific binding domain may be at least a portion of an antibody and the antibody is a fusion protein with and the binding pair in a fusion protein with one half of a cohesin-dockerin binding pair. The rAb may also include a complementary half of the cohesin-dockerin binding pair bound to an antigen that forms a complex with the modular rAb carrier. The complementary half of the cohesin-dockerin binding pair may itself be a fusion protein with the antigen carried as part of the complex (modular rAb carrier (cohesin/dockerin) antigen complex). Examples of antigen specific domain include a full length antibody, an antibody variable region domain, an Fab fragment, a Fab' fragment, an $F(ab)_2$ fragment, and Fv fragment, and Fabc fragment and/or a Fab fragment with portions of the Fc domain. Non limiting examples of sources for the cohesin-dockerin binding pair include *Clostridium thermocellum, Clostridium josui, Clostridium cellulolyticum* and *Bacteroides* cellulosolvens and combinations thereof.

Non-limiting examples for targeting by the antigen-specific binding domain include: cell surface marker selected from MHC class I, MHC class II, CD1, CD2, CD3, CD4, CD8, CD11b, CD14, CD15, CD16, CD 19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor or other receptor relatively specifically expressed by antigen presenting cells.

The rAb of the present invention may also includes combinations of the domains that are defined as: an rAb.Doc; an rAb.Coh; an rAb.(Coh)$_x$; an rAb.(Doc)$_x$; an rAb.(Coh.Doc)$_x$; or an rAb.(Coh)$_x$(Doc)$_x$; wherein x is 1, 2, 3, 4, 5, 6, 7, 8, 9, 10 or more. Examples of the modular rAb carrier in a complex include:

an rAb.Doc:Coh.antigen;
an rAb.Coh:Doc.antigen;
an rAb.(Coh)$_x$:(Doc.antigen)$_x$;
an rAb.(Doc)$_x$:(Coh.antigen)$_x$;
an rAb.(Coh.Doc)$_x$:(Doc.antigen$^1$)(Coh.antigen$^2$); or
an rAb.(Coh)$_x$(Doc)$_x$:(Doc.antigen$^1$)$_x$(Coh.antigen$^2$)$_x$;

wherein x is 1, 2, 3, 4, 5, 6, 7, 8, 9 or 10.

The present invention also include a vaccine of a modular rAb carrier that includes an antigen specific domain linked to one or more domains comprising one half of the cohesin-dockerin binding pair bound to a complementary half of the cohesin-dockerin binding pair bound to an antigen. Non-limiting examples for targeting the rAb include immune cell surface protein selected from MHC class I, MHC class II, CD1, CD2, CD3, CD4, CD8, CD11b, CD14, CD15, CD16, CD 19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor or other receptor relatively specifically expressed by antigen presenting cells. Targets for vaccination with the rAb antigen carrier include, e.g., a bacterial, viral, fungal, protozoan or cancer protein and fragments thereof. The vaccine wherein the modular rAb carrier is further defined: an rAb.Doc:Coh.antigen; an rAb.Coh:Doc.antigen; an rAb.(Coh)$_x$:(Doc.antigen)$_x$; an rAb.(Doc)$_x$:(Coh.antigen)$_x$; an rAb.(Coh.Doc)$_x$:(Doc.antigen$^1$)(Coh.antigen$^2$); or an rAb.(Coh)$_x$(Doc)$_x$:(Doc.antigen$^1$)$_x$(Coh.antigen$^2$)$_x$; wherein x is 1, 2, 3, 4, 5, 6, 7, 8, 9 or 10.

The present invention also includes an isolated nucleic acid comprising a coding segment for a target-specific domain and one or more domains and one half of a cohesin-dockerin binding pair. For example, the target may be an antigen and the target specific domain may encode at least a portion of an antibody. The one or more domains can encode one or more cohesin domains, one or more dockerin domains or a combination of one or more cohesin and dockerin domains. The rAb is further defined as: an rAb.Doc; an rAb.Coh; an rAb.(Coh)$_x$; an rAb.(Doc)$_x$; an rAb.(Coh.Doc)$_x$; or an rAb.(Coh)$_x$(Doc)$_x$; wherein x is 1, 2, 3, 4, 5, 6, 7, 8, 9 or 10.

The present invention also includes a vector that includes a nucleic acid encoding an antigen specific domain and one or more domains that comprise one half of a cohesin-dockerin binding pair, a one half of a cohesin-dockerin binding pair with a protein molecule to be carried and combinations thereof. The one half of a cohesin-dockerin binding pair, a one half of a cohesin-dockerin binding pair with a protein molecule to be carried and combinations thereof are under the control of the same promoter, different promoters, transcribed in-line, transcribed in opposite directions.

The present invention also includes a host cell comprising a vector comprising a nucleic acid encoding an antigen specific domain and one or more domains and one half of a cohesin-dockerin binding pair.

A method of making a modular rAb carrier by combining an antigen specific domain linked to one or more domains of one half of a cohesin-dockerin binding pair. The rAb is further defined as: an rAb.Doc; an rAb.Coh; an rAb.(Coh)$_x$; an rAb.(Doc)$_x$; an rAb.(Coh.Doc)$_x$; or an rAb.(Coh)$_x$(Doc)$_x$; wherein x is 1, 2, 3, 4, 5, 6, 7, 8, 9 or 10. Examples of the rAb is complexed with a complementary half of a cohesion:dokerin pair bound to an antigen and is selected from: an rAb.Doc:Coh.antigen; an rAb.Coh:Doc.antigen; an rAb.(Coh)$_x$:(Doc.antigen)$_x$; an rAb.(Doc)$_x$:(Coh.antigen)$_x$; an rAb.(Coh.Doc)$_x$:(Doc.antigen$^1$)(Coh.antigen$^2$); or an rAb.(Coh)$_x$(Doc)$_x$:(Doc.antigen$^1$)$_x$(Coh.antigen$^2$)$_x$; wherein x is 1, 2, 3, 4, 5, 6, 7, 8, 9 or 10.

The present invention may also be an immunotoxin that includes an rAb.Doc:Coh.toxin self-assembled conjugate, wherein the rAb is specific for a cell target. Examples of toxins include a radioactive isotope, metal, enzyme, botulin, tetanus, ricin, cholera, diphtheria, aflatoxins, perfringens toxin, mycotoxins, shigatoxin, staphylococcal enterotoxin B, T2, seguitoxin, saxitoxin, abrin, cyanoginosin, alphatoxin, tetrodotoxin, aconotoxin, snake venom and spider venom. Cell targets for the immunotoxin include diseased or infected cells. Examples of diseased cells for targeting include cancer cell for, e.g., hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. The immunotoxin may target pathogens directly, e.g., bacteria, a protozoan, a helminth, a virally-infected cell or a fungus.

The present invention also includes a method for protein purification by separating a cohesin or dockerin fusion protein by interacting the fusion protein with a rAb that is conjugated to the complementary cohesin or dockerin bound to a substrate. The present invention may also use the cohesin as a fusion partner for toxins for conferring beneficial biochemical properties favoring ready purification of active cohesin-.toxin fusion protein. The present invention may also use the anti-DC rAb.Doc to target DC for therapeutic applications where ablating DC. Therapeutic applications include, e.g., transplantation, autoimmune disease, infectious disease or cancer. The invention also includes an anti-DC-SIGN/L antibody provided in an amount that is sufficient to enhance the survival of dendritic cells, wherein the antibody matures and activates the dendritic cells for immunization. The antibody may target cells in vivo, e.g., dendritic cells as an adjuvant in vaccines.

Also invented is a bivalent and multivalent ($rAb^1$.Doc:Coh.$rAb^2$) self-assembled conjugates as therapeutic, diagnostic, and industrial agents. Alternatively, the invention is a bivalent and multivalent (rAb.Doc:Coh.cytokine), (rAb.Coh:Doc.cytokine) or ($cytokine^1$.Coh:$cytokine^2$ Doc) self-assembled conjugates as therapeutic, cell proliferation or maturing agents. The modular rAbs carrier may be made by method that includes screening one or more multivalent rAb and/or rAb.cytokine and/or cytokine.cytokine combinations that are capable of specifically binding to a target cell and delivering the cytokine such that it exerts its effect on the target cell. Cytokines for use with the present invention include: interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors, B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF, transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

BRIEF DESCRIPTION OF THE DRAWINGS

For a more complete understanding of the features and advantages of the present invention, reference is now made to the detailed description of the invention along with the accompanying figures and in which:

FIG. 1 compares the prior art (top portion) with an example of the multiple antigens targeted in a complex simultaneously with the same engineered humanized mAb (MATCHMAB) (bottom portion).

FIG. 2 shows the use of the present invention to form Bi-specific mAbs.

DETAILED DESCRIPTION OF THE INVENTION

Figure 3:
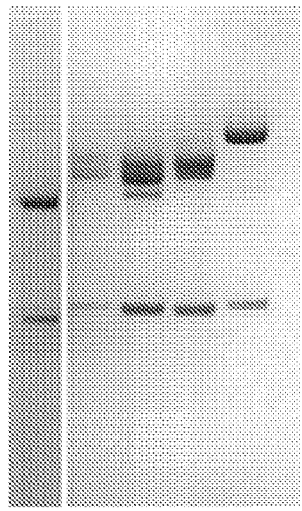
FIG. 3 shows Protein G affinity purified secreted rAb proteins analyzed by reducing SDS.PAGE and Coomassie Brilliant Blue staining. Lanes are from left to right.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

At present, protein engineering technology enables the ready and controlled addition of an antigen (or different antigens to one of the chains) of a recombinant mAb (H or L, usually the C-terminus of H is often used). If different antigens or different antigen sets need to be linked to the mAb, then the mAb needs to be re-engineered, expressed, and purified as a different entity.

The present invention provides for the complexing of multiple antigens or proteins (engineered, expressed, and purified independently from the primary mAb) in a controlled, multivariable fashion, to one single primary recombinant mAb.

Presently, there are methods for engineering site-specific biotinylation sites that provide for the addition of different proteins (each engineered separately linked to streptavidin) to the one primary mAb. However, the present invention provides for addition to the primary mAb of multiple combinations, in fixed equimolar ratios and locations, of separately engineered proteins.

As used herein, the term "modular rAb carrier" is used to describe a recombinant antibody system that has been engineered to provide the controlled modular addition of diverse antigens, activating proteins, or other antibodies to a single recombinant monoclonal antibody (mAb). The rAb may be a monoclonal antibody made using standard hybridoma techniques, recombinant antibody display, humanized monoclonal antibodies and the like. The modular rAb carrier can be used to, e.g., target (via one primary recombinant antibody against an internalizing receptor, e.g., a human dendritic cell receptor) multiple antigens and/or antigens and an activating cytokine to dendritic cells (DC). The modular rAb carrier may also be used to join two different recombinant mAbs end-to-end in a controlled and defined manner.

The antigen binding portion of the "modular rAb carrier" may be one or more variable domains, one or more variable and the first constant domain, an Fab fragment, a Fab' fragment, an $F(ab)_2$ fragment, and Fv fragment, and Fabc fragment and/or a Fab fragment with portions of the Fc domain to which the cognate modular binding portions are added to the amino acid sequence and/or bound. The antibody for use in the modular rAb carrier can be of any isotype or class, subclass or from any source (animal and/or recombinant).

In one non-limiting example, the modular rAb carrier is engineered to have one or more modular cohesin-dockerin protein domains for making specific and defined protein complexes in the context of engineered recombinant mAbs. The mAb is a portion of a fusion protein that includes one or more modular cohesin-dockerin protein domains carboxy from the antigen binding domains of the mAb. The cohesin-dockerin protein domains may even be attached post-translationally, e.g., by using chemical cross-linkers and/or disulfide bonding.

The modular rAb carrier will be used to carry a separate molecule, e.g., a peptide, protein, lipid, carbohydrate, nucleic acid (oligonucleotide, aptamer, vector with or without base or backbone modifications) or combinations thereof by binding that separate molecule to the complementary half of the cohesion:dockerin pair. For example, either the dockerin or cohesin made be made into a fusion protein or chemically bound to an antigen, a peptide, a protein, a toxin, a cytokine, an enzyme, a structural protein, an extracellular matrix protein, another antibody, a cell or fragments thereof. The modular rAb carrier may have one or more cohesin, dockerin or both cohesin and dockerin domains that allow the formation of a complex with one or more complementary cohesin/dockerin-molecules for delivery via the antigen recognition domain of the modular rAb carrier.

The term "antigen" as used herein refers to a molecule that can initiate a humoral and/or cellular immune response in a recipient of the antigen. Antigen may be used in two different contexts with the present invention: as a target for the antibody or other antigen recognition domain of the rAb or as the molecule that is carried to and/or into a cell or target by the rAb as part of a dockerin/cohesin-molecule complement to the modular rAb carrier. The antigen is usually an agent that causes a disease for which a vaccination would be advantageous treatment. When the antigen is presented on MHC, the peptide is often about 8 to about 25 amino acids. Antigens include any type of biologic molecule, including, for example, simple intermediary metabolites, sugars, lipids and hormones as well as macromolecules such as complex carbohydrates, phospholipids, nucleic acids and proteins. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens.

The modular rAb carrier is able to carry any number of active agents, e.g., antibiotics, anti-infective agents, antiviral agents, anti-tumoral agents, antipyretics, analgesics, anti-inflammatory agents, therapeutic agents for osteoporosis, enzymes, cytokines, anticoagulants, polysaccharides, collagen, cells, and combinations of two or more of the foregoing active agents. Examples of antibiotics for delivery using the present invention include, without limitation, tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Examples of anti-tumor agents for delivery using the present invention include, without limitation, doxorubicin, Daunorubicin, taxol, methotrexate, and the like. Examples of antipyretics and analgesics include aspirin, Motrin®, Ibuprofen®, naprosyn, acetaminophen, and the like.

Examples of anti-inflammatory agents for delivery using the present invention include, without limitation, include NSAIDS, aspirin, steroids, dexamethasone, hydrocortisone, prednisolone, Diclofenac Na, and the like.

Examples of therapeutic agents for treating osteoporosis and other factors acting on bone and skeleton include for delivery using the present invention include, without limitation, calcium, alendronate, bone GLa peptide, parathyroid hormone and its active fragments, histone H4-related bone formation and proliferation peptide and mutations, derivatives and analogs thereof.

Examples of enzymes and enzyme cofactors for delivery using the present invention include, without limitation, pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Examples of cytokines for delivery using the present invention include, without limitation, interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Cytokines may be B/T-cell differentiation factors, B/T-cell growth factors, mitogenic cytokines, chemotactic cytokines, colony stimulating factors, angiogenesis factors, IFN-α, IFN-β, IFN-γ, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-α, TNF-β, NGF, CD40L, CD137L/4-1BBL, human lymphotoxin-β, G-CSF, M-CSF, GM-CSF, PDGF, IL-1α, IL1-β, IP-10, PF4, GRO, 9E3, erythropoietin, endostatin, angiostatin, VEGF or any fragments or combinations thereof. Other cytokines include members of the transforming growth factor (TGF) supergene family include the beta transforming growth factors (for example TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Examples of growth factors for delivery using the present invention include, without limitation, growth factors that can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Examples of anticoagulants for delivery using the present invention include, without limitation, include warfarin, heparin, Hirudin, and the like. Examples of factors acting on the immune system include for delivery using the present invention include, without limitation, factors which control inflammation and malignant neoplasms and factors which attack infective microorganisms, such as chemotactic peptides and bradykinins.

Examples of viral antigens and/or viral antigenic targets include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Antigens and/or antigenic targets that may be delivered using the rAb-DC/DC-antigen vaccines of the present invention include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Bacterial antigens for use with the rAb vaccine disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other *haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *haemophilus influenza; Plasmodium falciparum; neisseria meningitidis; streptococcus pneumoniae; neisseria gonorrhoeae; salmonella* serotype typhi; *shigella; vibrio cholerae*; Dengue Fever; Encephalitides; Japanese Encephalitis; lyme disease; *Yersinia pestis*; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components; and tinea fungal antigens such as trichophytin and other *coccidiodes* fungal antigen components.

Examples of protozoal and other parasitic antigens include, but are not limited to, e.g., *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

Target antigens on immune cell surfaces that can be targeted using the antigen recognition site of the antibody portion of the rAb of the present invention will generally be selected based on a number of factors, including: likelihood of internalization, level of immune cell specificity, type of immune cell targeted, level of immune cell maturity and/or activation and the like. Examples of cell surface markers for dendritic cells include, but are not limited to, MHC class I, MHC Class II, CD1, CD2, CD3, CD4, CD8, CD11b, CD14, CD15, CD16, CD 19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor or other receptor relatively specifically expressed by antigen presenting cells. Examples of cell surface markers for antigen presenting cells include, but are not limited to, MHC class I, MHC Class II, CD1, CD2, CD3, CD4, CD8, CD11b, CD14, CD15, CD16, CD 19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor or other receptor relatively specifically expressed by antigen presenting cells. Examples of cell surface markers for T cells include, but are not limited to, CD3, CD4, CD8, CD 14, CD20, CD11b, CD16, CD45 and HLA-DR.

Target antigens on cell surfaces for delivery includes those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention include tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein which is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

As used herein, the term "epitope(s)" refer to a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

As used herein, the term "promoter" describes a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (i.e., ORF) to control transcriptional initiation and/or expression of that sequence. A promoter may or may not be used in conjunction with an "enhancer," which refers to a cis-acting regulatory sequence involved in the transcriptional activation of a nucleic acid sequence. A listing of promoters and/or enhancers that may be used with the present invention is described in, e.g., U.S. Pat. No. 6,410,241, relevant descriptions and tables incorporated herein by reference.

As used herein, the terms "cell," "cell line," and "cell culture" may be used interchangeably. All of these terms also include their progeny, which is any and all subsequent generations, in vivo, ex vivo or in vitro. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of expressing a heterologous gene encoded by a vector as delivered using the rAb protein vector of the present invention. A host cell can, and has been, used as a recipient for vectors. A host cell may be "transfected" or "transformed," which refers to a process by which the exogenous nucleic acid expressing an antigen, as disclosed herein, is transferred or introduced into the host cell. A transformed cell includes the primary subject cell and its progeny.

The preparation of vaccine compositions that includes the nucleic acids that encode antigens of the invention as the active ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-γ, IL-2 and IL-12) or synthetic IFN-γ inducers such as poly I:C can be used in combination with adjuvants described herein.

Pharmaceutical products that may include a naked polynucleotide with a single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form. Another pharmaceutical product that may spring from the current invention may include a highly purified plasma lipoprotein fraction, isolated according to the methodology, described herein from either the patients blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition that includes the naked polynucleotide prebound to a highly purified lipoprotein fraction may be administered in amounts ranging from 1 μg to 1 mg polynucleotide and 1 μg to 100 mg protein.

Administration of the therapeutic virus particle to a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention may include an effective amount of the compound, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Disease States. Depending on the particular disease to be treated, administration of therapeutic compositions according to the present invention will be via any common route so long as the target tissue is available via that route in order to maximize the delivery of antigen to a site for maximum (or in some cases minimum) immune response. Administration will generally be by orthotopic, intradermal, subcutaneous, intramuscular, intraperitoneal or intravenous injection. Other areas for delivery include: oral, nasal, buccal, rectal, vaginal or topical. Topical administration would be particularly advantageous for treatment of skin cancers. Such compositions would normally be administered as pharmaceutically acceptable compositions that include physiologically acceptable carriers, buffers or other excipients.

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation that result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The antigen encoding nucleic acids of the invention may be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-γ released from the primed lymphocytes. The assays may be performed using conventional labels, such as radionuclides, enzymes, fluorescent labels and the like. These techniques are known to one skilled in the art and can be found in U.S. Pat. Nos. 3,791,932, 4,174,384 and 3,949,064, relevant portions incorporated by reference.

The modular rAb carrier and/or conjugated rAb carrier-(cohesion/dockerin and/or dockerin-cohesin)-antigen complex (rAb-DC/DC-antigen vaccine) may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently may be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered. Likewise the amount of rAb-DC/DC-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of rAb-DC/DC-antigen vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20 µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

The present invention was tested in an in vitro cellular system that measures immune stimulation of human Flu-specific T cells by dendritic cells to which Flu antigen has been targeted. The results shown herein demonstrate the specific expansion of such antigen specific cells at doses of the antigen which are by themselves ineffective in this system.

The present invention may also be used to make a modular rAb carrier that is, e.g., a recombinant humanized mAb (directed to a specific human dendritic cell receptor) complexed with protective antigens from Ricin, Anthrax toxin, and *Staphylococcus* B enterotoxin. The potential market for this entity is vaccination of all military personel and stored vaccine held in reserve to administer to large population centers in response to any biothreat related to these agents. The invention has broad application to the design of vaccines in general, both for human and animal use. Industries of interest is pharmaceutical and biotechnology One commercial application of the invention is a recombinant humanized mAb (directed to the specific human dendritic cell receptor DCIR) fused through the Ab heavy chain to antigens known or suspected to encode protective antigens. These include as examples for vaccination against various agents-hemagglutinins from Influenza H5N1; HIV gag from attenuated toxins from Ricin, Anthrax toxin, and *Staphylococcus* B enterotoxin; 'strings' of antigenic peptides from melanona anigens, etc. The potential market for this entity is preventative or therapeutic vaccination of at risk or infected people. The invention has broad application for vaccination against many diseases and cancers, both for human and animal use. Industries of interest are pharmaceutical and biotechnology. In addition, this invention has implications beyond anti-DCIR application since it describes a method to identify particularly favorable sequences to enhance secretion of recombinant antibodies.

The application of anti-DCIR combining regions for making engineered recombinant monoclonal antibodies fused to antigens as potent therapeutic or preventative vaccination agents. Use of different V-region sequences against the same combining specificity to find those most compatible with efficient expression of a H chain C-terminal linked antigen or other protein sequence.

EXAMPLE 1

Multiple Antigens Targeted in a Complex Simultaneously with the Same Engineered Humanized MAB (MATCHMAB)

One type of therapeutic (in this case, vaccination) entity envisioned is a humanized DC-targeting mAb-antigen fusion protein, where the antibody variable region specificity is directed against an internalizing human dendritic cell receptor. The present state-of-the art is to engineer the fusion of the desired antigen to the C-terminus of the mAb H chain. This paradigm obviously allows different antigens (A1, A2, A3) to be engineered to the same proven targeting mAb backbone (Y in the figure below), thus extending the utility of the one mAb to immunizing against different pathogenic agents. This concept can be further extended by engineering, e.g., the A1, A2, A3 coding regions end-to-end fused to the IgGFc C-terminal coding region.

The present invention disclosed a new paradigm for linking the antigen to the targeting mAb that extends the concept for the first time to multiple antigens targeted in a complex simultaneously with the same engineered humanized mAb (MATCHMAB).

FIG. 1 compares the prior art (top portion) with an example of the multiple antigens targeted in a complex simultaneously with the same engineered humanized mAb (MATCHMAB) (bottom portion). Y represents the humanized anti-DC targeting mAb; A1, A2, A3 are independent protective antigens, or any other desired protein domains; C1, C2, C2 are specific high affinity capture domains for, respectively, docking domains D1, D2. D3; and DnAn are the corresponding docking-antigen fusion proteins. Note that the various domains are not drawn to scale. The mAb itself is ~150 kDa, C is ~17 Da, D is ~8 kDa and A varies, but is usually >20 kDa).

The MATCHMAB is based on using cellulosome-assembly cohesin-dockerin sequences to form modular non-covalent targeting mAb-antigen complexes. The relatively small and specific cohesin-dockerin protein-protein interaction domains can allow simple customized formulation of targeting mAb-antigen complexes. Thus, a single manufactured humanized mAb (in the above notation: Y.C1.C2.C3.Cn) can be use as the basis of delivering multiple antigens in various, yet strictly defined, combinations.

Example of sequence encoding C1.C2.C3.Cn is taken from the public sequence >gi|50656899|gb|AAT79550.1| of cellulosomal anchoring scaffoldin B precursor (Bacteroides cellulosolvens). Below with blue showing the leader secretion sequence and yellow and grey highlighting various cohesin domains. Red regions are linkers spacing some of the cohesin domains.

MQSPRLKRKILSVILAVCYIISSFSIQFAATPQVNIIIGSAQGIPGSTVKVPINLQNVPEIGINNCDFTI
KFDSDILDFNSVEAGDIVPLPVASFSSNNSKDIIKFLFSDATQGNMPINENGLFAVISFKIKDNAQKGIS
NIKVSSYGSFSGMSGKEMQSLSPTFFSGSIDVSDVSTSKLDVKVGNVEGIAGTEVNVPITFENVPDNGIN
NCNFTLSYDSNALEFLTTEAGNIIPLAIADYSSYRSMEGKIKFLFSDSSQGTRSIKNDGVFANIKFKIKG
NAIRDTYRIDLSELGSFSSKQNNNLKSIATQFLSGSVNVKDIESSVSPTTSVHPTPTSVPPTPTKSSPGN
KMKIQIGDVKANQGDTVIVPITFNEVPVMGVNNCNFTLAYDKNIMEFISADAGDIVTLPMANYSYNMPSD
GLVKFLYNDQAQGAMSIKEDGTFANVKFKIKQSAAFGKYSVGIKAIGSISALSNSKLIPIESIFKDGSIT
VTNKPIVNIEIGKVKVKAGDKIKVPVEIKDIPSIGINNCNFTLKYNSNVLKYVSNEAGTIVPAPLANLSI
NKPDEGIIKLLFSDASQGGMPIKDNGIFVNLEFQAVNDANIGVYGLELDTIGAFSGISSAKMTSIEPQFN
NGSIEIFMSAQTPVPSNTEVQTPTNTISVTPTNNSTPTNNSTPKPNPLYNLNVNIGEISGEAGGVIEVPI
EFKNVPDFGINNCDFSVKYDKSIFEYVTYEAGSIVKDSIVNLACMENSGIINLLFNDATQSSSPIKNNGV
FAKLKFKINSNAASGTYQINAEGYGKFSGNLNGKLTSINPIFENGIINIGNVTVKPTSTPADSSTITPTA
TPTATPTIKGTPTVTPIYWMNVLIGNMNAAIGEEVVVPIEFKNVPPFGINNCDFKLVYDSNALELKKVEA
GDIVPEPLANLSSNKSEGKIQFLFNDASQGSMQIENGGVPAKITFKVKSTAASGIYNIRKDSVGSFSGLI
DNKMTSIGPKFTDGSIVVGTVTPTATATPSAIVTTITPTATTKPIATPTIKGTPTATPMYWMNVVIGKMN
AEVGGEVVVPIEFNNVPSFGINNCDFKLVYDATALELKNVEAGDIIKTPLANFSNNKSEEGKISFLFNDA
SQGSMQIENGGVFAKITFKVKSTTATGVYDLRKDLVGSFSGLKDNKMTSIGAEFTNGSITVAATAPTVTP
TVNATPSAATPTVTPTATATPSVTIPTVTPTATATPSVTIPTVTPTATATPSAATPTVTPTATATPSVTI
PTVTPTVTATPSDTIPTVTPTATATPSAIVTTITPTATAKPIATPTIKGTPTATPMYWMNVVIGKMNAEV
GGEVVVPIEFKNVPSFGINNCDFKLVYDATALELKNVEAGDIIKTPLANFSNNKSEEGKISFLFNDASQG
SMQIENGGVSAKITFKVKSTTAIGVYDIRKDLIGSPSGLKDSKMTSIGAEFTNGSITVATTAPTVTPTAT
ATPSVTIPTVTPTATATPGTATPGTATPTATATPGAATPTETATPSVMIPTVTPTATATPTATATPTVKG
TPTIKPVYKMNVVIGRVNVVAGEEVVVPVEFKNIPAIGVNNCNFVLEYDANVLEVKKVDAGEIVPDALIN
FGSNNSDEGKVYFLFNDALQGRMQIANDGIFANITFKVKSSAAAGIYNIRKDSVGAFSGLVDKLVPISAE
FTDGSISVESAKSTPTATATGTNVTPTVAATVTPTATPASTTPTATPTATSTVKGTPTATPLYSMNVIIG
KVNAEASGEVVVPVEFKDVPSIGINNCNFILEYDASALELDSAEAGEIVPVPLGNFSSNNKDEGKIYFLF
SDGTQGRMQIVNDGIFAKIKFKVKSTASDGTYYIRKDSVGAFSGLIEKKIIKIGAEFTDGSITVRSLTPT

PTVTPNVASPTPTKVVAEPTSNQPAGPGPITGTIPTATTTATATPTKASVATATPTATPIVVVEPTIVRP
GYNKDADLAVFISSKSRYEESSIITYSIEYKNIGKVNATNVKIAAQIPKFTKVYDAAKGAVKGSEIVWM
IGNLAVGESYTKEYKVKVDSLTKSEEYTDNTVTISSDQTVDIPENITTGNDDKSTIRVMLSNRFTPGSH
SSYILGYKDTFKPKQNVTRAEVAAMFARIMGLTVKDGAKSSYKDVSNKHWALKYIEAVTKSGIFKGYKD
STFHPNAPITRAELSTVIFNYLHLNNIAPSKVHFTDINKHWAKNYIEEIYRFKLIQGYSDGSFKPNNNIT
RAEVVTMINRMLYRGPLKVKVGSFPDVSPKYWAYGDIEEASRNHKYTRDEKDGSEILIE (SEQ ID NO.:1)

The cohesin domains (C) interact with small domains (e.g., 56 residues) called dockerins (D). These are Ca++ containing structures with two-fold symmetry and they can bind to a cognate cohesin with various affinities (e.g., 6E6 M, 2E7M). Affinities between dockerin and multiple cohesins (as found on scaffoldins) can be much higher (e.g., >E9 M). The interaction is non-covalent and is well defined (by structure analysis) for at least one C-D pair. Dockerins are designed to be domains linked to different domain (enzyme in nature), and cohesions are designed to function in linear arrays (either directly end-to-end, or joined by flexible PT-rich linkers of various sizes (e.g., 12, 17, 25, 28, 36). It is known that a particular dockerin can have specificity for a particular cohesin (e.g., a C-D pair from one bacterial species may not be interchangeable with a C-D pair from a different species). This feature makes it is possible to ensure the specific and precise interaction of various D-antigen fusion proteins with an engineered mAb containing cohesin domains of various specificities.

In practice, this invention includes adapting C-D pairs known from the literature, newly gleamed from nature, or developed with new specificities using phage display technology. The latter technology can also be used to enhance ('mature') the affinity of a C-D interaction, should this be desired. Also, engineering cysteine residues at opposing faces of the C-D interaction (based on modeling from the published C-D structures) could be used to make a covalent bond between C-D to strengthen the interaction. Furthermore, the dimeric nature of the mAb (and therefore the linked C-domains) can be used to advantage for affinity enhancement purposes. In this embodiment, e.g., the D-antigen fusion protein is engineered either with a second identical dockerin domain (D-antigen-D, or D-D-antigen), or with a homodimerization domain. This configuration, provided the linkers between domains were not constraining, will result in the preferred simultaneous binding of both D domains to the same mAb, with greatly enhanced stability compared to the single interaction.

Based on the crystal structure of the cohesin-dockerin complex (e.g., see PNAS 2003, 13809-13814, Cellulosome assembly revealed by the crystal structure of the cohesin-dockerin complex. Ana L. Carvalho *, Fernando M. V. Dias, José A. M. Prates, Tibor Nagy, Harry J. Gilbert, Gideon J. Davies, Luis M. A. Ferreira, Maria J. Romão and Carlos M. G. A. Fonte), it is apparent that one embodiment is an antigen-dockerin fusion proteins (i.e., antigen fused to the N-terminus of a dockerin). However, both from the structure and from the nature of cohesin domain organization within scaffolding, it is apparent that cohesions can be fused end-to-end, even without spacer sequences. Furthermore, it is apparent that well-described techniques are available to engineer miniaturized versions of the cohesin and dockerin domains (see for example, Proc. Natl. Acad. Sci. USA Vol. 94, pp. 10080-10085, September 1997. Structural mimicry of a native protein by a minimized binding domain. Melissa A. Starovasnik, Andrew C. Braisted, And James A. Wells).

It is recognized herein that the linker sequences have a propensity for O-linked glycosylation resulting from ST richness. Also, both the C and D domains can have potential N-linked sites. These features can be advantageous in enhancing the solubility of the mammalian cell-expressed engineered mAb through decoration with carbohydrates. Of course, the consequences of glycosylation of the C domains needs to be check by function (binding to the cognate D), and if needed rectified by site directed mutagenesis. An attractive feature of this invention is that D-A can be expressed in whatever system is known to be best. For example, the tumor antigen MART1 is a membrane protein and is best prepared in high yield via *E. coli* inclusion bodies. Schema using antigens directly fused to the mAb are restricted to antigens that are compatible with mammalian-cell expression.

Another embodiment of the invention is the use of the D-C interaction to make bi-specific mAbs joined tail-to-tail. FIG. 2 shows the use of the present invention to form Bi-specific mAbs. mAb1 (black) is expressed with C-terminal C1 and mAb2 (magenta) is expressed with C-terminal D1. Mixing equimolar mAb1 and mAb2 will result in a bi-specific 1:1 complex. Note that, since each mAb molecule contains two molar equivalents of C or D (the mAb is itself a dimeric structure), the bi-specific mAb will be greatly stabilized by two concurrent C-D interactions. Especially at lower (mAb), this will be the most stable configuration.

EXAMPLE 2

Combination of Antibody and Cohesion/Dockerin Domains and Antigens

Example 2 shows that particular cohesin and dockerin domains can be successfully and efficiently secreted from mammalian cells as fusion proteins while maintaining the specific and high affinity cohesin-dockerin protein-protein interaction. While the extensive cohesin-dockerin literature teaches the expectation that such fusion proteins should have this functionality, it does not describe production of such fusion proteins in mammalian secretion systems. The state of scientific knowledge does not allow the prediction of the discovery since the rules (other than features such as signal peptide) for successful secretion are not fully established. Furthermore, the cohesin linker regions are known to be glycosylated in their native bacteria, and the cohesin and dockerin domains contain predicted glycosylation sites. While this may actually favor secretion from mammalian cells, it is unclear if 'unnatural' glyosylation will perturb the cohesis-dockerin interaction.

While cohesin-dockerin interaction for various commercial applications has been published, the present invention is based on a previously unrealized utility for this interaction built around assembling specific protein complexes unrelated to the envisioned controlled assembly enzyme applications.

The invention includes the use of all cohesin-dockerin sequences from diverse cellulose degrading microbes, but describes the application of specific cohesin and dockerin and linker sequences from the microbe *Clostridium thermocellum*. For example, the sequence described in Table 1 encodes the H chain of a human IgG4 linked at the C-terminal codon to a *Clostridium thermocellum* dockerin sequence (called rAb.doc). Other embodiments of rAb.doc proteins are described similarly in Table 2 and these are engineered by simply transferring the dockerin coding region as a DNA fragment to vectors encoding the different H chain entities.

TABLE 1 shows the nucleic acid and amino acid sequences for rAB-pIRES2(hIgG4H-Dockerin) or C52. DNA (entire coding region) and amino acid sequence (the predicted secreted product) of human IgG4H.doc fusion protein is shown below. The dockerin domain (taken from *Clostridium thermocellum* celD is highlighted in yellow and the H chain and dockerin joining sequence is underlined. The highly predicted N-linked glycosylation site within the dockerin domain is highlighted in red.

TABLE 1 rAB-pIRES2(hIgG4H-Dockerin) or C52.

ATGGACCTCCTGTGCAAGAACATGAAGCACCTGTGGTTCTTCCTCCTGCTGGTGGCGGCTCCCAGATGGGTCCTGTCCCGGCTGC
AGCTGCAGGAGTCGGGCCCAGGCCTGCTGAAGCCTTCGGTGACCCTGTCCCTCACCTGCACTGTCTCGGGTGACTCCGTCGCCAG
TAGTTCTTATTACTGGGGCTGGGTCCGTCAGCCCCCAGGGAAGGGACTCGAGTGGATAGGGACTATCAATTTTAGTGGCAATATG
TATTATAGTCCGTCCCTCAGGAGTCGAGTGACCATGTCGGCAGACATGTCCGAGAACTCCTTCTATCTGAAATTGGACTCTGTGA
CCGCAGCAGACACGGCCGTCTATTATTGTGCGGCAGGACACCTCGTTATGGGATTTGGGGCCCACTGGGGACAGGGAAAACTGGT

CTCCGTCTCTCCAGCTTCCACCAAGGGCCCATCCGTCTTCCCCCTGGCGCCCTGCTCCAGGAGCACCTCCGAGAGCACAGCCGCC
CTGGGCTGCCTGGTCAAGGACTACTTCCCCGAACCGGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTGACCGTGCCCTCCAGCAGCTTGGGCACGAAGACCTA
CACCTGCAACGTAGATCACAAGCCCAGCAACACCAAGGTGGACAAGAGAGTTGAGTCCAAATATGGTCCCCCATGCCCACCCTGC
CCAGCACCTGAGTTCGAAGGGGGACCATCAGTCTTCCTGTTCCCCCCAAAACCCAAGGACACTCTCATGATCTCCCGGACCCCTG
AGGTCACGTGCGTGGTGGTGGACGTGAGCCAGGAAGACCCCGAGGTCCAGTTCAACTGGTACGTGGATGGCGTGGAGGTGCATAA
TGCCAAGACAAAGCCGCGGGAGGAGCAGTTCTTCAACAGCACGTACCGTGGTCAGCGTCCTCACCGTCCTGCACCAGGACTGGCTG
AACGGCAAGGAGTACAAGTGCAAGGTCTCCAACAAAGGCCTCCCGTCCTCCATCGAGAAAACCATCTCCAAAGCCAAAGGGCAGC
CCCGAGAGCCACAGGTGTACACCCTGCCCCCATCCCAGGAGGAGATGACCAAGAACCAGGTCAGCCTGACCTGCCTGGTCAAAGG
CTTCTACCCCAGCGACATCGCCGTGGAGTGGGAGAGCAATGGGCAGCCGGAGAACAACTACAAGACCACGCCTCCCGTGCTGGAC
TCCGACGGCTCCTTCTTCCTCTACAGCAGGCTAACCGTGGACAAGAGCAGGTGGCAGGAGGGGAATGTCTTCTCATGCTCCGTGA
TGCATGAGGCTCTGCACAACCACTACACACAGAAGAGCCTCTCCCTGTCTCTGGGTAAAGCTAGCAATTCTCCTCAAAATGAAGT
ACTGTACGGAGATGTGAATGATGACGGAAAAGTAAACTCCACTGACTTGACTTTGTTAAAAAGATATGTTCTTAAAGCCGTCTCA
ACTCTCCCTTCTTCCAAAGCTGAAAAGAACGCAGATGTAAATCGTGACGGAAGACTTAATTCCAGTGATGTCACAATACTTTCAA
GATATTTGATAAGGGTAATCGAGAAATTACCAATATAA (SEQ ID NO.: 2)

RLQLQESGPGLLKPSVTLSLTCTVSGDSVASSSYYWGWVRQPPGKGLEWIGTINFSGNMYYSPSLRSRVTMSADMSENSFYLKLD
SVTAADTAVYYCAAGHLVMGFGAHWGQGKLVSVSPASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVESKYGPPCPPCPAPEFEGGPSVFLFPPKPKDTLMISR
TPEVTCVVVDVSQEDPEVQFNWYVDGVEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLDSDGSFFLYSRLTVDKSRWQEGNVFSC
SNMHEALHNHYTQKSLSLSLGKASNSPQNEVLYGDVNDDGKVNSTDLTLLKRYVLKAVSTLPSSKAEKNADVNRDGRVNSDVTI
LSRYLIRVIEKLPI (SEQ ID NO.: 3)

TABLE 2 shows the nucleic acid and amino acid sequences for rAB-pIRES2(mAnti-DCIR2C9H-LV-hIgG4H-C-Dockerin) or C82. DNA (entire coding region) and amino acid sequence (the predicted secreted product) is shown below. The dockerin domain is highlighted in yellow and the H chain and dockerin joining sequence is underlined. The IgG variable region is highlighted in blue. The highly predicted N-linked glycosylation site within the dockerin domain is highlighted in red.

TABLE 2 rAB-pIRES2(mAnti-DCIR2C9H-LV-hIgG4H-C-Dockerin) or C82.

```
ATGAAATGCAGCTGGGTCATCTTCTTCCTGATGGCAGTGGTTACAGGGGTCAATTCAGAGGTTCAGCTGCAGCAGTCTGGGGCTG
AGCTTGTGAGGCCAGGGGCCTTAGTCAAGTTGTCCTGCAAAGCTTCTGGCTTCAACATTAATGACTACTATATCCACTGGGTGAA
GCAGCGGCCTGAACAGGGCCTGGAGCGGATTGGATGGATTGATCCTGACAATGGTAATACTATATATGACCCGAAGTTCCAGGGC
AAGGCCAGTATAACAGCAGACACATCCCCCAACACAGCCTACCTGCAGCTCAGCAGCCTGACATCTGAGGACACTGCCGTCTATT
ACTGTGCTAGAACCCGATCTCCTATGGTTACGACGGGGTTTGTTTACTGGGGCCAAGGGACTGTGGTCACTGTCTCTGCAGCCAA
AACGAAGGGCCCATCCGTCTTCCCCCTGGCGCCCTGCTCCAGGAGCACCTCCGAGAGCACAGCCGCCCTGGGCTGCCTGGTCAAG
GACTACTTCCCCGAACCGGTGACGGTGTCGTGGAACTCAGGCGCCCTGACCAGCGGCGTGCACACCTTCCCGGCTGTCCTACAGT
CCTCAGGACTCTACTCCCTCAGCAGCGTGGTGACCGTGCCCTCCAGCAGCTTGGGCACGAAGACCTACACCTGCAACGTAGATCA
CAAGCCCAGCAACACCAAGGTGGACAAGAGAGTTGAGTCCAAATATGGTCCCCCATGCCCACCCTGCCCAGCACCTGAGTTCGAA
GGGGGACCATCAGTCTTCCTGTTCCCCCCAAAACCCAAGGACACTCTCATGATCTCCCGGACCCCTGAGGTCACGTGCGTGGTG
TGGACGTGAGCCAGGAAGACCCCGAGGTCCAGTTCAACTGGTACGTGGATGGCGTGGAGGTGCATAATGCCAAGACRAAGCCGCG
GGAGGAGCAGTTCAACAGCACGTACCGTGTGGTCAGCGTCCTCACCGTCCTGCACCAGGACTGGCTGAACGGCAAGGAGTACAAG
TGCAAGGTCTCCAACAAAGGCCTCCCGTCCTCCATCGAGAAAACCATCTCCAAAGCCAAAGGGCAGCCCCGAGAGCCACAGGTGT
ACACCCTGCCCCCATCCCAGGAGGAGATGACCAAGAACCAGGTCAGCCTGACCTGCCTGGTCAAAGGCTTCTACCCCAGCGACAT
CGCCGTGGAGTGGGAGAGCAATGGGCAGCCGGAGAACAACTACAAGACCACGCCTCCCGTGCTGGACTCCGACGGCTCCTTCTTC
CTCTACAGCAGGCTAACCGTGGACAAGAGCAGGTGGCAGGAGGGGAATGTCTTCTCATGCTCCGTGATGCATGAGGCTCTGCACA
ACCACTACACACAGAAGAGCCTCTCCCTGTCTCTGGGTAAAGCTAGCAATTCTCCTCAAAATGAAGTACTGTACGGAGATGTGAA
TGATGACGGAAAAGTAAACTCCACTGACTTGACTTTGTTAAAAAGATATGTTCTTAAAGCCGTCTCAACTCTCCCTTCTTCCAAA
GCTGAAAAGAACGCAGATGTAAATCGTGACGGAAGAGTTAATTCCAGTGATGTCACAATACTTTCAAGATATTTCATAAGGGTAA
TCGAGAAATTACCAATATAA (SEQ ID NO.: 4)
```

```
EVQLQQSGAELVRPGALVKLSCKASGFNINDYYIHWVKQRPEQGLERIGWIDPDNGNTIYDPKFQGKASITADTSPNTAYLQLSS
LTSEDTAVYYCARTRSPMVTTGFVYWGQGTVVTVSAAKTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRVESKYGPPCPPCPAPEFEGGPSVFLFPPKPKDTLMIS
RTPEVTCVVVDVSQEDPEVQFNWYVDGVEVHNAKTKPREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPENNYKTTPPVLDSDGSFFLYSRLTVDKSRWQEGNVFS
CSVMHEALHNHYTQKSLSLSLGKASNSPQNEVLYGDVNDDGKVNSTDLTLLKRYVLKAVSTLPSSKAEKNADVNRDGRVNSSDVT
ILSRYLIRVIEKLPI. (SEQ ID NO.: 5)
```

TABLE 3 shows the nucleic acid and amino acid sequences for rAB-(mAnti -ASGPR__49C11__7H-SLAML-V-hIgG4H-C-Dockerin) or C153. DNA (entire coding region) and amino acid sequence (the predicted secreted product) is shown below. The dockerin domain is highlighted in yellow and the H chain and dockerin joining sequence is underlined. The IgG variable region is highlighted in blue. The highly predicted N-linked glycosylation site within the dockerin domain is highlighted in red.

TABLE 4 shows the nucleic acid and amino acid sequences for rAB-pIRES2(mAnti-DC-SIGNL16E7H-LV-hIgG4H-C-Dockerin) or C92. DNA (entire coding region) and amino acid sequence (the predicted secreted product) is shown below. The dockerin domain is highlighted in yellow and the H chain and dockerin joining sequence is underlined. The IgG variable region is highlighted in blue. The highly predicted N-linked glycosylation site within the dockerin domain is highlighted in red.

TABLE 3 rAB-(mAnti-ASGPR__49C11__7H-SLAML-V-hIgG4H-C-Dockerin) or C153.

```
ATGGACCCCAAAGGCTCCCTTTCCTGGAGAATACTTCTGTTTCTCTCCCTGGCTTTTGAGTTGTCGTACGGAGATGTGCAGCTTC
AGGAGTCAGGACCTGACCTGGTGAAACCTTCTCAGTCACTTTCACTCACCTGCACTGTCACTGGCTACTCCATCACCAGTGGTTA
TAGCTGGCACTGGATCCGGCAGTTTCCAGGAAACAAACTGGAATGGATGGGCTACATACTCTTCAGTGGTAGCACTAACTACAAC
CCATCTCTGAAAAGTCGAATCTCTATCACTCGAGACACATCCAAGAACCAGTTCTTCCTGCAGTTGAATTCTGTGACTACTGAGG
ACACAGCCACATATTTCTGTGCAAGATCTAACTATGGTTCCTTTGCTTCCTGGGGCCAAGGGACTCTGGTCACTGTCTCTGCAGC
CAAAACAAAGGGCCCATCCGTCTTCCCCCTGGCGCCCTGCTCCAGGAGCACCTCCGAGAGCACAGCCGCCCTGGGCTGCCTGGTC
AAGGACTACTTCCCCGAACCGGTGACGGTGTCGTGGAACTCAGGCGCCCTGACCAGCGGCGTGCACACCTTCCCGGCTGTCCTAC
AGTCCTCAGGACTCTACTCCCTCAGCAGCGTGGTCACCGTGCCCTCCAGCAGCTTGGGCACGAAGACCTACACCTGCAACGTAGA
TCACAAGCCCAGCAACACCAAGGTGGACAAGAGAGTTGAGTCCAAATATGGTCCCCCATGCCCACCCTGCCCAGCACCTGAGTTC
GAAGGGGGACCATCAGTCTTCCTGTTCCCCCCAAAACCCAAGGACACTCTCATGATCTCCCGGACCCCTGAGGTCACGTGCGTGG
TGGTGGACGTGAGCCAGGAAGACCCCGAGGTCCAGTTCAACTGGTACGTGGATGGCGTGGAGGTGCATAATGCCAAGACAAAGCC
GCGGGAGGAGCAGTTCAACAGCACGTACCGTGTGGTCAGCGTCCTCACCGTCCTGCACCAGGACTGGCTGAACGGCAAGGAGTAC
AAGTGCAAGGTCTCCAACAAAGGCCTCCCGTCCTCCATCGAGAAAACCATCTCCAAAGCCAAAGGGCAGCCCCGAGAGCCACAGG
TGTACACCCTGCCCCCATCCCAGGAGGAGATGACCAAGAACCAGGTCAGCCTGACCTGCCTGGTCAAAGGCTTCTACCCCAGCGA
CATCGCCGTGGAGTGGGAGAGCAATGGGCAGCCGGAGAACAACTACAAGACCACGCCTCCCGTGCTGGACTCCGACGGCTCCTTC
TTCCTCTACAGCAGGCTAACCGTGGACAAGAGCAGGTGGCAGGAGGGGAATGTCTTCTCATGCTCCGTGATGCATGAGGCTCTGC
ACAACCACTACACACAGAAGAGCCTCTCCCTGTCTCTGGGTAAAGCTAGCAATTCTCCTCAAAATGAAGTACTGTACGGAGATGT
GAATGATGACGGAAAAGTAAACTCCACTGACTTGACTTTGTTAAAAAGATATGTTCTTAAAGCCGTCTCAACTCTCCCTTCTTCC
AAAGCTGAAAAGAACGCAGATGTAAATCGTGACGGAAGAGTTAATTCCAGTGATGTCACAATACTTTCAAGATATTTGATAAGGG
TAATCGAGAAATTACCAATATAA (SEQ ID NO.: 6)
```

```
DVQLQESGPDLVKPSQSLSLTCTVTGYSITSGYSWHWIRQFPGNKLEWMGYILFSGSTNYNPSLKSPISITRDTSKNQFFLQLNS
VTTEDTATYFCARSNYGSFASWGQGTLVTVSAAKTKGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYGPPCPPCPAPEFEGGPSVFLFPPKPKDTLMISRTPE
VTCVVVDVSQEDPEVQFNWYVDGVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFLYSRLTVDKSRWQEGNVFSCSVM
HEALHNHYTQKSLSLSLGKASNSPQNEVLYGDVNDDGKVNSTDLTLLKRYVLKAVSTLPSSKAEKNADVNRDGRVNSSDVTILSR
YLIRVIEKLPI (SEQ ID NO.: 7)
```

TABLE 4

| rAB-pIRES2(mAnti-DC-SIGNL16E7H-LV-hIgG4H-C-Dockerin) or C92 |
|---|
| ATGGAAAGGCACTGGATCTTTCTCTTCCTGTTTTCAGTAACTGCAGGTGTCCACTCCCAGGTCCAGCTTCAGCAGTCTGGGGCTG<br>AGCTGGCAAAACCTGGGGCCTCAGTGAAGATGTCCTGCAAGGCTTCTGGCTACACCTTTACTACCTACTGGATGCACTGGGTAAA<br>ACAGAGGCCTGGACAGGGTCTGGAATGGATTGGATACATTAATCCTATCACTGGTTATACTGAGTACAATCAGAAGTTCAAGGAC<br>AAGGCCACCTTGACTGCAGACAAATCCTTCCAGCACAGCCTACATGCAACTGAGCAGCCTGACATCTGAGGCTCTGCAGTCTATT<br>ACTGTGCAAGAGAGGGTTTAAGTGCTATGGACTATTGGGGTCAGGGAACCTCAGTCACCGTCACCTCAGCCAAAACAACGGGCCC<br>ATCCGTCTTCCCCCTGGCGCCCTGCTCCAGGAGCACCTCCGAGAGCACAGCCGCCCTGGGCTGCCTGGTCAAGGACTACTTCCCC<br>GAACCGGTGACGGTGTCGTGGAACTCAGGCGCCCTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACGAAGACCTACACCTGCAACGTAGATCACAAGCCCAGCAA<br>CACCAAGGTGGACAAGAGAGTTGAGTCCAAATATGGTCCCCCATGCCCACCCTGCCCAGCACCTGAGTTCGAAGGGGGACCATCA<br>GTCTTCCTGTTCCCCCCAAAACCCAAGGACACTCTCATGATCTCCCGGACCCCTGAGGTCACGTGCGTGGTGGTGGACGTGAGCC<br>AGGAAGACCCCAGGTCCAGTTCAACTGGTACGTGGATGGCGTGCCAGGTGCATAATGCCAAGACAAAGCCGCGGGAGGAGCAGTT<br>CAACAGCACGTACCGTGTGGTCAGCGTCCTCACCGTCCTGCACCAGGACTGGCTGAACGGCAAGGAGTACAAGTGCAAGGTCTCC<br>AACAAAGGCCTCCCGTCCTCCATCGAGAAAACCATCTCCAAAGCCAAAGGGCAGCCCCGAGAGCCACAGGTGTACACCCTGCCCC<br>CATCCCAGGAGGAGATGACCAAGAACCAGGTCAGCCTGACCTGCCTGGTCAAAGGCTTCTACCCCAGCGACATCGCCGTGGAGTG<br>GGAGAGCAATGGGCAGCCGGAGAACAACTACAAGACCACGCCTCCCGTGCTGGACTCCGACGGCTCCTTCTTCCTCTACAGCAGG<br>CTAACCGTGGACAAGAGCAGGTGGCAGGAGGGGAATGTCTTCTCATGCTCCGTGATGCATGAGGCTCTGCACAACCACTACACAC<br>AGAAGAGCCTCTCCCTGTCTCTGGGTAAAGCTAGCAATTCTCCTCAAAATGAAGTACTGTACGGAGATGTGAATGATGACGGAAA<br>AGTAAACTCCACTGACTTGACTTTGTTAAAAAGATATGTTCTTAAAGCCGTCTCAACTCTCCCTTCTTCCAAAGCTGAAAAGAAC<br>GCAGATGTAAATCGTGACGGAAGAGTTAATTCCAGTGATGTCACAATACTTTCAAGATATTTGATAAGGGTAATCGAGAAATTAC<br>CAATATAA (SEQ ID NO.: 8) |
| QVQLQQSGAELAKPGASVKMSCKASGYTFTTYWMHWVKQRPGQGLEWIGYINPITGYTEYNQKFKDKATLTADKSSSTAYMQLSS<br>LTSEDSAVYYCAREGLSAMDYWGQGTSVTVTSAKTTGPSVFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVESKYGPPCPPCPAPEFEGGPSVFLFPPKPKDTLMISRTPE<br>VTCVVVDVSQEDPEVQFNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTVDKSRWQEGNVFSCSVM<br>HEALHNHYTQKSLSLSLGKASNSPQNEVLYGDVNDDGKVNSTDLTLLKRYVLKAVSTLPSSKAEKNADVNRDGRVNSSDVTILSR<br>YLIRVIEKLPI (SEQ ID NO.: 9) |

Mammalian expression plasmids encoding such rAb.doc IgG H chain proteins are created using standard molecular biology techniques and can be based on commercially available expression plasmid vectors such as pIRES2-DsRed2 (BD Biosciences). To produce secreted rAb.doc, mammalian cells are co-transfected with this expression plasmid and an expression plasmid encoding a complimentary IgG L chain (exemplified in Table 3). Standard protocols (such as the dicted (Potential 0.6426, NetNGlyc 1.0 Server—Technical University of Denmark) site within the dockerin sequence.

TABLE 5 shows the nucleic acid and amino acid sequences for rAB-pIRES2(mAnti-DC-SIGNL16E7K-LV-hIgGK-C) or C73. DNA (entire coding region) and amino acid sequence (the predicted secreted product) of IgG Kappa protein fusing the V region from the mAnti-DC-SIGNL16E7 hybridoma (highlighted in blue) to a human C region (highlighted in yellow).

TABLE 5

| rAB-pIRES2(mAnti-DC-SIGNL16E7K-LV-hIgGK-C) or C73. |
|---|
| ATGCATCGCACCAGCATGGGCATCAAGATGGAGTCACAGATTCAGGCATTTGTATTCGTGTTTCTCTGGTTGTCTGGTGTTGGCG<br>GAGACATTGTGATGACCCAGTCTCACAAATTCATGTCCACATCAGTAGGAGACAGGGTCAGCGTCACCTGCAAGGCCAGTCAGGA<br>TGTGACTTCTGCTGTAGCCTGGTATCAACAAAAACCAGGGCAATGTCCTAAACTACTGATTTACTGGGCATCCACCCGGCACACT<br>GGAGTCCCTGATCGCTTCACAGGCAGTGGATCTGGGACAGATTATACTCTCACCATCAGCAGTGGGCAGGCTGAAGACCTGGCAC<br>TTTATTACTGTCACCAATATTATAGCGCTCCTCGGACGTTCGGTGGAGGCACCAAGCTCGAGATCAAACGAACTGTGGCTGCACC<br>ATCTGTCTTCATCTTCCCGCCATCTGATGAGCAGTTGAAATCTGGAACTGCCTCTGTTGTGTGCCTGCTGAATAACTTCTATCCC<br>AGAGAGGCCAAAGTACAGTGGAAGGTGGATAACGCCCTCCAATCGGGTAACTCCCAGGAGAGTGTCACAGAGCAGGACAGCAAGG<br>ACAGCACCTACAGCCTCAGCAGCACCCTGACGCTGAGCAAAGCAGACTACGAGAAACACAAAGTCTATGCCTGCGAAGTCACCCA<br>TCAGGGCCTGAGCTCGCCCGTCACAAAGAGCTTCAACAGGGGAGAGTGTTAG (SEQ ID NO.: 10) |
| DIVMTQSHKFMSTSVGDRVSVTCKASQDVISAVAWYQQKPGQSPKLLIYWASTRHIGVFDRFTGSGSGTDYTLTISSGQAEDLAL<br>YYCHQYYSAPRTFGGGTKLEIKRTVAAPSVFIFPPSDEQLKSGTASVVCLLNNFYPREAKVQWKVDNALQSGNSQESVTEQDSKD<br>STYSLSSTLTLSKADYEKHKVYACEVTHQGLSSPVTKSFNRGEC. (SEQ ID NO.: 11) |

FreeStyle™ 293 Expression System, Invitrogen) are used as for mammalian cells, transfection reagents, and culture media. Transfected cells are cultured for 3-7 days and the culture supernatant is harvested by centrifugation, clarified by filtration, and the rAB.doc protein purified by Protein G affinity chromatography using protocols from the column manufacturer (GE Pharmacia).

FIG. 3 shows analysis of typical secreted rAb.doc products by reducing SDS.PAGE with staining by Coomassie Brilliant Blue. This analysis shows that the rAb.doc is efficiently produced as a secreted H+L chain dimer. Heterogeneity in the H chain likely reflects N-linked glycosylation at a highly pre- FIG. 3 shows Protein G affinity purified secreted rAb proteins analyzed by reducing SDS.PAGE and Coomassie Brilliant Blue staining. Lanes are from left to right.

The invention embodies the unanticipated presence and use of this glycosylation site that likely confers onto mammalian cell-secreted dockerin fusion proteins desirable solubility and pharmacokinetic properties well known to be associated with glycosylation. FIG. 2 shows that rAb.antigen fusion proteins employing identical IgG H and L sequences can differ dramatically in efficiency of secretion. In both sited examples, rAb.doc entities are well expressed compared to rAb fused to Influenza HA5 sequences which typically express very poorly. The invention also embodies the unanticipated capacity of the dockerin domain to not significantly hinder the secretion of the associated rAb entity. Furthermore, the invention embodies the property of the dockerin domain to not hinder the functionality of the rAb specific antigen combining regions. This property is exemplified in FIG. 5 which shows concordance between IgFc reactivity and LOX-1 reactivity between anti-LOX1_15C4 rAb proteins and anti-LOX1_15C4.doc.

Figure 4A:
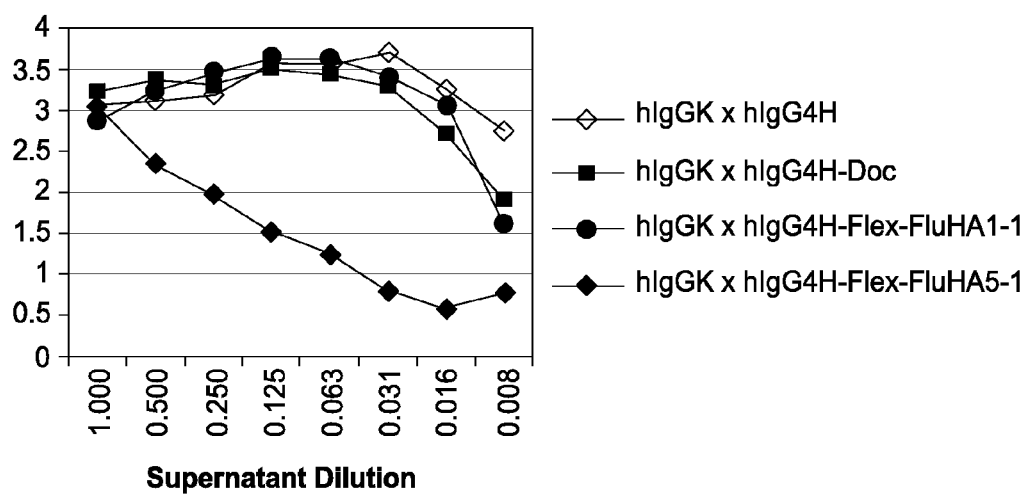
FIGS. 4A and 4B show the measurement by anti-human IgFc ELISA of levels of secretion of various rAb.fusion proteins.
Figure 4B:
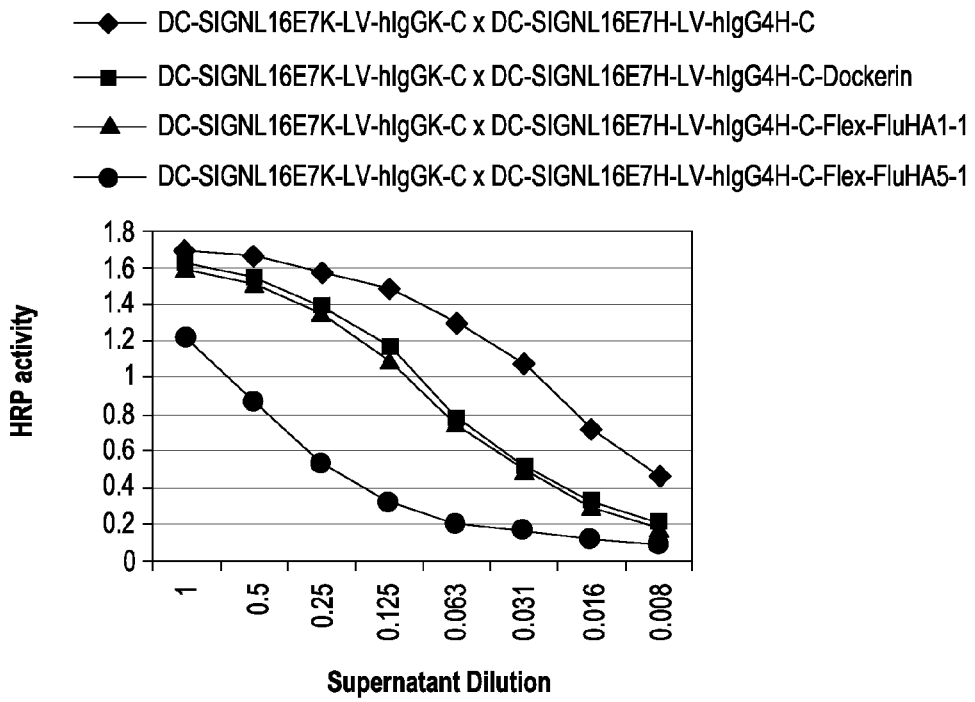

FIGS. 4A and 4B show the measurement by anti-human IgFc ELISA of levels of secretion of various rAb.fusion proteins. 2.5 ug each of the H and L chain expression plasmids were transfected into 293F cells and two-fold dilutions of supernatant samples were tested after three days of culture. Y axis values are arbitrary HRP activity.

Figure 5:
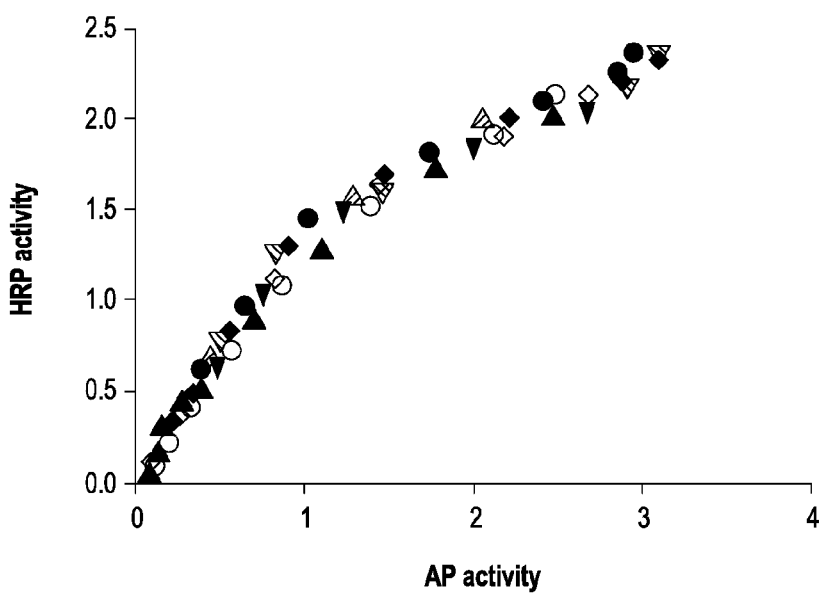
FIG. 5 shows the measurement by anti-human IgFc ELISA (HRP activity) and LOX-1.alkaline phoshatase binding (AP activity) of secreted anti-LOX1_15C4 rAb.(blue symbols) and anti-LOX1_15C4.doc rAb (red symbols) proteins.

FIG. 5 shows the measurement by anti-human IgFc ELISA (HRP activity) and LOX-1.alkaline phoshatase binding (AP activity) of secreted anti-LOX1_15C4 rAb.(blue symbols) and anti-LOX1_15C4.doc rAb (red symbols) proteins. Different ratios totalling 5 ug of the H and L chain expression plasmids were transfected into 293F cells and supernatant samples were tested after three days of culture.

The invention embodies the property of the dockerin domain to be efficiently and functionally expressed in the context of fusion proteins other than hIgG4 and its close derivatives. For example, Table 6 shows the sequence of a rAb.doc entity based on a mouse IgG2b H chain fusion protein.

TABLE 6 shows the nucleic acid and amino acid sequences for rAB-pCMV(mIgG2bH-Dockerin) or C19. DNA (entire coding region) and amino acid sequence (the predicted secreted product) is shown. The dockerin domain is highlighted in yellow and the H chain and dockerin joining sequence is underlined. The highly predicted N-linked glycosylation site within the dockerin domain is highlighted in red.

Figure 6:
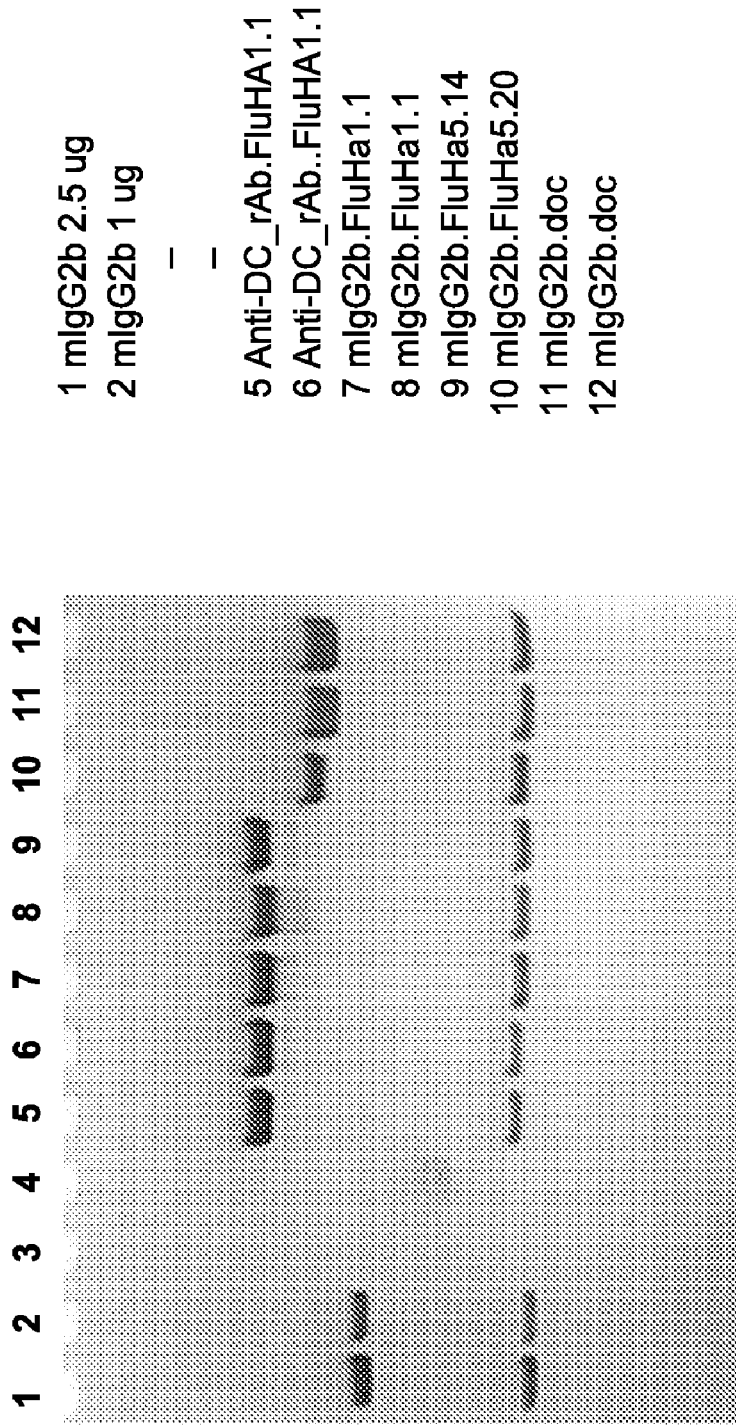
FIG. 6 shows that when co-transfected with a mIgG kappa expression plasmid, rAB-pCMV(mIgG2bH-Dockerin) plasmid directs the efficient secretion of rAB-mIgG2b.Dockerin fusion protein.

FIG. 6 shows that when co-transfected with a mIgG kappa expression plasmid, rAB-pCMV(mIgG2bH-Dockerin) plasmid directs the efficient secretion of rAB-mIgG2b.Dockerin fusion protein. In FIG. 6, a Protein G affinity purified rAb proteins secreted from transfected 293 F cells analyzed by reducing SDS.PAGE and Coomassie Brilliant Blue staining. Lanes 11 and 12 show mIgG2b.doc products.

The use of the rAb.doc invention detailed above is the assembly of rAb-antigen or toxin or activator or enzyme complexes via the specificity and tenacity of the dockerin-cohesin interaction. Table 5 shows one embodiment of the invention in the form of a cohesin.alkaline phosphatase fusion protein (coh.AP). Also described are additional embodiments such as an alkaline phosphatase fusion protein containing two cohesion domains (coh.coh.AP) and other proteins are examples of the generality of the invention such as the single cohesin domain fused to other sequences such as the mature sequence of human prostate specific antigen (coh.hPSA) and to the HA1 domain of influenza A HA5 (coh.Flu HA5-1).

TABLE 7 shows the nucleic acid and amino acid sequences for Mam-pCDM8(Cohesin-SLAML-AP-6×His) or C16. DNA (entire coding region) and amino acid sequence (the predicted secreted product) is shown below. The cohesin domain is highlighted in yellow and the cohesin and alkaline phosphatase joining sequence is underlined. The highly predicted (G-score >0.5, NetOGlyc 3.1 Server—Technical University of Denmark) O-linked glycosylation sites within the cohesin domain and the linker distal to the cohesin domain are highlighted in red. Residues highlighted grey are a C-terminal His tag to facilitate purification via metal affinity chromatography.

TABLE 6 rAB-pCMV(mIgG2bH-Dockerin) or C19.

```
ATGGGATGGTCATGTATCATCCTTTTTCTAGTAGCAACTGCAACTGGAGTACATTCACAGGTCCAACTGCAGCAGCCTGGGGCTG
AGCTGGTGAGGCCTGGGACTTCAGTGAAGTTGTCCTGCAAGGCTTCTGGTTACATCTTTACCAGCTACTGGATGCACTGGGTAAA
GCAGAGGCCTGGACAAGGCCTTGAGTGGATCGGACTGATTGATCCTTCTGATAGTTATAGTAAGTACAATCAAAAGTTCAAGGGC
AAGGCCACATTGACTGTAGACACATCCTCCAGCACAGCCTACATGCAGCTCAGCAGCCTGACATCTGAGGACTCTGCGGTCTATT
ACTGTGCAAGAGGGGAGCTCAGTGACTTCTGGGGCCAAGGCACCACTCTCACAGTCTCCTCAGCCAAAACAACACCCCCATCAGT
CTATCCACTGGCCCCTGGGTGTGGAGATACAACTGGTTCCTCTGTGACTCTGGGATGCCTGGTCAAGGGCTACTTCCCTGAGTCA
GTGACTGTGACTTGGAACTCTGGATCCCTGTCCAGCAGTGTGCACACCTTCCCAGCTCTCCTGCAGTCTGGACTCTACACTATGA
GCAGCTCAGTGACTGTCCCCTCCAGCACCTGGCCAAGTCAGACCGTCACCTGCAGCGTTGCTCACCCAGCCAGCAGCACCACGGT
GGACAAAAAACTTGAGCCCAGCGGGCCCATTTCAACAATCAACCCCTGTCCTCCATGCAAGGAGTGTCACAAATGCCCAGCTCCT
AACCCTCGAGGGTGGACCATCCGTCTTCATCTTCCCTCCAAATATCAAGGATGTACTCATGATCTCCCTGACACCCAAGGTCACGT
GTGTGGTGGTGGATGTGAGCGAGGATGACCCAGACGTCCGGATCAGCTGGTTTGTGAACAACGTGGAAGTACACACAGCTCAGAC
ACAAACCCATACACAGGATTACAACAGTACTATCCGGGTGGTCAGTGCCCTCCCCATCCAGCACCAGGACTGGATGAGTGGCAAG
GAGTTCAAATGCAAGGTCAACAACAAAGACCTCCCATCACCCATCGAGAGAACCATCTCAAAAATAAAGGGGCTAGTCAGAGCTC
CACAAGTATACATCTTGCCGCCACCAGCAGAGCAGTTCTTCCAGGAAAGATGTCAGTCTCACTTGCCTGGTCGTGGGCTTCAACCC
TGGAGACATCAGTGTGGAGTGGACCAGCAATGGGCATACAGAGGAGAACTACAAGGACACCGCACCAGTCCTGGACTCTGACGGT
TCTTACTTCATATACAGCAAGCTCGATATAAAAACAAGCAAGTGGGAGAAAACAGATTCCTTCTCATGCAACGTGAGACACGAGG
GTCTGAAAAATTACTACCTGAAGAAGACCATCTCCCGGTCTCCGGGTAAAGCTAGCAATTCTCCTCAAAATGAAGTACTGTACGG
AGATGTGAATGATGACGGAAAAGTAAACTCCACTGACTTGACTTTGTTAAAAAGATATGTTCTTAAAGCCGTCTCAACTCTGCCT
TCTTCCAAAGCTGAAAAGAACGCAGATGTAAATCGTGACGGAAGAGTTAATTCCAGTGATGTCACAATACTTTCAAGATATTTGA
TAAGGGTAATCGAGAAATTACCAATATAA (SEQ ID NO.: 12)
```

```
QVQLQQPGAELVRPGTSVKLSCKASGYIFTSYWMHWVKQRPGQGLEWIGLIDPSDSYSKYNQKFKGKATLTVDTSSSTAYMQLSS
LTSEDSAVYYCARGELSDFWQGTTLTVSSAKTTPPSVYPLAPGCGDTTGSSVTLGCLVKGYFPESVTVTWNSGSLSSSVHTFPA
LLQSGLYTMSSSVTVPSSTWPSQTVTCSVAHPASSTTVDKKLEPSGPISTINPCPPCKECHKCPAPNLEGGPSVFIFPPNIKDVL
MISLTPKVTCVVVDVSEDDPDVRISWFVNNVEVHTAQTQTHREDYNSTIRVVSALPIQHQDWMSGKEFKCKVNNKDLPSPIERTI
SKIKGLVRAPQVYILPPPAEQLSRKDVSLTCLVVGFNPGDISVEWTSMGHTEENYKDTAPVLDSDGSYFIYSKLDIKTSKWEKTD
SFSCNVRHEGLKNYYLKKTISRSPGKASNSPQNEVLYGDVNDDGKVNSTDLTLLKRYVLKAVSTLPSSKAEKNADVNRDGRVNSS
DVTILSRYLIRVIEKLPI. (SEQ ID NO.: 13)
```

TABLE 7

Mam-pCDM8(Cohesin-SLAML-AP-6xHis) or C16.

```
ATGGATCCCAAAGGATCCCTTTCCTGGAGAATACTTCTGTTTCTCTCCCTGGCTTTTGAGTTGAGCTACGGACTCGACGATCTGG
ATGCAGTAAGGATTAAAGTGGACACAGTAAATGCAAAACCGGGAGACACAGTAAGAATACCTGTAAGATTCAGCGGTATACCATC
CAAGGGAATAGCAAACTGTGACTTTGTATACAGCTATGACCCGAATGTACTTGAGATAATAGAGATAGAACCGGGAGACATAATA
GTTGACCCGAATCCTGACAAGAGCTTTGATACTGCAGTATATCCTGACAGAAAGATAATAGTATTCCTGTTTGCAGAAGACAGCG
GAACAGGAGCGTATGCAATAACTAAAGACGGAGTATTTGCTACGATAGTAGCGAAAGTAAAAGAAGGAGCACCTAACGGACTCAG
TGTAATCAAATTTGTAGAAGTAGGCGGATTTGCGAACAATGACCTTGTAGAACAGAAGACACAGTTCTTTGACGGTGGAGTAAAT
GTTGGAGATACAACAGAACCTGCAACACCTACAACACCTGTAACAACACCGACAACAACAGATGATCTGGATGCACTCGAGATCA
TCCCAGTTGAGGAGGAGAACCCGGACTTCTGGGACCGCGAGGCAGCCGAGGCCCTGGGTGCCGCCAAGAAGCTGCAGCCTGCACA
GACAGCCGCCAAGAACCTCATCATCTTCCTGGGCGATGGGATGGGGGTGTCTACGGTGACAGCTGCCAGGATCCTAAAAGGGCAG
AAGAAGGACAAACTGGGGCCTGAGTTACCCCTGGCCATGGACCGCTTCCCATATGTGGCTCTGTCCAAGACATACAATGTAGACA
AACATGTGCCAGACAGTGGAGCCACAGCCACGGCCTACCTGTGCGGGGTCAAGGGCAACTTCCAGACCATTGGCTTGAGTGCAGC
CGCCCGCTTTAACCAGTGCAACACGACACGCGGCAACGAGGTCATCTCCGTGATGAATCGGGCCAAGAAAGCAGGGAAGTCAGTG

GGAGTGGTAACCACCACACGAGTGCAGCACGCCTCGCCAGCCGGCACCTACGCCCACACGGTGAACCGCAACTGGTACTCGGACG
CCGACGTGCCTGCCTCGGCCCGCCAGGAGGGGTGCCAGGACATCGCTACGCAGCTCATGTCCAACATGGACATTGACGTGATCCT
AGGTGGAGGCCGAAAGTACATGTTTCGCATGGGAACCCCAGACCCTGAGTACCCAGATGACTACAGCCAAGGTGGGACCAGGCTG
GACGGGAAGAATCTGGTGCAGGAATGGCTGGCGAAGCGCCAGGGTGCCCGGTACGTGTGGAACCGCACTGAGCTCATGCAGGCTT
CCCTGGACCCGTCTGTGACCCATCTCATGGGTGTCTTTGAGCCTGGAGACATGAAATACGAGATCCACCGAGACTCCACACTGGA
CCCCTCCCTGATGGAGATGACAGAGGCTGCCCTGCGCCTGCTGAGCAGGAACCCCGCGGCTTCTTCCTCTTCGTGGAGGGTGGT
CGCATCGACCATGGTCATCATGAAAGCAGGGCTTACGGGCACTGACTGAGACGATCATGTTCGACGACGCCATTGAGAGGGCGG
GCCAGCTCACCAGCGAGGAGGACACGCTGAGCCTCGTCACTGCCGACCACTCCCACGTCTTCTCCTTCGGAGGCTACCCCCTGCG
AGGGAGCTCCATCTTCGGGCTGGCCCCTGGCAAGGCCCGGGACAGGAAGGCCTACACGGTCCTCCTATACGGAAACGGTCCAGGC
TATGTGCTCAAGGACGGCGCCCGGCCGGATGTTACCGAGAGCGAGCGGGAGCCCGAGTATCGGCAGCAGTCAGCAGTGCCCC
TGGACGAAGAGACCCACGCAGGCGAGGACGTGGCGGTGTTCGCGCGCGGCCCGCAGGCGCACCTGGTTCACGGCGTGCAGGAGCA
GACCTTCATAGCGCACGTCATGGCCTTCGCCGCCTGCCTGGAGCCCTACACCGCCTGCGACCTGGCGCCCCCGCCGGCACCACC
CACCATCACCATCACCATTGA (SEQ ID NO.: 14)
```

```
LDDLDAVRIKVDTVNAKPGDTVRIPVRFSGIPSKGIANCDFVYSYDPNVLEIIEIEPGELIVDPNPTKSFDTAVYPDRKMIVFLR
AEDSGTGAYAITEDGVFATIVAKVKSGAPNGLSVIKFVEVGGFANNDLVEQKTQFFDGGVNVGDTTEPATPTTPVTTPTTEDDLD
ALEIIPVEEENPDFWNREAAEALGAAKKLQPAQTAAKNLIIFLGDGMGVSTVTAARILKGQKKDKLGPELPLAMDRFPYVALSKT
YNVDKHVPDSGATATAYLCGVKGNFQTIGLSAAARFNQCNTTRGNEVISVMNRAKKAGKSVGVVTTTRVQHASPAGTYAHTVNRN
WYSDADVPASARQEGCDCIATQLISNMDIDVILGGGKYMFRMGTPDPEYPDDYSQGGTRLDGKNLVQEWLAKRQGARYVWNRTE
LMQASLDPSVTHLMGLFEPGDMKYEIHRDSTLDPSLMEMTEAALRLLSRNPRGFFLFVEGGRIDHGHHESRAYRALTETIMFDDA
IERAGQLTSEEDTLSLVTADHSHVFSFGGYPLRGSSIFGLAPGKARDRKAYTVLLYGNGPGYVLKDGARPDVTESESGSPEYRQQ
SAVPLDEETHAGEDVAVFARGPQAHLVHGVQEQTFIAHVMAFAACLEPYTACDLAPPAGTHHHHHH (SEQ ID NO.: 15)
```

TABLE 8 shows the nucleic acid and amino acid sequences for Mam-pCDM8(Cohesin-Cohesin-SLAML-AP-6xHis) or C17. DNA (entire coding region) and amino acid sequence (the predicted secreted product) is shown below. The cohesin domain is highlighted in yellow and the cohesin and alkaline phosphatase joining sequence is underlined. The highly predicted O-linked glycosylation sites within the linker distal to the cohesin domains are highlighted in red as is a single highly predicted N-linked glycosylation site (NPT). Residues highlighted grey are a C-terminal His tag to facilitate purification via metal affinity chromatography.

TABLE 8

Mam-pCDM8(Cohesin-Cohesin-SLAML-AP-6xHis) or C17.

```
ATGGATCCCAAAGGATCCCTTTCCTGGAGAATACTTCTGTTTCTCTCCCTGGCTTTTGAGTTGAGCTACGGACTCGACGATCTGG
ATGCAGTAAGGATTAAAGTGGACACAGTAAATGCAAAACCGGGAGACACAGTAAGAATACCTGTAAGATTCAGCGGTATACCATC
XAAGGGAATAGCAAACTGTGACTTTGTATACAGCTATGACCCGAATGTACTTGAGATAATAGAGATAAAACCGGGAGAATTGATA
GTTGACCCGAATCCTGACAAGAGCTTTGATACTGCAGTATATCCTGACAGAAAGATAATAGTATTCCTGTTTGCAGAAGACAGCG
GAACAGGAGCGTATGCAATAACTAAAGACGGAGTATTTGCTACGATAGTAGCGAAAGTAAAATCCGGAGCACCTAACGGACTCAG
TGTAATCAAATTTGTAGAAGTAGGCGGATTTGCGAATAATGACCTTGTAGAACAGAAGACACAGTTCTTTGACGGTGGAGTAAAT
GTTGGAGATACAACAGAACCTGCAACACCTACAACACCTGTAACAACACCGACAACAACAGATGATCTGGATGCAGTAAGGATTA
AAGTGGACACAGTAAATGCAAAACCGGGAGACACAGTAAATATACCTGTAAGATTCAGTGGTATACCATCCAAGGGAATAGCAAA
CTGTGACTTTGTATACAGCTATGACCCGAATGTACTTGAGATAATAGAGATAAAACCGGGAGAATTGATAGTTGACCCGAATCCT
ACCAAGAGCTTTGATACTGCAGTATATCCTGACAGAAAGATGATAGTATTCTTGTTTGCGGAAGACAGCGGAACAGGAGCGTATG
CAATAACTAAAGACGGAGTATTTGCTACGATAGTAGCGAAAGTAAAAGAAGGAGCACCTAACGGACTCAGTGTAATCAAATTTGT
AGAAGTAGGCGGATTTGCGAACAATGACCTTGTAGAACAGAAGACACAGTTCTTTGACGGTGGAGTAAATGTTGGAGATACAACA
GAACCTGCAACACCTACAACACCTGTAACAACACCGACAACAACAGATGATCTGGATGCACTCGAGATCATCCCAGTTGAGGAGG
AGAACCCGGACTTCTGGAACCGCGAGGCAGCCGAGGCCCTGGGTGCCGCCAAGAAGCTGCAGCCTGCACAGACAGCCGCCAAGAA
CCTCATCATCTTCCTGGGCGATGGGATGGGGGTGTCTACGGTGACAGCTGCCAGGATCCTAAAAGGGCAGAAGAAGGACAAACTG
GGGCCTGAGTTACCCCTGGCCATGGACCGCTTCCCATATGTGGCTCTGTCAAGACATACAATGTAGACAAACATGTGCCAGACA
GTGGAGCCACAGCCACGGCCTACCTGTGCGGGGTCAAGGGCAACTTCCAGACCATTGGCTTGAGTGCAGCCGCCCGCTTTAACCA
GTGCAACACGACACGCGGCAACGAGGTCATCTCCGTGATGAATCGGGCCAAGAAAGCAGGGAAGTCAGTGGGAGTGGTAACCACC
ACACGAGTGCAGCACGCCTCGCCAGCCGGCACCTACGCCCACACGGTGAACCGCAACTGGTACTCGGACGCCGACGTGCCTGCCT
CGGCCCGCCAGGAGGGGTGCCAGGACATCGCTACGCAGCTCATCTCCAACATGGACATTGACGTGATCCTAGGTGGAGGCCGAAA
GTACATGTTTCGCATGGGAACCCCAGACCCTGAGTACCCAGATGACTACAGCCAAGGTGGGACCAGGCTGGACGGGAAGAATCTG
GTGCAGGAATGGCTGGCGAAGCGCCAGGGTGCCCGGTACGTGTGGAACCGCACTGAGCTCATGCAGGCTTCCCTGGACCCGTCTG
```

TABLE 8-continued

Mam-pCDM8(Cohesin-Cohesin-SLAML-AP-6xHis) or C17.

```
TGACCCATCTCATGGGTCTCTTTGAGCCTGGAGACATGAAATACGAGATCCACCGAGACTCCACACTGGACCCCTCCCTGATGGA
GATGACAGAGGCTGCCCTGCGCTGCTGAGCAGGAACCCCCGCGGCTTCTTCCTCTTCGTGGAGGGTGGTCGCATCGACCATGGT
CATCATGAAAGCAGGGCTTACCGGGCACTGACTGAGACGATCATGTTCGACGACGCCATTGAGAGGGCGGGCCAGCTCACCAGCG
AGGAGGACACGCTGAGCCTCGTCACTGCCGACCACTCCCACGTCTTCTCCTTCGGAGGCTACCCCCTGCGAGGGAGCTCCATCTT
CGGGCTGGCCCCTGGCAAGGCCCGGGACAGGAAGGCCTACACGGTCCTCCTATACGGAAACGGTCCAGGCTATGTGCTCAAGGAC
GGCGCCCGGCCGGATGTTACCGAGAGCGAGAGCGGGAGCCCCGAGTATCGGCAGCAGTCAGCAGTGCCCCTGGACGAAGAGACCC
ACGCAGGCGAGGACGTGGCGGTGTTCGCGCGCGGCCCGCAGGCGCACCTGGTTCACGGCGTGCAGGAGCAGACCTTCATAGCGCA
CGTCATGGCCTTCGCCGCCTGCCTGGAGCCCTACACCGCCTGCGACCTGGCGCCCCCCGCCGGCACCACCCACCATCACCATCAC
CATTGA (SEQ ID NO.: 16)
```

```
LDLDAVRIKVDTVNAKPGDTVRIPVRFSGIPSKGIANCDFVYSYDPNVLEIIEIKPGELIVDPNPDKSFDTAVYPDRKIIVFLPA
EDSGTGAYAITKDGVFATIVAKVKSGAPNGLSVIKFVEVGGFANNDLVEQKTQFFDGGVNYGDTTEPATPTTPVTTPTTTDDLDA
VRIKVDTVNAKPGDTVNIPVRFSGIPSKGIANCDFVYSYDPNVLEIIEIKPGELIVDPNPIKSFDTAVYPDRKMIVFLFAEDSGT
GAYAIIKDGVFATIVAKVKEGAPNGLSVIKFVEVGGFANNDLVEQKTQFFDGGVNYGDTTEPATPTTPVTTPTTTDDLDALEIIP
VEEENPDFWNREAAEALGAAKKLQPAQTAAKNLIIFLGDGMGVSTVTAARILKGQKKDKLGPELPLAMDRFPYVALSKTYNVDKH
VPDSGATATAYLCGVKGNFQTIGLSAAARFNQCNTTRGNEVISVMNRAKKAGKSVGVVTTTRVQHASPAGTYAHTVNRNWYSDAD
VPASARQEGCQDIATQLISNMDIDVILGGGRKYMFRMGTPDPEYPDDYSQGGTRLDGKNLVQEWLAKRQGARYVWNRTELMQASL
DPSVTHLMGLFEPGDMKYEIHRDSTLDPSLMEMTEAALRLLSRNPRGFFLFVEGGRIDHGHHESRAYRALTETIMFDDAIERAGQ
LTSEEDTLSLVTADHSVVSFGGYPLRGSSIFGLAPGKARDRKAYTVLLYGNGPGYVLKDGARPDVTESESGSPEYRQQSAVPLD
EETHAGEDVAVFARGPQAHLVHGVQEQTFIAHVMAFAACLEPYTACDLAPPAGTTHHHHHH (SEQ ID NO.: 17)
```

TABLE 9 shows the nucleic acid and amino acid sequences for Mam-pCDM8(SLAML-Cohesin-hPSA) or C149. DNA (entire coding region) and amino acid sequence (the predicted secreted product) is shown below. The cohesin domain is highlighted in yellow and the cohesin and hPSA joining sequence is underlined. The highly predicted O-linked glycosylation sites within the linker distal to the cohesin domains and a single highly predicted N-linked glycosylation site within the cohesin domain are highlighted in red.

TABLE 10 shows the nucleic acid and amino acid sequences for Mam-pCDM8(SLAML-Cohesin-FluHA5-1-6×His) or C24. DNA (entire coding region) and amino acid sequence (the predicted secreted product) is shown below. The cohesin domain is highlighted in yellow and the cohesin and Flu HA5-1 joining sequence is underlined. The highly predicted O-linked glycosylation sites within the linker distal to the cohesin domains and a single highly predicted N-linked glycosylation site within the cohesin domain are highlighted in red. Residues highlighted grey are a C-terminal His tag to facilitate purification via metal affinity chromatography.

TABLE 9

Mam-pCDM8(SLAML-Cohesin-hPSA) or C149.

```
ATGGATCCCAAAGGATCCCTTTCCTGGAGAATACTTCTGTTTCTCTCCCTGGCTTTTGAGTTGAGCTACGGACTCGACGATCTGG
ATGCAGTAAGGATTAAAGTGGACACAGTAAATGCAAAACCGGGAGACACAGTAAGAATACCTGTAAGATTCAGCGGTATACCATC
CAAGGGAATAGCAAACTGTGACTTTGTATACAGCTATGACCCGAATGTACTTGAGATAATAGAGATAGAACCGGGACACATAATA
GTTGACCCGAATCCTGACAAGAGCTTTGATACTGCAGTATATCCTGACAGAAAGATAATAGTATTCCTGTTTGCAGAAGACAGCG
GAACAGGAGCGTATGCAATAACTAAAGACGGAGTATTTGCTACGATAGTAGCGAAAGTAAAAGAAGGAGCAGGTAACGGACTCAG
TGTAATCAAATTTGTAGAAGTAGGCGGATTTGCGAACAATGACCTTGTAGAACAGAAGACACAGTTCTTTGACGGTGGAGTAAAT
GTTGGAGATACAACAGAACCTGCAACACCTACAACACCTGTAACAACACCGACAACAACAGATGATCGGATGCACTCGAGGCGC
CCCTCATCCTGTCTCGGATTCTGGGAGGCTGGGAGTGCGAGAAGCATTCCCAACCCTGGCAGGTGCTTGTGGCCTCTCGTGGCAG
GGCAGTCTGCGGCGGTGTTCTGGTGCACCCCCAGTGGGTCCTCACAGCTGCCCACTGCATCAGGAACAAAAGCGTGCTCTTGCTG
GGTCGGCACAGCCTGTTTCATCCTGAAGCACAGGCCAGGTATTTCAGGTCAGCCACAGCTTCCCACACCCGCTCTACGATATGA
GCCTCCTGAAGAATCGATTCCTCAGGCCAGGTGATGACTCCAGCCACGACCTCATGCTGCTCCCTGTCAGAGCCTGCCGAGCT
CACGGATGCTGTGAAGGTCATGGACCTGCCCACCCAGGAGCCAGCACTGGGGACCACCTGCTACGCCTCAGGCTGGGGCAGCATT
GAACCAGAGGAGTTCTTGACCCCAAAGAAACTTCAGTGTGTGGACCTCCATGTTATTTCCAATGACGTGTGCGCGCAAGTTCACC
CTCAGAAGGTGACCAAGTTCATGCTGTGTGCTGGACGCTGGACAGGGGCAAAAGCACCTGCTCGGGTGATTCTGGGGGCCCACT
TGTCTGTAATGGTGTGCTTCAAGGTATCACGTCATGGGGCAGTGAACCATGTGCCCTGCCCGAAAGGCCTTCCCTGTACACCAAG
GTGGTGCATTACCGGAAGTGGATCAAGGACACCATCGTGGCCAACCCCTGA (SEQ ID NO.: 18)
```

```
LDDLDAVRIKVDTVNAKPGDTVRIPVRFSGIPSKGIANCDFVYSYDPNVLEIIEIEPGELIVDPNPIKSFDTAVYPDRKMIVFLP
AEDSGTGAIAITEDGVFATIVAKVKSGAPNGLSVIKFVEVGGFANNDLVEQKTQFFDGGVNYSDTTEPATPTTPVTTPTTTDDLD
ALEAPLILSRIVGGWECEKHSQPWQVLVASRGRAVCGGVLVHPQWVLTAAHCIRNKSVILLGRHSLFHPEDTGQVFQVSHSFPHP
LYDMSLLKNRFLRPGDDSSHDLMLLRLSEPAELTDAVKVMDLPTQEPALGTTCYASGWGSIEPEEFLTPKKLQCVDLHVISNDVC
AQVHPQKVTKFMLCAGRWTGGKSTCSGDSGGPLVCNGVLQGITSWGSEPCALPERPSLYTKVVHYRKWIKDTIVANP (SEQ ID
NO.: 19)
```

TABLE 10

Mam-pCDM8(SLAML-Cohesin-FluHA5-1-6xHis) or C24.

```
ATGGATCCCAAAGGATCCCTTTCCTGGAGAATACTTCTGTTTCTCTCCCTGGCTTTTGAGTTGAGCTACGGACTCGACGATCTGG
ATGCAGTAAGGATTAAAGTGGACACAGTAAATGCAAAACCGGGAGACACAGTAAGAATACCTGTAAGATTCAGCGGTATACCATC
CAAGGGAATAGCAAACTGTGACTTTGTATACAGCTATGACCCGAATGTACTTGAGATAATAGAGATAGAACCGGGAGACATAATA
GTTGACCCGAATCCTGACAAGAGCTTTGATACTGCAGTATATCCTGACAGAAAGATAATAGTATTCCTGTTTGCAGAAGACAGCG
GAACAGGAGCGTATGCAATAACTAAAGACGGAGTATTTGCTACGATAGTAGCGAAAGTAAAAGAAGAGGCACCTAACGGACTCAG
TGTAATCAAATTTGTAGAAGTAGGCGGATTTGCGAACAATGACCTTGTAGAACAGAAGACACAGTTCTTTGACGGTGGAGTAAAT
GTTGGAGATACAACAGAACCTGCAACACCTACAACACCTGTAACAACACCGACAACAACAGATGATCTGGATGCACTCGAGGATC
AGATTTGCATTGGTTACCATGCAAACAACTCGACAGAGCAGGTTGACACAATAATGGAAAAGAACGTTACTGTTACACATGCCCA
AGACATACTGGAAAAGAAACACAACGGGAAGCTCTGCGATCTAGATGGAGTGAAGCCTCTAATTTTGAGAGATTGTAGCGTAGCT
GGATGGCTCCTCGGAAACCCAATGTGTGACGAATTCATCAATGTGCCGGAATGGTCTTACATAGTGGAGAAGGCCAATCCAGTCA
ATGACCTCTGTTACCCAGGGGATTTCAATGACTATGAAAAATTGAAACACCTATTGAGCAGAATAAACCATTTTGAGAAAATTCA
GATCATCCCCAAAAGTTCTTGGTCCAGTCATGAAGCCTCATTAGGGGTGAGCTCAGCATGTCCATACCAGGGAAAGTCCTCCTTT
TTCAGAAATGTGGTATGGCTTATCAAAAAGAACAGTACATACCCAACAATAAAGAGGAGCTACAATAATACCAACCAAGAAGATC
TTTTGGTACTGTGGGGGATTCACCATCCTAATGATGCGGCAGAAGCAGACAAAGCTCTATCAAAACCAACCACCTATATTTCCGT
TTTTGGTACTGTGGGGGATTCACCATCCTAATGATGCGGCAGAGCAGACAAAGCTCTATCAAAACCCAACCACCTATATTTCCGT
TGGGACATCAACACTAAACCAGAGATTGGTACCAAGAATAGCTACTAGATCCAAAGTAAACGGGCAAAGTGGAAGGATGGAGTTC
TTCTGGACAATTTTAAAGCCCGAATGATGCAATCAACTTCGAGAGTAATGGAAATTTCATTGCTCCAGAATATGCATACAAAATTG
TCAAGAAAGGGGACTCAACAATTATGAAAAGTGAATTGGAATATGGTAACTGCAACACCAAGTGTCAAACTCCAATGGGGGCGAT
AAACTCTAGCATGCCATTCCACAATATACACCCTCTCACCATTGGGGAATGCCCCAAATATGTGAAATCAAACAGATTAGTCCTT
GCGCACCATCACCATCACCATTGA (SEQ ID NO.: 20)
```

```
LDDLDAVRIKVDTVNAKPGDTVRIPVRFSGIPSKGIANCDFVYSYDPNVLEIIEIEPGELIVDPNPTKSFDTAVYPDRKMIVFLR
AEDSGTGAYAITEDGVFATIVAKVKSGAPNGLSVIKFVEVGGFANNDLVEQKTQFFDGGVNVGDTEEPATPTTPVTPTTDDLD
ALEDQICIGYHANNSTEQVDTIMEKNVTVTHAQDILEKKHNGKLCDLDGVKPLILRDCSVAGWLLGNPMCDEFINVPEWSYIVEK
ANPVNDLCYPGDFNDYEKLKHLLSRINHFEKIQIIPKSSWSSHEASLGVSSACPYQGKSSFFRNVVWLIKKNSTYPTIKRSYNNT
NQEDLLVLWGIHHPNDAAEQTKLYQNPTTYISVGTSTLNQRLVPRIATRSKVNGQSGRMEFFWTILKPNDAINFESNGNFIAPEY
AYKIVKKGDSTIMKSELEYGNCNTKCQTPMGAINSSMPFHNIHPLTIGECPKYVKSNRLVLAHHHHHH. (SEQ ID
NO.: 21)
```

Similar to the above mentioned rAb.doc constructs, the invention embodies the efficient secretion from mammalian cells of functional cohesin fusion proteins (called herein coh.fusions). It was not obvious that cohesin domains could be so successfully secreted while retaining dockerin-binding function. FIG. 5 demonstrates that supernatant containing secreted coh.alkaline phosphatase (coh.AP) binds specifically to a rAb.doc protein immobilized on a plastic surface.

Figure 7A:
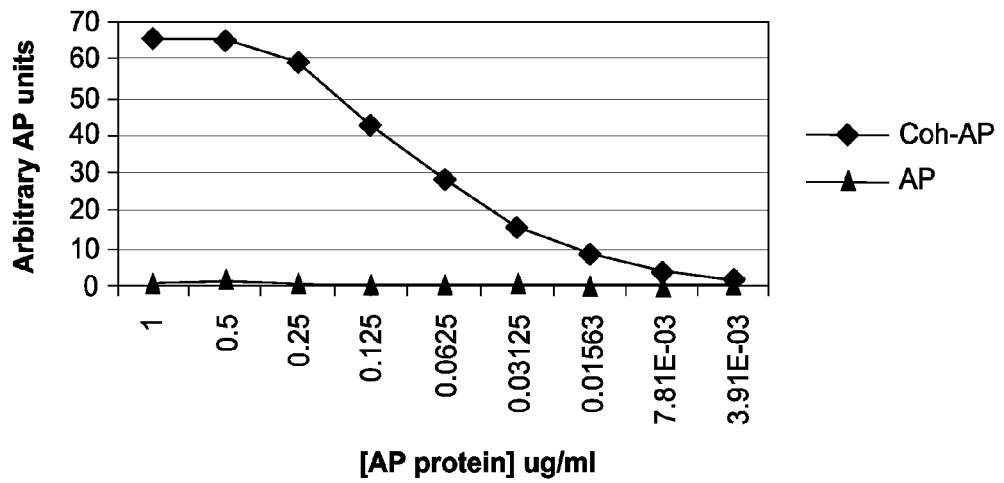
FIGS. 7A and 7B show that the secreted coh.alkaline phosphatase (coh.AP) but not AP binds efficiently and specifically to rAb.Doc immobilized on plastic.
Figure 7B:
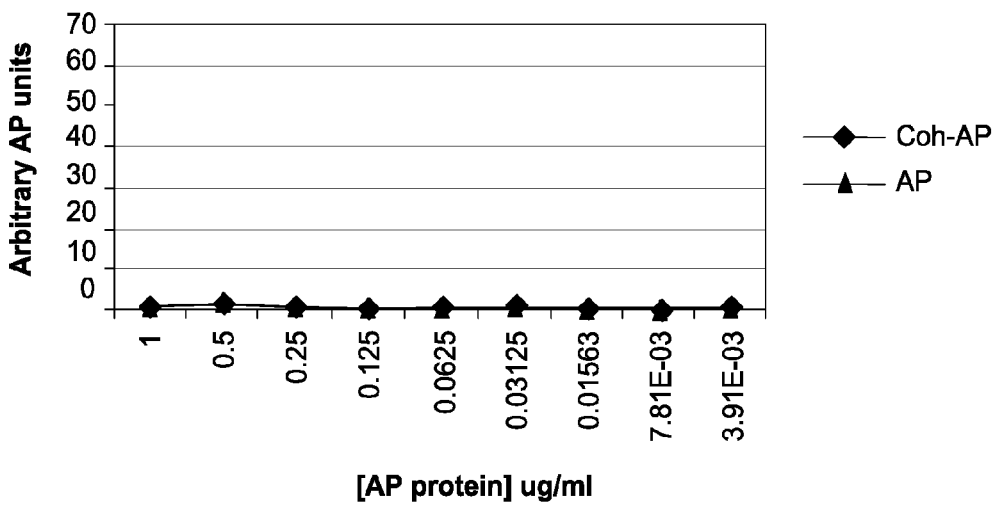

FIGS. 7A and 7B show that the Expression plasmids encoding secreted alkaline phosphatase (AP) or coh.AP directed secretion of functional proteins from transfected 293F cells. After 3 days of culture supernatants were harvested and tested for their ability to bind 0.25 ug of either rAb.doc (top panel) or rAb (lower panel) bound to a 96 well micro-titre plate. After 1 hr of incubation the plates were washed and developed with a chromogenic AP substrate.

The invention embodies the application of assembly of specific protein complexes based on the cohesin.dockerin interaction. Specific antibody.antigen complexes can also be assembled using the established interaction of protein A or protein G IgFc binding domains. The invention embodies unique properties of the cohesin.dockerin interaction that result in greatly superior complex formation compared to the e.g., protein G interaction with IgG. In FIGS. 6 and 7 the interaction of a cohesin.AP (called Coh.AP) protein is shown to be specific for a rAb.Doc protein.

Figure 8A:
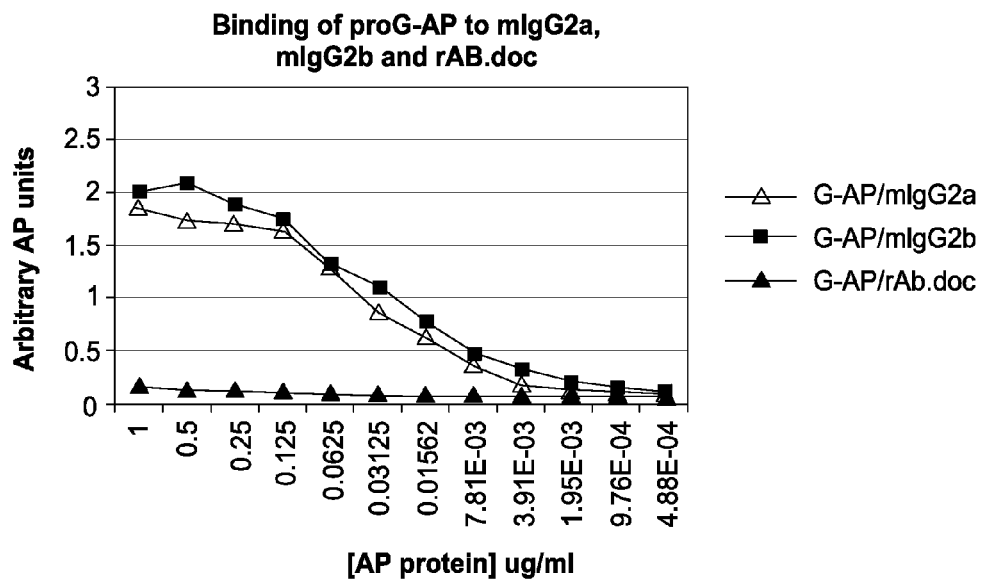
FIGS. 8A and 8B shows various dilutions of a supernatant containing secreted G.AP bound to immobilized mIgG2a and mIgG2b, but not rAb.doc, while coh.AP bound rAb.doc specifically.
Figure 8B:
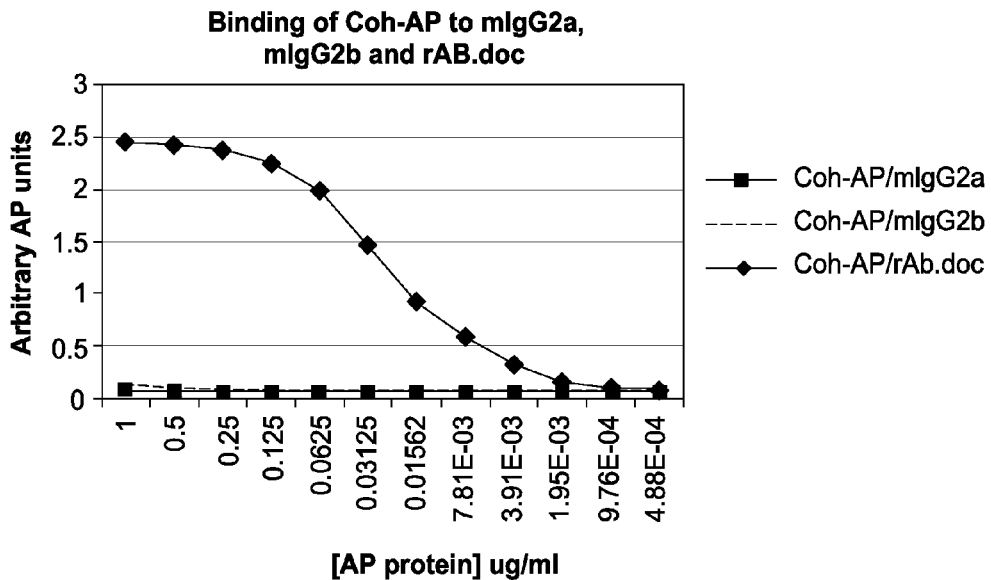

FIGS. 8A and 8B shows various dilutions of a supernatant containing secreted G.AP were incubated for 1 hr in micro-titre wells containing 0.25 ug of immobilized mIgG2a, mIgG2b, or a mIgG2b-based rAb.doc. After washing the bound AP activity was developed using chromogenic AP substrate. The proG.AP did not bind to the rAb.doc since it was an isotype variant of mIgG2b that did not interact with the particular protein G domain used in the proG.AP construct.

FIG. 8B shows an identical study, but employing dilutions of a supernatant containing secreted Coh.AP. Coh.AP binds only to rAb.doc, again demonstrating the specificity of the coh.doc interaction.

Figure 9:
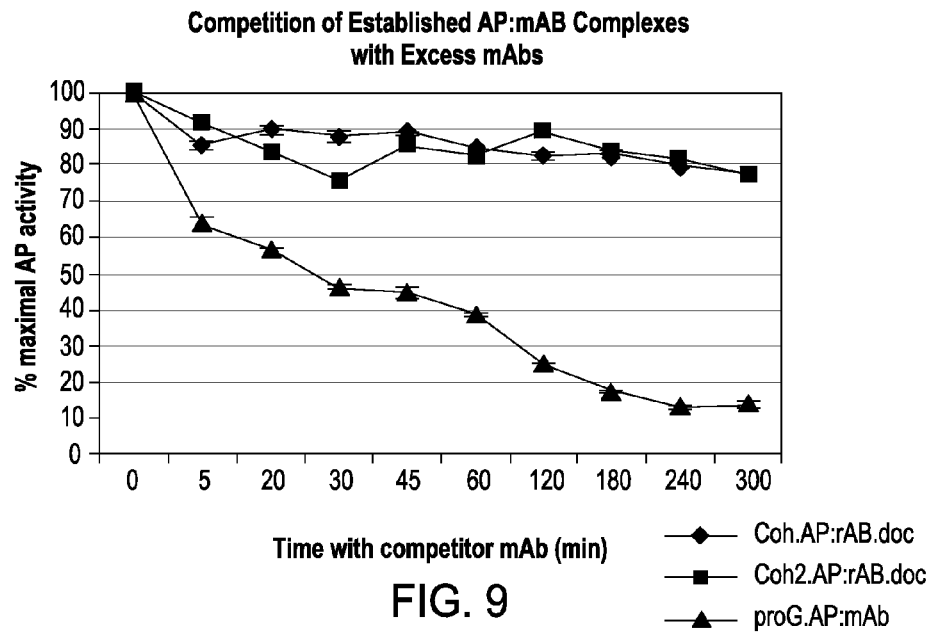
FIG. 9 shows the differential stability of complexes between a fixed amount of proG.AP or coh.AP or coh2.AP (0.1 ug) and immobilized mIgG2b or rAb.doc (0.25 ug) assembled by incubation for 1 hr in a micro-titre plate.

FIG. 9 demonstrates the vastly superior stability of preassembled complexes based on coh.doc interaction compared to proG.IgGFc interaction. FIG. 9 shows the formation of complexes between a fixed amount of proG.AP or coh.AP or coh2.AP (0.1 ug) and immobilized mIgG2b or rAb.doc (0.25 ug) were assembled by incubation for 1 hr in a micro-titre plate. At various times a 20-fold excess of soluble mIgG2b or rAb.doc were added and incubation continued for various times. Plates were then washed and bound AP activity accessed by addition of chromogenic AP substrate.

Figure 10:
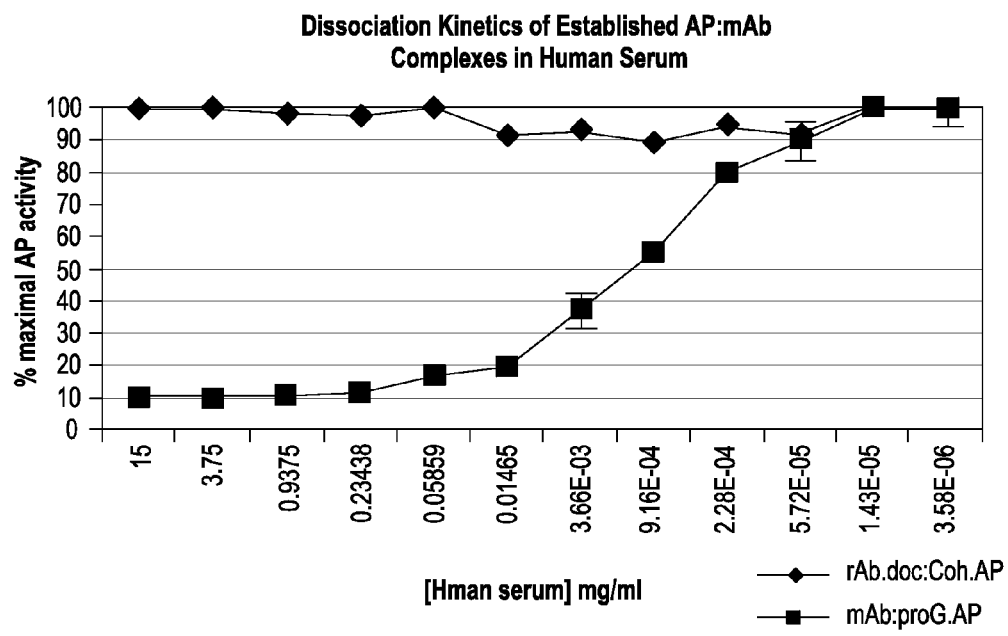
FIG. 10 shows the differential stability in human serum of complexes between a fixed amount of proG.AP or coh.AP (0.1 ug) and immobilized mIgG2b or rAb.doc (0.25 ug) were assembled by incubation for 1 hr in a micro-titre plate.

This example shows the use of such coh.doc complexes in settings containing serum (e.g., tissue culture media and in vivo administration). FIG. 10 demonstrates the vast superiority of coh.doc complexes compared to proG.IgGFc complexes in such a setting. Under the conditions used, ~15 ug/ml Ig was sufficient to completely displace bound proG.AP, while the coh.AP remained stably bound to rAb.doc even in the presence of pure serum (15 mg/ml Ig)

FIG. 10 shows the formation of complexes between a fixed amount of proG.AP or coh.AP (0.1 ug) and immobilized mIgG2b or rAb.doc (0.25 ug) were assembled by incubation for 1 hr in a micro-titre plate. Various dilutions of human serum were added and incubation continued for 4 hrs. Plates were then washed and bound AP activity accessed by addition of chromogenic AP substrate.

The invention also embodies a particular utility of the coh.doc interaction that permits a production process that ensures complete complex formation and that can be concomitant with a purification process for the coh.fusion protein entity. This invention is exemplified in FIGS. 11 and 12, which illustrate this process via sequential capture of rAb.doc from culture supernatant by protein G affinity chromatography, followed by capture of coh.antigen from culture supernatant by the proteinG:rAb.doc column. Elution with low pH then releases pure rAb.doc:coh.antigen. If there is an excess of coh.antigen over rAb.doc, them full and complete complex should result. A related embodiment of this invention would be application to the protein G captured rAb.doc of excess pure or partially purified coh.fusion protein.

Figure 11:
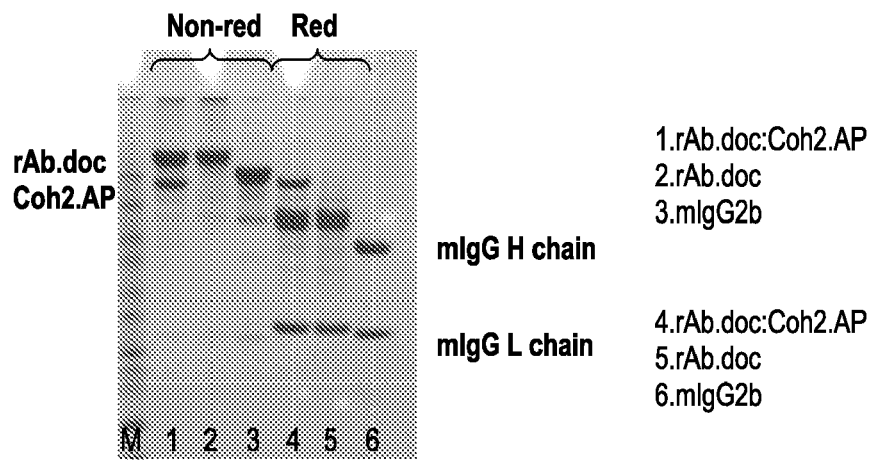
FIG. 11 is a gel that shows the reduced vs. non-reduced SDS.PAGE analysis of rAb.doc:Coh2.AP complexes produced by sequential application of rAb.doc supernatant and coh.AP supernatant to the same protein G affinity column.

FIG. 11 shows a gel of reduced vs. non-reduced SDS.PAGE analysis of rAb.doc:Coh2.AP complexes produced by sequential application of rAb.doc supernatant and coh.AP supernatant to the same protein G affinity column. Lanes 2 and 4 show that Coh2.AP co-purifies with rAb.doc.

Figure 12:
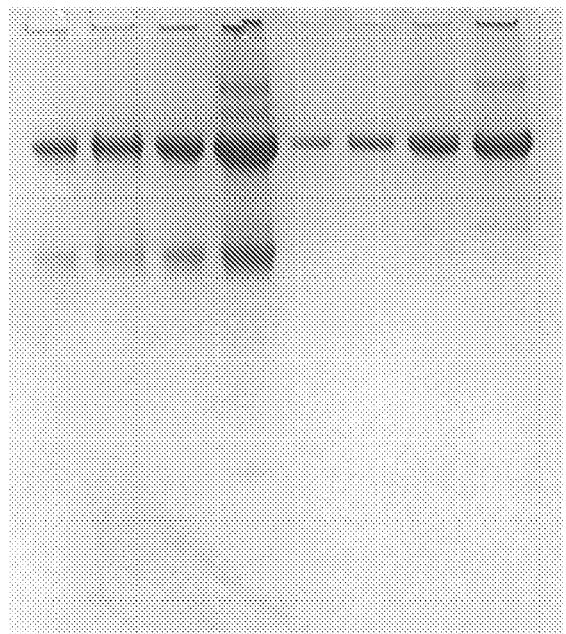
FIG. 12 is a non-reduced SDS.PAGE analysis of rAb.doc:Coh.Flu HA5-1 complexes produced by sequential application of rAb.doc supernatant and coh.Flu HA5-1 supernatant to the same protein G affinity column.

FIG. 12 is a non-reduced SDS.PAGE analysis of rAb.doc:Coh.Flu HA5-1 complexes produced by sequential application of rAb.doc supernatant and coh.Flu HA5-1 supernatant to the same protein G affinity column. Lanes 1 to 4 left to right show that Coh.Flu HA5-1 co-purifies with rAb.doc.

A well described feature of cohesin domains is their compatibility with the standard *E. coli* bacterial expression system. The invention embodies the novel use of expression of dockerin fusion proteins in mammalian secretion systems, and it also encompasses the formation of coh.doc complexes where the different components (i.e., coh and doc) are expressed in different systems. This is a great advantage since it affords the possibility of using the most favorable expression system for each component. For example, coh.Flu M1 expression constructs failed to efficiently direct the synthesis of secreted product from transfected mammalian cells. However, coh.Flu M1 was very efficiently expressed as a soluble protein in *E. coli*. Table 6 shows the sequence of the coh.Flu M1 used in this example.

TABLE 11 shows the nucleic and amino acid sequence for *E coli*-pET28(Cohesin-FluM1-6×His) or C32 is shown below. In the amino acid sequence the cohesin domain is highlighted in yellow and the point of fusion between cohesion and influenza A M1 protein is underlined. Residues highlighted grey are a C-terminal His tag to facilitate purification via metal affinity chromatography.

The invention embodies the use of the dockerin.cohesin interaction to assemble ordered and specific complexes for various therapeutic or vaccination purposes. An example is the use of rAb.doc with binding specificity to an internalizing human Dendritic Cell (DC) receptor complexed with coh.Flu M1 protein. FIG. 11 demonstrates this utility by an in vitro study. DC cultured with anti-DC_rAb.doc:coh.Flu M1, then co-cultured with autologous T cells, directed the expansion of T cells with specific memory of Flu M1. Equivalent doses of coh.Flu M1 alone had no such effect. The study shows at least a 50-fold enhancement of Flu M1-specific T cell expansion via the anti-DC_rAb.doc:coh.Flu M1 compared to coh.Flu M1 alone.

Figure 13:
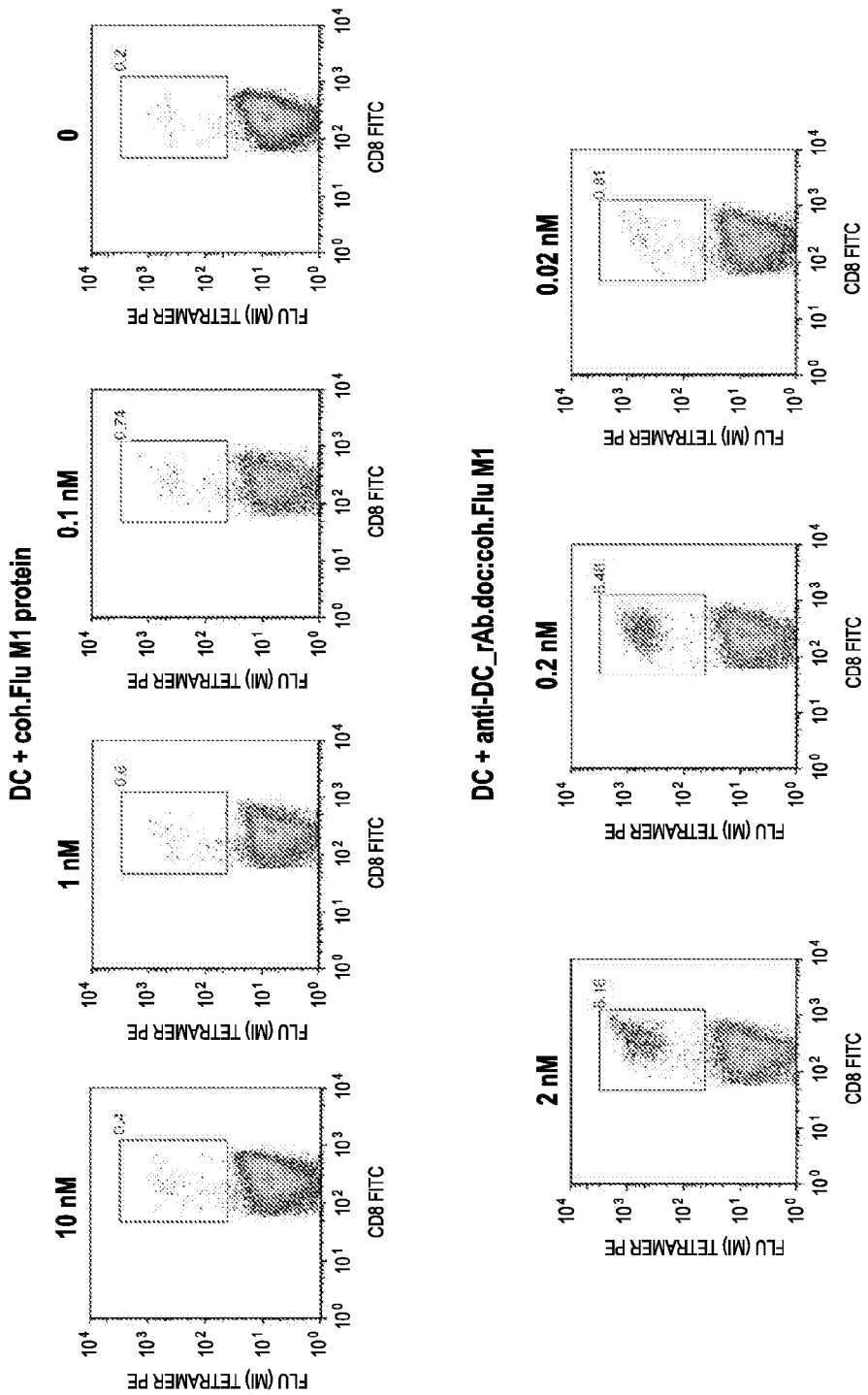
FIG. 13 shows that anti-DC_rAb.doc:coh.Flu M1 complex formed by mixing the individual purified components was effective in vitro in expanding Flu M1-specific T cells.

FIG. 13 shows that functional anti-DC_rAb.doc:coh.Flu M1 complex was formed by mixing the individual purified components. Various amounts of the complex, or coh.Flu M1 alone, were incubated in culture medium with 5E4 human DC (from a HLA201 donor) and 10E5 autologous T cells. After 24 hr, the DC were activated with CD40L and incubation was continued for an additional 9 days. Cells were harvested and stained with a PE-labeled Flu M1 peptide GILGFVFTL (SEQ ID NO.:24) HLA-A2 tetramer and analyzed for the frequency of antigen-specific CD8+ cells.

Figure 14:
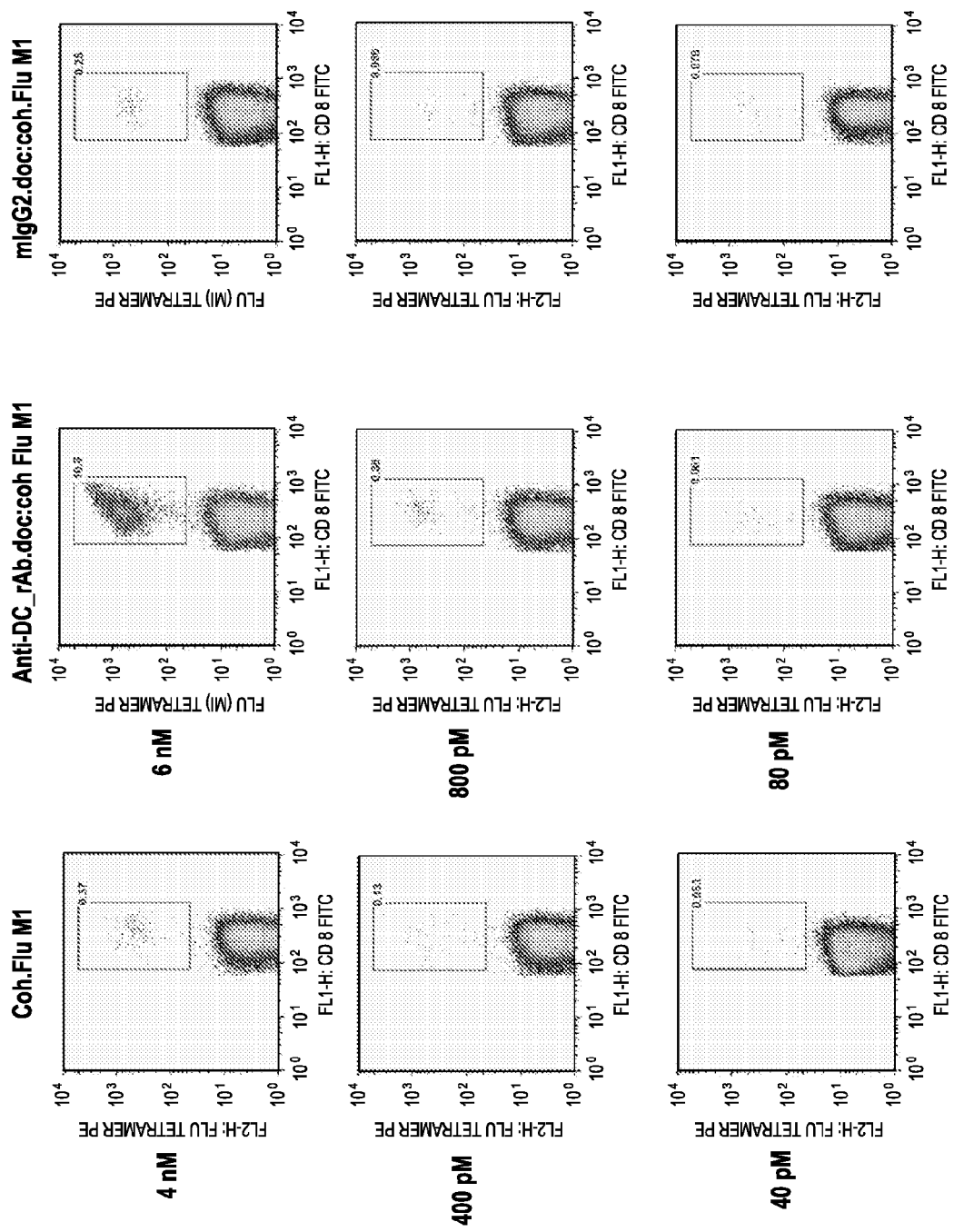
FIG. 14 shows that Anti-DC_rAb.doc:coh.Flu M1 but not mIgG2b.doc:coh.Flu M1 complexes formed by mixing the individual purified components was effective in vitro in expanding Flu M1-specific T cells.

FIG. 14 shows a similar example incorporating the additional control of coh.Flu M1 complexed to an isotype-matched mAb.doc with no binding to the human DC. FIG. 12 shows that Anti-DC_rAb directly linked via an H chain fusion to a peptide fragment spanning the Flu M1 GILGFVFTL epitope is also effective in eliciting DC targeted antigen delivery resulting in expansion of Flu M1-specific T cells. However the Anti-DC_rAb.Flu M1 PEP entity was secreted very poorly from mammalian cells, likely precluding production of such a vaccine. This problem illustrates the embodiment of the invention that allows production issues to be solved by employing expression systems appropriate for the (in this case) vaccine antigen.

TABLE 11

*E coli*-pET28(Cohesin-FluM1-6×His) or C32.

```
ATGGATCTGGATGCAGTAAGGATTAAAGTGGACACAGTAAATGCAAAACCGGGAGACACAGTAAATATACCTGTAAGATTCAGTG
GTATACCATCCAAGGGAATAGCAAACTGTGACTTTGTATACAGCTATGACCCGAATGTACTTGAGATAATAGAGATAAAACCGGG
AGAATTGATAGTTGACCCGAATCCTACCAAGAGCTTTGATACTGCAGTATATCCTGACAGAAAGATGATAGTATTCCTGTTTGCG
GAAGACAGCGGAACAGGAGCGTATGCAATAACTAAAGACGGAGTATTTGCTACGATAGTAGCGAAAGTAAAAGAAGGAGCACCTA
ACGGGCTCAGTGTAATCAAATTTGTAGAAGTAGGCGGATTTGCAAACAATGACCTTGTAGAACAGAAGACACAGTTCTTTGACGG
TGGAGTAAATGTTGGAGATACAACAGAACCTGCAACACCTACAACACCTGTAACAACACCGACAACAACAGATGATCTGGATGCA
GCTAGCCTTCTAACCGAGGTCGAAACGTACGTTCTCTCTATCATCCCGTCAGGCCCCCTCAAAGCCGAGATCGCACAGAGACTTG
AAGATGTCTTTGCAGGGAAGAACACCGATCTTGAGGTTCTCATGGAATGGCTAAAGACAAGACCAATCCTGTCACCTCTGACTAA
GGGGATTTTAGGATTTGTGTTCACGCTCACCGTGCCCAGTGAGCGGGGACTGCAGCGTAGACGCTTTGTCCAAAATGCTCTTAAT
GGGAACGGACATCCAAATAACATGGACAAAGCAGTTAAACTGTATAGGAAGCTTAAGAGGGAGATAACATTCCATGGGCCAAAG
AAATAGCACTCAGTTATTCTGCTGGTGCACTTGCCAGTTGTATGGGCCTCATATACAACAGGATGGGGGCTGTGACCACTGAAGT
GGCATTTGGCCTGGTATGCGCAACCTGTGAACAGATTGCTGACTCCCAGCATCGGTCTCATAGGCAAATGGTGACAACAACCAAT
CCACTAATCAGACATGAGAACAGAATGGTTCTAGCCAGCACTACAGCTAAGGCTATGGAGCAAATGGCTGGATCGAGTGAGCAAG
CAGCAGAGGCCATGGATATTGCTAGTCAGGCCAGGCAAATGGTGCAGGCGATGAGAACCATTGGGACTCATCCTAGCTCCAGTGC
TGGTCTAAAAGATGATCTTCTTGAAAATTTGCAGGCTTACCAGAAACGGATGGGGGTGCAGATGCAGCGATTCAAGCTCGAGCAC
CACCACCACCACCACTGA (SEQ ID NO.: 22)
```

MDLDAVRIKVDTVNAKPGDTVNIPVRFSGIPSKGIANCDFVYSDPNVLEIIEIKPGELIVDPNPTKSFDTAVYPDRKMIVFLFA
EDSGTGAYAITKDGVFATIVAKVKEGAPNGLSVIKFVEVGGFANNDLVEQKTQFFDGGVNVGDTTEPATPTPVTTPTTTDDLDA
ASLLTEVETYVLSIIPSGPLKAEIAQRLEDVFAGKNTDLEVLMEWLKTRPILSPLTKGILGFVFTLTVPSERGLQRRRFVQNALN
GNGDPNNMDKAVKLYRKLKREITFHGAKEIALSYSAGALASCMGLIYNRMGAVTTEVAFGLVCATCEQIADSQHRSHRQMVTTTN
PLIRHENRMVLASTTAKAMEQMAGSSEQAAEAMDIASQARQMVQAMRTIGTHPSSSAGLKDDLLENLQAYQKRMGVQMRFKLEH
HHHHH (SEQ ID NO.: 23)

FIG. 14 shows that Anti-DC_rAb.doc:coh.Flu M1 or mIgG2b.doc:coh.Flu M1 complexes were formed by mixing the individual purified components. Various amounts of the complexes, or coh.Flu M1 alone, were incubated in culture medium with 5E4 human DC (from a HLA201 donor) and 10E5 autologous T cells. After 24 hr, the DC were activated with CD40L and incubation was continued for an additional 9 days. Cells were harvested and stained with a PE-labeled Flu M1 peptide GILGFVFTL (SEQ ID NO.:24) HLA-A2 tetramer and analyzed for the frequency of antigen-specific CD8+ cells. Concentrations for mIgG2.doc complexes were the same as those for Anti-DC_rAb complexes.

TABLE 12 shows the amino acid sequence of the melanoma-associated antigen gp100. Well known HLA-A201-restricted dominant peptides are shaded and detailed below the sequence. Peptide sequences labeled M are variants with enhanced affinity for HLA-A201. C180 is an *E. coli* expression construct that encodes the sequence shown below in which the cohesin domain is shaded blue and the gp100 peptide is shaded grey. Underlined residues bounding the peptide are native to gp100. C-terminal His tags are to facilitate purification via metal affinity chromatography.

Shown below is the gp100 sequence and the associated peptides referred to above.

```
MDLVLKRCLLHLAVIGALLAVGATKVPRNQDWLGVSRQLRTKAWNRQLYPEWTEAQRLDCWRGGQVSLKVSNDGPTLIGANASFSI
ALNFPGSQKVLPDGQVIWVNNTIINGSQVWGGQPVYPQETDDACIFPDGGPCPSGSWSQKRSFVYVWKTWGQYWQVLGGPVSGLSI
GTGRAMLGTHTMEVTVYHRRGSRSYVPLAHSSSAFTITDQVPFSVSVSQLRALDGGNKHFLRNQPLTFALQLHDPSGYLAEADLSY
TWDFGDSSGTLISRALVVTHTYLEPGPVTAQVVLQAAIPLTSCGSSPVPGTTDGHRPTAEAPNTTAGQVPTTEVVGTTPGQAPTAE
PSGTTSVQVPTTEVISTAPVQMPTAESTGMTPEKVPVSEVMGTTLAEMSTPEATGMTPAEVSIVVLSGTTAAQVTTTEWVETTARE
LPIPEPEGPDASSIMSTESITGSLGPLLDGTATLRLVKRQVPLDCVLYRYGSFSVTLDIVQGIESAEILQAVPSGEGDAFELTVSC
QGGLPKEACMEISSPGCQPPAQRLCQPVLPSPACQLVLHQILKGGSGTYCLNVSLADTNSLAVVSTQLIMPGQEAGLGQVPLIVGI
LLVLMAVVLASLIYRRRLMKQDFSVPQLPHSSSWLRLPRIFCSCPIGENSPLLSGQQV       (SEQ ID NO.: 25)
```

Figure 15:
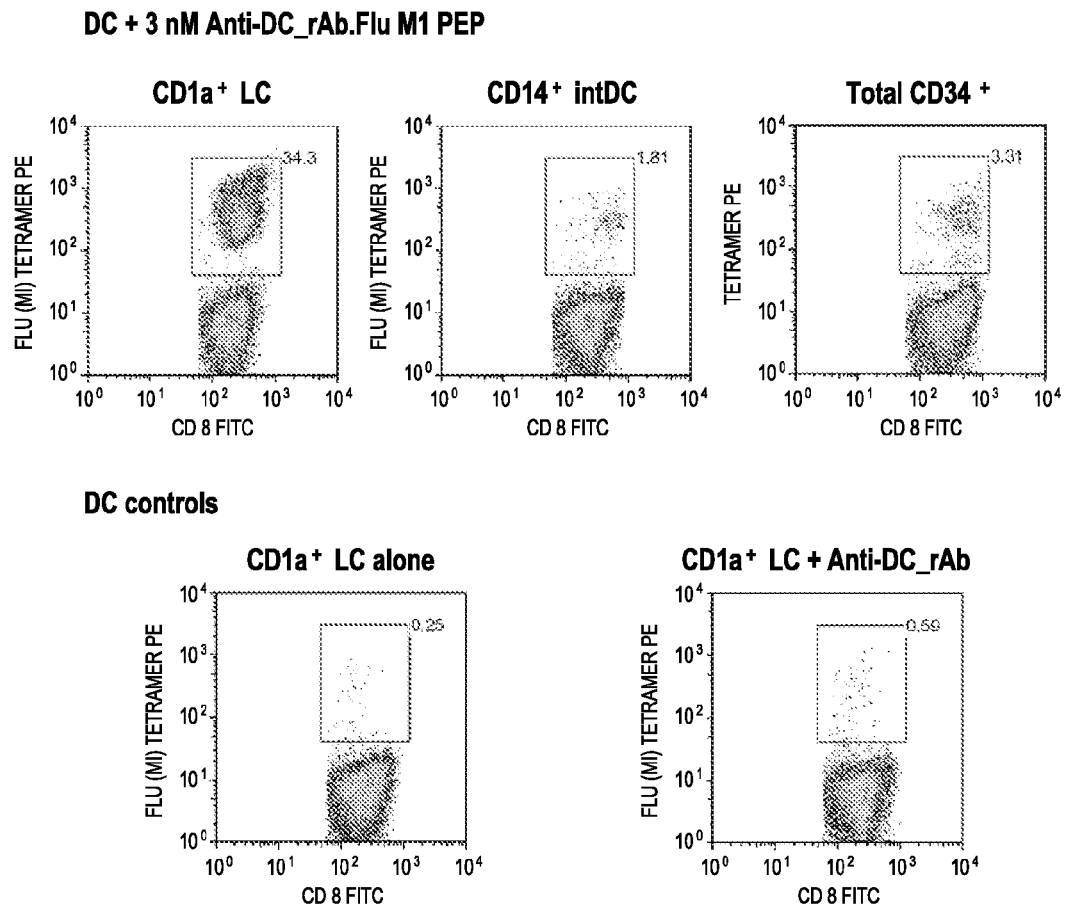
FIG. 15 shows CD34+ human DC were sorted into CD1a+ and CD14+ subtypes and cultured with and without 3 nM Anti-DC_rAb.Flu M1 PEP or Anti-DC_rAb.

FIG. 15 shows CD34+ human DC were sorted into CD1a+ and CD14+ subtypes and cultured with and without 3 nM Anti-DC_rAb.Flu M1 PEP or Anti-DC_rAb. Autologous T cells were added after 1 day and culture continued for a further 8 days. Analysis was as described above. The CD1a+ cells were very efficient in expanding Flu M1-specific CD8+ cells only with Anti-DC_rAb.Flu M1 PEP treatment.

Figure 16:
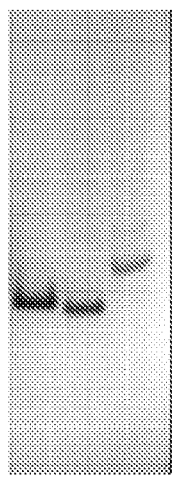
FIG. 16 shows *E. coli* harboring expression plasmids directing the synthesis of coh.pep proteins were grown and induced for specific protein production. Cells were harvested and broken by sonication.
Figure 17:
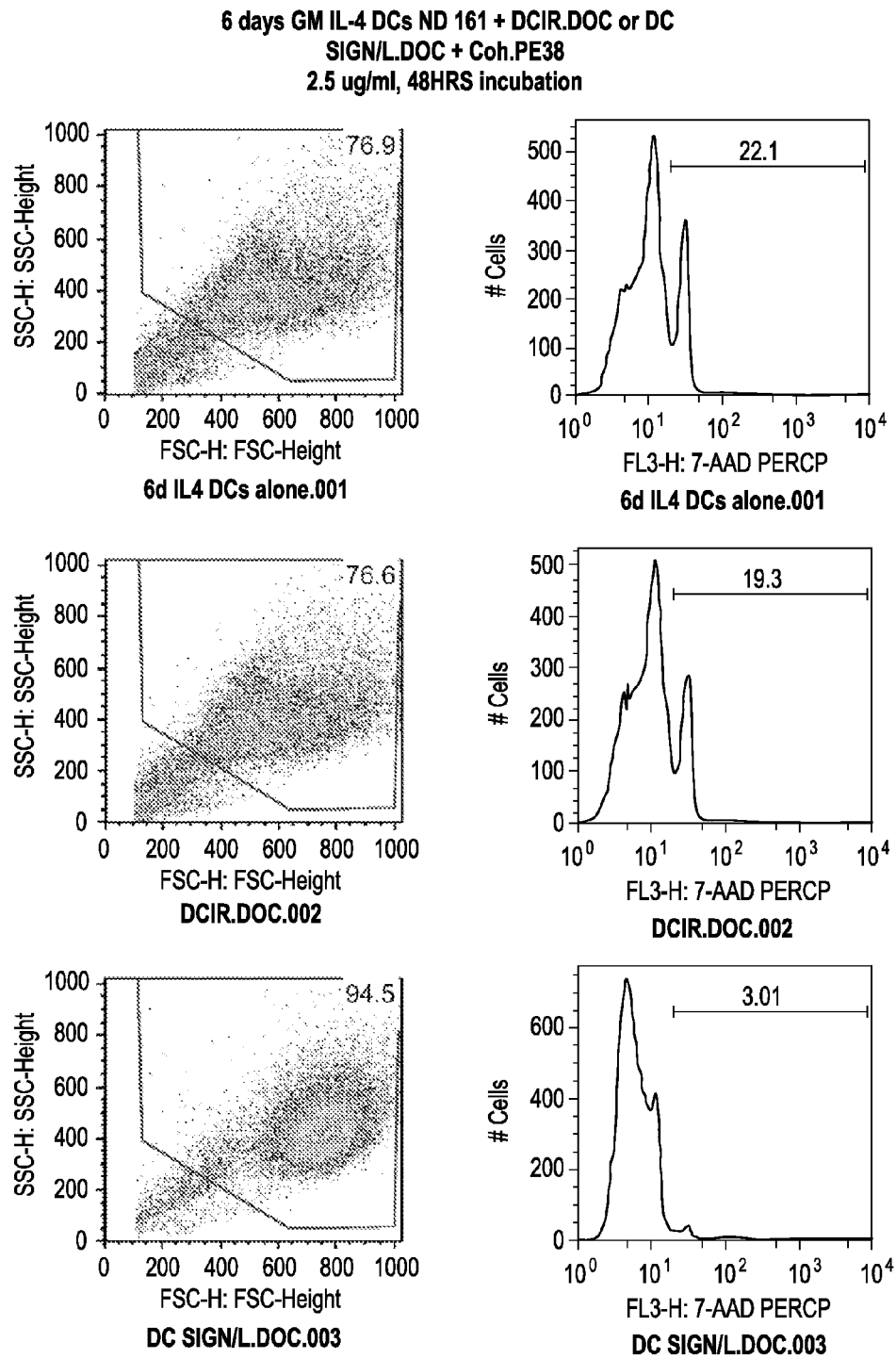
FIG. 17 shows that the DCIR.Doc rAb alone had no effect upon the survival of DCs, but DC-SIGN/L.Doc rAb enhances their survival.
Figure 18:
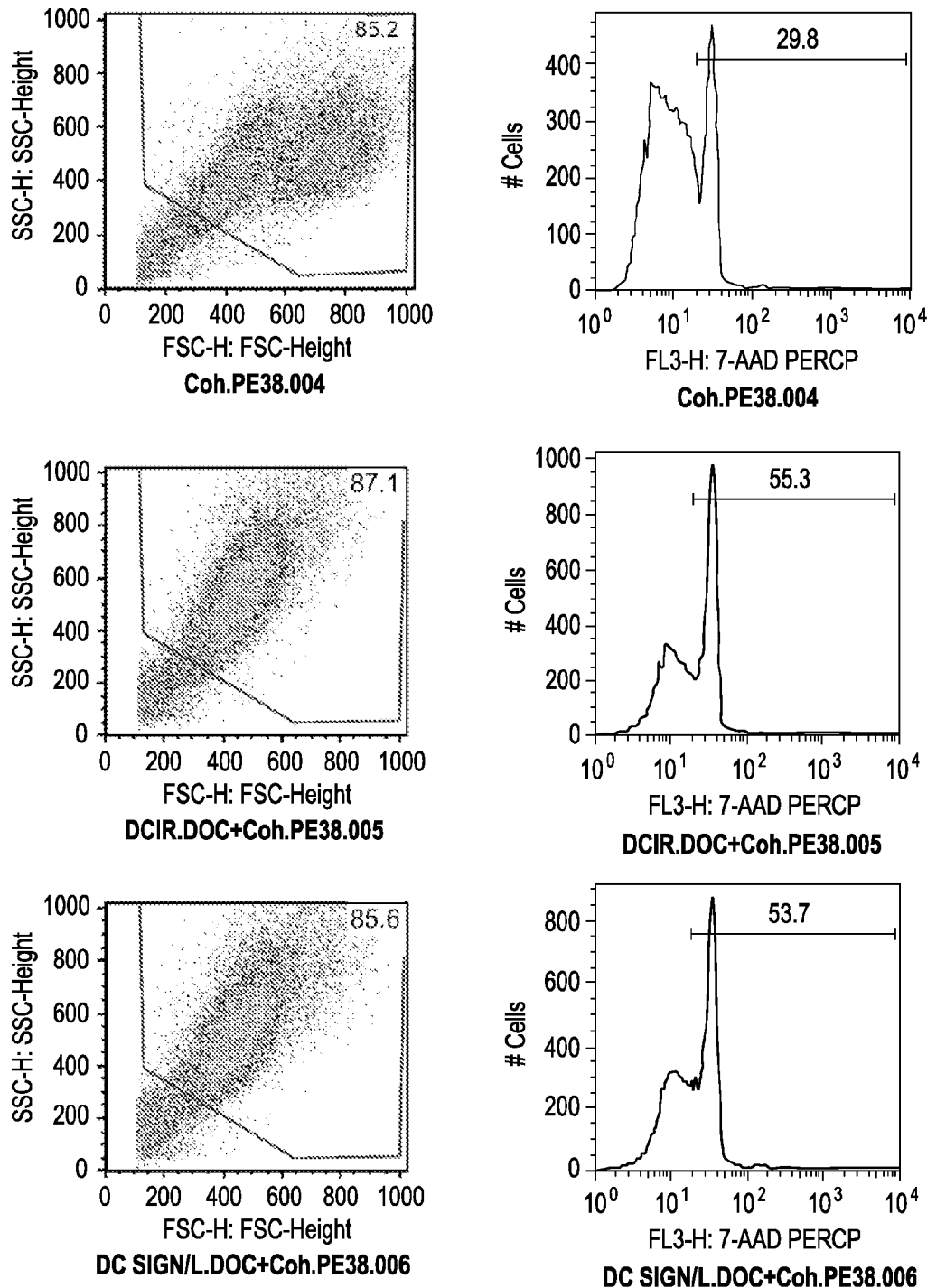
FIG. 18 shows that Coh.PE38 alone slightly increase the number of 7-AAD scored apoptotic cells (from 22.1-29.8%), but when linked to DCIR or DC-SIGN/L.Doc rAbs, Coh.PE38 greatly enhanced the number of 7-AAD scored apoptotic cells.
Figure 19:
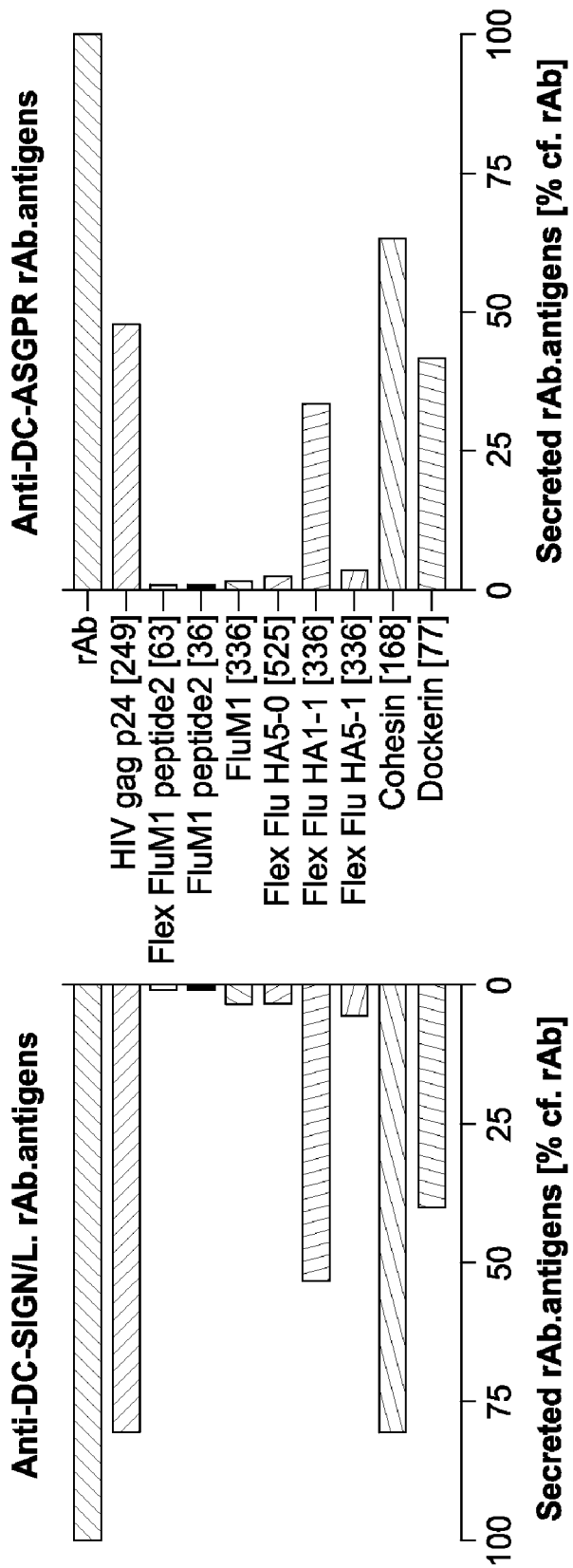
FIG. 19 shows the expression of anti-DC-SIGN/L and Anti-DC-ASPGR rAb.Coh and rAb.Doc were efficiently secreted.

While one type of embodiment of the invention is a vaccine composed of an Anti-DC-rAb.doc:coh.antigen complex, it is envisioned that in some cases a preferred DC-targeting vaccine will be Anti-DC-rAb.antigen where antigen is likely a string of protective antigens. Identification of such antigens in efficacious combinations compatible with efficient expression in production systems is extremely problematic. One embodiment of the invention affords a method to streamline testing of antigen epitope combinations for the development of such vaccines. Specifically, the invention teaches a method to screen likely antigen epitopes alone and in combinations for efficacy as a prelude to addressing production of the desired Anti-DC-rAb.antigen. For example, TABLE 13 shows the sequences of exemplative cohesin.peptide constructs which can be readily expressed via *E. coli* systems. Using techniques similar to those described in FIG. 11, diverse collections of coh.pep proteins can be readily tested for efficacy as complexes with a single anti-DC_rAb.doc entity. The most efficacious coh.pep compounds can then be engineered directly as anti-DC_rAb.peptide fusion proteins. FIG. 16 shows examples of purified coh.PEP proteins expressed in *E. coli*.

The HLA-A0201 restricted peptide sequences are:

```
GP100 WT: 154-162:  KTWGQYWQV         (SEQ ID NO.:26)

GP100 M:  209-217 (2M): IMDQVPFSV;    (SEQ ID NO.:27)

209-217 WT:  ITDQVPFSV      (SEQ ID NO.:28)

GP100 M:  280-288 (9V): YLEPGPVTV     (SEQ ID NO.:29)

280-288 WT:  YLEPGPVTA      (SEQ ID NO.:30)
```

C180 is *E. coli*-pET28(Cohesin-hgp100-PeptideA-6×His):

```
MDLDAVKIKVDTVNAKPGDTVNIPVRFSGIPSKGIANCDFVYSYDPNVLEIIEIKPGELIVDPNPTKSFDTAVYPDRKMIVELRAE
DSGTGAYAITKDGVFATIVAKVKEGAPNGLSVIKFVEVGGFANNDLVEQKTQFFDGGVNVGDTTEPATPTTPVTTPTTTDDLDAAR
SAFTIMDQVPFSVSVSASPKGAAALEHHHHHH.   (SEQ ID NO.: 31)
```

TABLE 13 shows the amino acid sequence of the melanoma antigen MART-1. Well known HLA-A201-restricted dominant peptides are shaded and detailed below the sequence. M peptides show peptide sequence variants with enhanced affinity for HLA-A201. C181 is an *E. coli* expression construct that encodes the sequence shown below in which the cohesin domain is shaded yellow and the MART-1 peptide is shaded grey. Underlined residues bounding the peptide are native to MART-1. C172 and C174 are two constructs directing the expression of anti-DC_rAb.MART-1 peptide and a matching control rAb.MART-1 peptide H chain. Only the sequences appended to the C-terminal residue are shown. C-terminal His tags are to facilitate purification via metal affinity chromatography.

MART-1 is:

```
MPREDAHFIYGYPKKGHGHSYTTAEAAGIGILTVILGVLLLIGCWYCRRRNGYRALMDKSLHVGTQCALTRRCPQEGFDHRDSKV
SLQEKNCEPVVPNAPPAYEKLSAEQSPPPYSP (SEQ ID NO.: 32)
```

The HLA-A0201 restricted peptides sequences are:

| | |
|---|---|
| MART1 WT: 9 mer: | AAGIGILTV (SEQ ID NO.: 33) |
| MART1 WT: 10 mer: | EAAGIGILTV (SEQ ID NO.: 34) |
| MART1 M: 10 mer: | ELAGIGILTV (SEQ ID NO.: 35) |

C181 is *E. coli*-pET28(Cohesin-hMART-1-PeptideB-6× His)

Cohesin.dockerin modules exist in diverse cellulose degrading species. While they have sequence similarities, they can have specificities that do not cross between species. This affords an opportunity to build novel scaffolds composed of cohesins with different specificities and use this scaffold to assemble high order complexes in a spatially and numerically controlled manner. Others have described the core technology for using this notion for biotechnology applications (see Fierobe, H.-P., Mechaly, A., Tardif, C., Belaich,

```
MDLDAVRIKVDTVNAKPGDTVNIPVRFSGIPSKGIANCDFVYSYDPNVLEIIEIKPGELIVDPNPTKSFDTAVYPDRKMIVPLFAK
DSGTGAYAITKDGVFATIVAKVKEGAPNGLSVIKFVEVGGFANNDLVEQKTQFFDGGVNVGDTTEPATPTTPVTTPTTTDDLDAAR
TAEKLAGIGILTVILGASKKGAAALEHHHHHH. (SEQ ID NO.: 36)
```

C186 is *E. coli*-pET28(Cohesin-Flex-hMART-1-PeptideA-6×His)

A., Lamed, R., Shoham, Y., Belaich, J.-P., and Bayer, E. A. (2001) Design and production of active cellulosome chime-

```
MDLDAVRIKVDTVNAKPGDTVNIPVRFSGIPSKGIANCDFVYSYDPNVLEIIEIKPGELIVDPNPTKSFDTAVYPDRKMIVPLFAK
DSGTGAYAITKDGVFATIVAKVKEGAPNGLSVIKFVEVGGFANNDLVEQKTQFFDGGVNVGDTTEPATPTTPVTTPTTTDDLDAAS
DTTEARHPHPPVTTPTTTDRKGTTAEELAGIGILTVILGGKRTNNSTPTKGEFCRYPSHWRPLEHHHHHH (SEQ ID NO.: 37)
```

C172 is rAB-pIRES2(mAnti-ASGPR__49C11__7H-LV-hIgG4H-hMART-1-PeptideA)
C174 is rAB-pIRES2(hIgG4H-hMART-1-PeptideA)

ras: Selective incorporation of dockerin-containing enzymes into defined functional complexes. J. Biol. Chem. 276, 21257-21261.). The invention embodies the specific use of

```
... ASDTTEARHPHPPVTTPTTTDRKGTTAEELAGIGILTVILGGKRTNNSTPTKGEFCRYPSHWRPRL (SEQ ID NO.: 38)
```

FIG. 16 shows *E. coli* harboring expression plasmids directing the synthesis of coh.pep proteins were grown and induced for specific protein production. Cells were harvested and broken by sonication. The supernatant fractions were applied purified by metal affinity chromatography. Analysis was by reducing SDS.PAGE gel stained by Coomassie Brilliant Blue. The figure shows typical product coh.pep proteins labeled from left to right.

This Example shows the successful use of cohesin and dockerin fusion proteins secreted from mammalian cells. If both fusion partners are rAbs with different specificities (i.e., rAb1.doc and rAb2.coh), then simple mixing results in rAb1.doc:rAb2.coh which is a bi-specific antibody. Bispecific antibodies have many potential therapeutic and technical applications. The invention provides a simple and predictable means to assemble such entities through the doc:coh interaction. Alternately, if rAb1.doc:rAb1.coh were assembled such entities represent controlled cross-linked mAbs with potentially unique biological properties.

this technology for applications related to manufacture of rAb.(doc:coh.fusion)n complexes where n represents >1 pairings of doc:coh interactions with unique specificities. Thus, the invention envisions the assembly (by simple mixing of components) of spatially ordered complexes between rAb.doc1.doc2.doc3.etc. and coh1.fusionA, coh2.fusionB, coh3.fusion3, etc. The coh.fusion proteins could represent different antigens, or combinations of antigens and activating agents like cytokines.

By extension multiple coh:doc specificities could also be used to make bivalent rAbs with higher order antigen specificities. Cellulose degrading bacteria and similar organisms also use cellulose binding domains (CBD) to organize the degradation machinery. The structure of a CBD from *Clostridium thermocellum* shows that the N and C-termini are in close proximity and are not an integral part of the CBD functional structure. In fact CBD typically occurs linked to other domains such as coh.CBD.coh in cipA. The invention encompasses the use of entities such as coh.CBD.coh to assemble spatially and numerically ordered complexes mimicking antibodies and multi subunit receptors. For example, a IgG kappa chain v region fused to doc1 and a IgG H chain V region linked to doc2 can assemble with coh1.CBD.coh2 to yield VL.doc1:coh1.CBD.coh2:VH.doc2 to yield an entity with affinity and binding specificity analogous to the original mAb. Such entities should be e.g., very useful screening tools for refining mAb specificities through mutagenesis procedures, particularly since the VL and VH component could be mutated independently and combined by mixing in various combinations. As described above, this technology can be readily extended to multiple controlled coh:V.doc combinations potentially yielding binding entities with extremely high specificities and affinities. An extension of this would be using e.g., coh1.coh2.CBD.coh3 as a template for assembly of cytoR1.doc+cytoR2.doc+cytoR3.doc (where cytoR represents the ectodomain of one subunit of a complex cytokine receptor). Such entities will have utility for blocking cytokine interactions for therapy and in biotechnology for measuring cytokines in complex supernatants.

EXAMPLE 3

Using Cohesin-Dockerin Technology for Immunotoxin Therapy

Currently 1.2 million Americans develop cancer each year and about 500,000 die from the disease, because most cancers cannot be cured once they have metastasized. To develop a new treatment for metastatic cancer, genetic engineering has been used to modify a powerful bacterial toxin, *Pseudomonas* exotoxin A (PE), so that instead of killing normal cells it selectively kills cancer cells. PE is a three domain protein composed of 613 amino acids. Anti-cancer agents are produced by deleting its binding domain (aa 1-252) and replacing it with the Fv fragment of an antibody or with a growth factor that binds to antigens present on cancer cells. These agents are termed recombinant immunotoxins (RITs). RITs have been made that target Ley present on colon, breast, lung and other epithelial cancers (B3(Fv)-PE38), that target the EGF receptor overexpressed on glioblastomas (TGF-alpha-PE38), that target mutant EGF receptors present on glioblastomas (MR-1(Fv)-PE38 KDEL), and that target the IL-2 receptor present on many T and B cell leukemias and lymphomas LMB-2 or anti-Tac(Fv)-PE38 and that target CD22 on B cell malignancies and that target BL22 or RFB4(dsFv)-PE38 ovarian cancers and mesotheliomas (SS1P). These agents are produced in *E. coli* because large amounts can be readily purified from this source and because the toxin itself would kill mammalian cells expressing it. When administered to mice with the appropriate human cancer xenograft, all these RITs produce complete tumor regressions. Most of these agents are now in clinical trials in humans and several have produced complete and partial remissions in humans with cancer.

An ideal immunotoxin should be very active so that only small amounts need to be given to cause tumor regressions, stable so it remains functional during the 5-10 hours required to reach the interior of a tumor, and non immunogenic so it can be given repeatedly. Initially, recombinant immunotoxins contained amino acids 253-613 of PE (domains II and III). It has been determined that amino acids 364-395 can be deleted without loss of activity. Increased stability can be addressed by linking the toxin to a whole antibody, which are well known to have long half-lives and the technology in the invention provides this solution.

While the rAb.Doc:Coh.toxin technology can be applied to known cancer antigens, it can also be tested to kill intratumoral DC that are suspected to foster escape of the tumor from immune surveillance. In this latter case, anti-DC toxin therapy could be doubly advantageous since build up of immunity against the administered toxin itself should be suppressed (that is because DC themselves are key to the initiation of this immune response via uptake and processing of the antigen. In this therapy, the DCs that uptake the antigen die and cannot mount the anti-toxin response).

Frankel (Clinical Cancer Research, 8, 942-944, 2002) describes issues hindering the wider application of immunotoxins. These include production problems which often require refolding of *E. coli* inclusion body expressed material where misfolding contaminants are problematic. Also, affinity of the immunotoxin for its target is often difficult to obtain in sufficient strength. The technology basis of this invention addresses both these issues—firstly, we found that cohesin.PE38 fusion protein is expressed in *E. coli* as a soluble protein that can be purified in a fully functional state (with both cohesin and toxin activities in tact) by simple biochemical means without complex refolding. Secondly, high affinity monoclonal antibodies against target antigens can be routinely obtained by one practiced in the art. What is difficult is engineering the antibody variable regions in a form that is fused with toxin and fully functional for target binding. The usual means (e.g., sFv forms) of engineering invarably lead to significant loss of affinity against the target compared to the initial monoclonal antibody. The rAb.Doc:Coh.toxin technology circumvents this issue affording a means to preserve both the high affinity binding sites of the initial mAb (note that humanization of mouse mAb V regions while maintaining high and specific binding activity is routine to one practiced in the art), as well as the beneficial properties of long half-life and non-antigenicity of a full recombinant hIgG context.

Furthermore since the cohesin.toxin is produced independently, one formulation of the toxin can be conjugated to any number of separately produced targeting rAb.Doc proteins by simple mixing of the component prior to injection of the patient. This greatly simplifies manufacturing as well as research development time. The technology described in the invention can be readily applied to any toxin and any rAb specificity.

Details of the rAb.Doc:Coh.toxin technology. pRB 391 (from Dr. Pastan) Pastan, Chief of the Laboratory of Molecular Biology, Division of Basic Sciences. NCI, NIH) was used as a template for PCR with primers PE38-N3 (cacggtcaccgtctccaaagcttccggagctagc-GAGGGCGGCAGCCTGGCCGCGCT (SEQ ID NO.:39)) and PE38-C3 (GGCCGGCTCCTGCGAAGGGAGCCGGCCGGTCGCGGCCGCTTACTTCAGGTCCTCGCGCGGCGGTTTGCCG (SEQ ID NO.:40)).

Cloning was into the previously established construct C21 or *E. coli*-pET28(Cohesin-6×His) to generate a fusion protein encoding Cohesin-PE38 corresponding to the amino acid sequence shown below (grey residues are cohesin; yellow residues are PE38, separated by a linker sequence native to the cohesin domain).

```
MAKEEAVRIKVDTVNAKPGDTVNIPVRFSGIPSKGIANCDFVYSYDPNVLEIIEIKPGELIVDPNPTKSFDTAVYPDRKMIVFLFA
EDSGTGAYAITKDGVFATIVAKVKEGAPNGLSVIKFVEVGGFANNDLVEQKTQFFDGGVNVGDTTEPATPTTPVTTPTTTDDLDA
ASEGGSLAALTAHQACHLPLETFTRHRQPRGWEQLEQCGYPVQRLVALYLAARLSWNQVDQVIRNALASPGSGGDLGEAIREQPE
QARLALTLAAAESERFVRQGTGNDEAGAANGPADSGDALLERNYPTGAEFLGDGGDVSFSTRGTQNWTVERLLQAHRQLEERGYV
FVGVHGTFLEAAQSIVFGGVRARSQDLDAIWRGFYIAGDPALAYGYAQDQEPDARGRIRNGALLRVYVPRSSLPGFYRTSLTLAA
PEAAGEVERLIGHPLPLRLDAITGPEEEGGRLETILGWPLAERTVVIPSAIPTDPRNVGGDLDPSSIPDKEQAISALPDYASQPG
KPPREDLK (SEQ ID NO.: 41)
```

Expression and purification of recombinant Coh.PE38 protein—*E. coli* cells from each 1 L fermentation were resuspended in 25 ml ice-cold 50 mM Tris, 1 mM EDTA pH 8.0 with 0.1 ml of protease inhibitor Cocktail II (Calbiochem).

the C-terminus of a rAb H chain using PCR based on C17 (Mam-pCDM8(Cohesin-Cohesin-SLAML-AP-6×His)) as template. The resulting secreted H chain sequence is shown below (the cohesin domain is highlighted in grey and the C-terminal H chain residue is in bold):

```
QIQLVQSGPELKKPGETVKISCKASGYSFTNYGMNWVKQAPGKGLKWMGWINTYTGESTYADDFKGRFAFSLETSASTAYLQISN
LKNEDMATYFCARGDFRYYFDYWGQGTTLTGSSAKTKGPSVFPLAPCSRSTSESTAALGCLVKDYFPEPVTVSWNSGALTSGVH
TFPAVLQSSGLYSLSSVVTVPSSSLGTKTYTCNVDHKPSNTKVDKRVESKYGPPCPPCPAPEFEGGPSVFLFPPKPKDTLMISRT
PEVTCVVVDVSQEDPEVQFNWYVDGVEVHNAKTKPREEQFNSTYRVVSVLTVLHQDWLNGKEYKCKVSNKGLFSSIEKTISKAKG
QPREPQVYTLPPSQEEMTKNQVSLTCLVKGFYPSDIAVEWESNGQPENNYKTTPPVLDSDGSFFLYSRLTVDKSRWQEGNVFSCS

VMHEALHNHYTQKSLSLSLGKASTTEPATPTTPVTTPTTTDDLDAVRIKVDTVNAKPGDTVNIPVRFSGIPSKGIANCDFVYSYD
PNVLEIIEIKPGELIVDPNPTKSFDTAVYPDRKMTVFLFAEDSGTGAYAITKDGVFATIVAKVKEGAPNGLSVIKFVEVGGFANN
DLVEQKTQFFDGGVNVGDT. (SEQ ID NO.: 42)
```

The cells were sonicated on ice 2×5 min at setting 18 (Fisher Sonic Dismembrator 60) with a 5 min rest period and then spun at 17,000 r.p.m. (Sorvall SA-600) for 20 min at 4° C. The supernatant was passed through 1 ml ANX Sepharose column equilibrated in 50 mM Tris, 1 mM EDTA pH 8.0 and eluted with a 0-1 M NaCl gradient in Buffer B. Fractions containing Cohesin.PE38 sere identified by SDS.PAGE and pooled fractions were further purified by purification via anti-cohesin mAb affinity chromatography with elution by 0.1 M gl Mam-pCDM8(SLAML-Cohesin-hIL-21)

```
LDAIDAVRIKVDTVNAKPGDTVRIPVRFSGIPSKGIANCDFVSYSDPNVLEIIEIEPGDIIVDPNPDKSFDTAVYPDRKIIVEIR
KEDSGTGAYAITKDGVPATIVAKVKEGAPNGLSVIKFVEVGGFANNDLVEQKTQFFDGGVNVGDTTEPATPTTPVTTPTTTDDLD
ALEADQGQDRHMIRMRQLIDIVDQLKNYVNDLVPEFLPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHGSEDS (SEQ ID NO.: 43)
```

Figure 20:
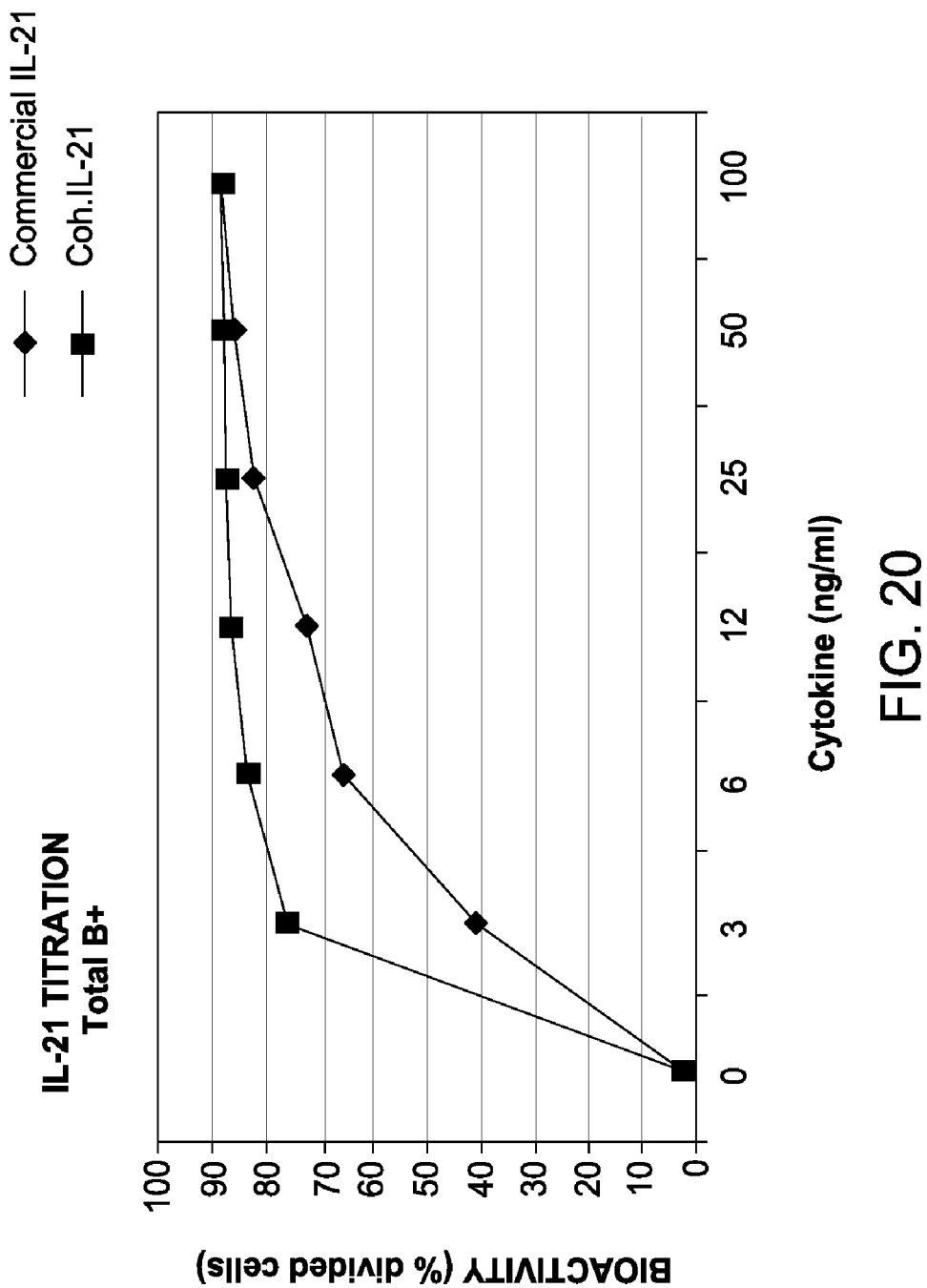
FIG. 20 shows the effect of IL-21 and Coh.IL-21 on the proliferation of human B cells.

Thus rAb.Doc:Coh.IL-21 can deliver concomitant proliferation and activation signals to a B cell (i.e., if the rAb itself has activation properties). This notion can be extended to any rAb with biological properties directed to a particular cell type and any cytokine with activity directed to the same cell type. FIG. 20 shows the effect of IL-21 and Coh.IL-21 on the proliferation of human B cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A modular recombinant rAb carrier comprising an antigen-specific binding domain linked to one or more antigen carrier domains wherein the antigen carrier domain comprising a dockerin domain or a cohesion domain capable of forming a cohesin-dockerin binding pair, and wherein the antigen-binding domain binds a dendritic cell immunoreceptor.

2. The rAb carrier of claim 1, wherein the antigen-specific binding domain comprises an immunoglobulin heavy chain or light chain.

3. The rAb carrier of claim 2, wherein the C-terminus of the heavy chain of said antigen-specific binding domain is fused to the dockerin domain or the cohesin domain to form a fusion protein.

4. The rAb carrier of claim 1, further comprising a complementary dockerin or cohesin domain bound to an antigen that forms a complex with the modular rAb carrier.

5. The rAb carrier of claim 1, further comprising a complementary dockerin or cohesin domain that is fused with an antigen.

6. The rAb carrier of claim 1, wherein the antigen-specific domain comprises a full length antibody, an antibody variable region domain, an Fab fragment, a Fab' fragment, an F(ab)$_2$ fragment, an Fv fragment, or an Fabc fragment.

7. The rAb carrier of claim 1, wherein the cohesin-dockerin are from *Bacteroides cellulosolvens*.

8. The rAb carrier of claim 1, wherein the rAb carrier is further defined as: an rAb.Doc.

9. The rAb carrier of claim 4, wherein the rAb carrier is further defined as being part of a complex: an rAb.Doc:Coh.antigen.

10. A bivalent and multivalent (rAb$^1$.Doc:Coh.rAb$^2$) self-assembled conjugate, wherein the antigen-specific binding domains rAb$^1$ and rAb$^2$ bind a cell surface marker wherein the cell surface marker is the dendritic cell immunoreceptor.

* * * * *

SEQUENCE LISTING

```
<160> NUMBER OF SEQ ID NOS: 43

<210> SEQ ID NO 1
<211> LENGTH: 2299
<212> TYPE: PRT
<213> ORGANISM: Bacteroides cellulosolvens

<400> SEQUENCE: 1

Met Gln Ser Pro Arg Leu Lys Arg Lys Ile Leu Ser Val Ile Leu Ala
1               5                   10                  15

Val Cys Tyr Ile Ile Ser Ser Phe Ser Ile Gln Phe Ala Ala Thr Pro
            20                  25                  30
```

-continued

```
Gln Val Asn Ile Ile Gly Ser Ala Gln Gly Ile Pro Gly Ser Thr
         35                  40                  45

Val Lys Val Pro Ile Asn Leu Gln Asn Val Pro Glu Ile Gly Ile Asn
 50                  55                  60

Asn Cys Asp Phe Thr Ile Lys Phe Asp Ser Asp Ile Leu Asp Phe Asn
 65                  70                  75                  80

Ser Val Glu Ala Gly Asp Ile Val Pro Leu Pro Val Ala Ser Phe Ser
                 85                  90                  95

Ser Asn Asn Ser Lys Asp Ile Ile Lys Phe Leu Phe Ser Asp Ala Thr
                100                 105                 110

Gln Gly Asn Met Pro Ile Asn Glu Asn Gly Leu Phe Ala Val Ile Ser
             115                 120                 125

Phe Lys Ile Lys Asp Asn Ala Gln Lys Gly Ile Ser Asn Ile Lys Val
130                 135                 140

Ser Ser Tyr Gly Ser Phe Ser Gly Met Ser Gly Lys Glu Met Gln Ser
145                 150                 155                 160

Leu Ser Pro Thr Phe Phe Ser Gly Ser Ile Asp Val Ser Asp Val Ser
                165                 170                 175

Thr Ser Lys Leu Asp Val Lys Val Gly Asn Val Glu Gly Ile Ala Gly
            180                 185                 190

Thr Glu Val Asn Val Pro Ile Thr Phe Glu Asn Val Pro Asp Asn Gly
            195                 200                 205

Ile Asn Asn Cys Asn Phe Thr Leu Ser Tyr Asp Ser Asn Ala Leu Glu
            210                 215                 220

Phe Leu Thr Thr Glu Ala Gly Asn Ile Ile Pro Leu Ala Ile Ala Asp
225                 230                 235                 240

Tyr Ser Ser Tyr Arg Ser Met Glu Gly Lys Ile Lys Phe Leu Phe Ser
                245                 250                 255

Asp Ser Ser Gln Gly Thr Arg Ser Ile Lys Asn Asp Gly Val Phe Ala
            260                 265                 270

Asn Ile Lys Phe Lys Ile Lys Gly Asn Ala Ile Arg Asp Thr Tyr Arg
            275                 280                 285

Ile Asp Leu Ser Glu Leu Gly Ser Phe Ser Ser Lys Gln Asn Asn Asn
            290                 295                 300

Leu Lys Ser Ile Ala Thr Gln Phe Leu Ser Gly Ser Val Asn Val Lys
305                 310                 315                 320

Asp Ile Glu Ser Val Ser Pro Thr Thr Ser Val His Pro Thr Pro
            325                 330                 335

Thr Ser Val Pro Pro Thr Pro Thr Lys Ser Ser Pro Gly Asn Lys Met
            340                 345                 350

Lys Ile Gln Ile Gly Asp Val Lys Ala Asn Gln Gly Asp Thr Val Ile
            355                 360                 365

Val Pro Ile Thr Phe Asn Glu Val Pro Val Met Gly Val Asn Asn Cys
370                 375                 380

Asn Phe Thr Leu Ala Tyr Asp Lys Asn Ile Met Glu Phe Ile Ser Ala
385                 390                 395                 400

Asp Ala Gly Asp Ile Val Thr Leu Pro Met Ala Asn Tyr Ser Tyr Asn
                405                 410                 415

Met Pro Ser Asp Gly Leu Val Lys Phe Leu Tyr Asn Asp Gln Ala Gln
            420                 425                 430

Gly Ala Met Ser Ile Lys Glu Asp Gly Thr Phe Ala Asn Val Lys Phe
            435                 440                 445

Lys Ile Lys Gln Ser Ala Ala Phe Gly Lys Tyr Ser Val Gly Ile Lys
```

-continued

```
            450                 455                 460
Ala Ile Gly Ser Ile Ser Ala Leu Ser Asn Ser Lys Leu Ile Pro Ile
465                 470                 475                 480

Glu Ser Ile Phe Lys Asp Gly Ser Ile Thr Val Thr Asn Lys Pro Ile
                    485                 490                 495

Val Asn Ile Glu Ile Gly Lys Val Lys Val Lys Ala Gly Asp Lys Ile
                500                 505                 510

Lys Val Pro Val Glu Ile Lys Asp Ile Pro Ser Ile Gly Ile Asn Asn
            515                 520                 525

Cys Asn Phe Thr Leu Lys Tyr Asn Ser Asn Val Leu Lys Tyr Val Ser
530                 535                 540

Asn Glu Ala Gly Thr Ile Val Pro Ala Pro Leu Ala Asn Leu Ser Ile
545                 550                 555                 560

Asn Lys Pro Asp Glu Gly Ile Ile Lys Leu Leu Phe Ser Asp Ala Ser
                565                 570                 575

Gln Gly Gly Met Pro Ile Lys Asp Asn Gly Ile Phe Val Asn Leu Glu
                580                 585                 590

Phe Gln Ala Val Asn Asp Ala Asn Ile Gly Val Tyr Gly Leu Glu Leu
                595                 600                 605

Asp Thr Ile Gly Ala Phe Ser Gly Ile Ser Ser Ala Lys Met Thr Ser
            610                 615                 620

Ile Glu Pro Gln Phe Asn Asn Gly Ser Ile Glu Ile Phe Asn Ser Ala
625                 630                 635                 640

Gln Thr Pro Val Pro Ser Asn Thr Glu Val Gln Thr Pro Thr Asn Thr
                645                 650                 655

Ile Ser Val Thr Pro Thr Asn Asn Ser Thr Pro Thr Asn Asn Ser Thr
                660                 665                 670

Pro Lys Pro Asn Pro Leu Tyr Asn Leu Asn Val Asn Ile Gly Glu Ile
            675                 680                 685

Ser Gly Glu Ala Gly Gly Val Ile Glu Val Pro Ile Glu Phe Lys Asn
            690                 695                 700

Val Pro Asp Phe Gly Ile Asn Asn Cys Asp Phe Ser Val Lys Tyr Asp
705                 710                 715                 720

Lys Ser Ile Phe Glu Tyr Val Thr Tyr Glu Ala Gly Ser Ile Val Lys
                725                 730                 735

Asp Ser Ile Val Asn Leu Ala Cys Met Glu Asn Ser Gly Ile Ile Asn
                740                 745                 750

Leu Leu Phe Asn Asp Ala Thr Gln Ser Ser Ser Pro Ile Lys Asn Asn
            755                 760                 765

Gly Val Phe Ala Lys Leu Lys Phe Lys Ile Asn Ser Asn Ala Ala Ser
            770                 775                 780

Gly Thr Tyr Gln Ile Asn Ala Glu Gly Tyr Gly Lys Phe Ser Gly Asn
785                 790                 795                 800

Leu Asn Gly Lys Leu Thr Ser Ile Asn Pro Ile Phe Glu Asn Gly Ile
                805                 810                 815

Ile Asn Ile Gly Asn Val Thr Val Lys Pro Thr Ser Thr Pro Ala Asp
            820                 825                 830

Ser Ser Thr Ile Thr Pro Thr Ala Thr Pro Ala Thr Pro Thr Ile
            835                 840                 845

Lys Gly Thr Pro Thr Val Thr Pro Ile Tyr Trp Met Asn Val Leu Ile
            850                 855                 860

Gly Asn Met Asn Ala Ala Ile Gly Glu Glu Val Val Pro Ile Glu
865                 870                 875                 880
```

-continued

```
Phe Lys Asn Val Pro Pro Phe Gly Ile Asn Asn Cys Asp Phe Lys Leu
                885             890             895

Val Tyr Asp Ser Asn Ala Leu Glu Leu Lys Lys Val Glu Ala Gly Asp
            900             905             910

Ile Val Pro Glu Pro Leu Ala Asn Leu Ser Ser Asn Lys Ser Glu Gly
        915             920             925

Lys Ile Gln Phe Leu Phe Asn Asp Ala Ser Gln Gly Ser Met Gln Ile
    930             935             940

Glu Asn Gly Gly Val Phe Ala Lys Ile Thr Phe Lys Val Lys Ser Thr
945             950             955             960

Ala Ala Ser Gly Ile Tyr Asn Ile Arg Lys Asp Ser Val Gly Ser Phe
            965             970             975

Ser Gly Leu Ile Asp Asn Lys Met Thr Ser Ile Gly Pro Lys Phe Thr
            980             985             990

Asp Gly Ser Ile Val Val Gly Thr Val Thr Pro Thr Ala Thr Ala Thr
            995             1000            1005

Pro Ser Ala Ile Val Thr Thr Ile Thr Pro Thr Ala Thr Thr Lys
    1010            1015            1020

Pro Ile Ala Thr Pro Thr Ile Lys Gly Thr Pro Thr Ala Thr Pro
    1025            1030            1035

Met Tyr Trp Met Asn Val Val Ile Gly Lys Met Asn Ala Glu Val
    1040            1045            1050

Gly Gly Glu Val Val Val Pro Ile Glu Phe Asn Asn Val Pro Ser
    1055            1060            1065

Phe Gly Ile Asn Asn Cys Asp Phe Lys Leu Val Tyr Asp Ala Thr
    1070            1075            1080

Ala Leu Glu Leu Lys Asn Val Glu Ala Gly Asp Ile Ile Lys Thr
    1085            1090            1095

Pro Leu Ala Asn Phe Ser Asn Asn Lys Ser Glu Glu Gly Lys Ile
    1100            1105            1110

Ser Phe Leu Phe Asn Asp Ala Ser Gln Gly Ser Met Gln Ile Glu
    1115            1120            1125

Asn Gly Gly Val Phe Ala Lys Ile Thr Phe Lys Val Lys Ser Thr
    1130            1135            1140

Thr Ala Thr Gly Val Tyr Asp Leu Arg Lys Asp Leu Val Gly Ser
    1145            1150            1155

Phe Ser Gly Leu Lys Asp Asn Lys Met Thr Ser Ile Gly Ala Glu
    1160            1165            1170

Phe Thr Asn Gly Ser Ile Thr Val Ala Ala Thr Ala Pro Thr Val
    1175            1180            1185

Thr Pro Thr Val Asn Ala Thr Pro Ser Ala Ala Thr Pro Thr Val
    1190            1195            1200

Thr Pro Thr Ala Thr Ala Thr Pro Ser Val Thr Ile Pro Thr Val
    1205            1210            1215

Thr Pro Thr Ala Thr Ala Thr Pro Ser Val Thr Ile Pro Thr Val
    1220            1225            1230

Thr Pro Thr Ala Thr Ala Thr Pro Ser Ala Ala Thr Pro Thr Val
    1235            1240            1245

Thr Pro Thr Ala Thr Ala Thr Pro Ser Val Thr Ile Pro Thr Val
    1250            1255            1260

Thr Pro Thr Val Thr Ala Thr Pro Ser Asp Thr Ile Pro Thr Val
    1265            1270            1275
```

-continued

```
Thr Pro Thr Ala Thr Ala Thr Pro Ser Ala Ile Val Thr Thr Ile
    1280            1285            1290

Thr Pro Thr Ala Thr Ala Lys Pro Ile Ala Thr Pro Thr Ile Lys
    1295            1300            1305

Gly Thr Pro Thr Ala Thr Pro Met Tyr Trp Met Asn Val Val Ile
    1310            1315            1320

Gly Lys Met Asn Ala Glu Val Gly Gly Glu Val Val Val Pro Ile
    1325            1330            1335

Glu Phe Lys Asn Val Pro Ser Phe Gly Ile Asn Asn Cys Asp Phe
    1340            1345            1350

Lys Leu Val Tyr Asp Ala Thr Ala Leu Glu Leu Lys Asn Val Glu
    1355            1360            1365

Ala Gly Asp Ile Ile Lys Thr Pro Leu Ala Asn Phe Ser Asn Asn
    1370            1375            1380

Lys Ser Glu Glu Gly Lys Ile Ser Phe Leu Phe Asn Asp Ala Ser
    1385            1390            1395

Gln Gly Ser Met Gln Ile Glu Asn Gly Gly Val Ser Ala Lys Ile
    1400            1405            1410

Thr Phe Lys Val Lys Ser Thr Thr Ala Ile Gly Val Tyr Asp Ile
    1415            1420            1425

Arg Lys Asp Leu Ile Gly Ser Phe Ser Gly Leu Lys Asp Ser Lys
    1430            1435            1440

Met Thr Ser Ile Gly Ala Glu Phe Thr Asn Gly Ser Ile Thr Val
    1445            1450            1455

Ala Thr Thr Ala Pro Thr Val Thr Pro Thr Ala Thr Ala Thr Pro
    1460            1465            1470

Ser Val Thr Ile Pro Thr Val Thr Pro Thr Ala Thr Ala Thr Pro
    1475            1480            1485

Gly Thr Ala Thr Pro Gly Thr Ala Thr Pro Thr Ala Thr Ala Thr
    1490            1495            1500

Pro Gly Ala Ala Thr Pro Thr Glu Thr Ala Pro Ser Val Met
    1505            1510            1515

Ile Pro Thr Val Thr Pro Thr Ala Thr Ala Thr Pro Thr Ala Thr
    1520            1525            1530

Ala Thr Pro Thr Val Lys Gly Thr Pro Thr Ile Lys Pro Val Tyr
    1535            1540            1545

Lys Met Asn Val Val Ile Gly Arg Val Asn Val Val Ala Gly Glu
    1550            1555            1560

Glu Val Val Val Pro Val Glu Phe Lys Asn Ile Pro Ala Ile Gly
    1565            1570            1575

Val Asn Asn Cys Asn Phe Val Leu Glu Tyr Asp Ala Asn Val Leu
    1580            1585            1590

Glu Val Lys Lys Val Asp Ala Gly Glu Ile Val Pro Asp Ala Leu
    1595            1600            1605

Ile Asn Phe Gly Ser Asn Asn Ser Asp Glu Gly Lys Val Tyr Phe
    1610            1615            1620

Leu Phe Asn Asp Ala Leu Gln Gly Arg Met Gln Ile Ala Asn Asp
    1625            1630            1635

Gly Ile Phe Ala Asn Ile Thr Phe Lys Val Lys Ser Ser Ala Ala
    1640            1645            1650

Ala Gly Ile Tyr Asn Ile Arg Lys Asp Ser Val Gly Ala Phe Ser
    1655            1660            1665

Gly Leu Val Asp Lys Leu Val Pro Ile Ser Ala Glu Phe Thr Asp
```

```
                 1670                1675                1680
Gly  Ser  Ile  Ser  Val  Glu  Ser  Ala  Lys  Ser  Thr  Pro  Thr  Ala  Thr
          1685                1690                1695

Ala  Thr  Gly  Thr  Asn  Val  Thr  Pro  Thr  Val  Ala  Ala  Thr  Val  Thr
          1700                1705                1710

Pro  Thr  Ala  Thr  Pro  Ala  Ser  Thr  Thr  Pro  Thr  Ala  Thr  Pro  Thr
          1715                1720                1725

Ala  Thr  Ser  Thr  Val  Lys  Gly  Thr  Pro  Thr  Ala  Thr  Pro  Leu  Tyr
          1730                1735                1740

Ser  Met  Asn  Val  Ile  Ile  Gly  Lys  Val  Asn  Ala  Glu  Ala  Ser  Gly
          1745                1750                1755

Glu  Val  Val  Val  Pro  Val  Glu  Phe  Lys  Asp  Val  Pro  Ser  Ile  Gly
          1760                1765                1770

Ile  Asn  Asn  Cys  Asn  Phe  Ile  Leu  Glu  Tyr  Asp  Ala  Ser  Ala  Leu
          1775                1780                1785

Glu  Leu  Asp  Ser  Ala  Glu  Ala  Gly  Glu  Ile  Val  Pro  Val  Pro  Leu
          1790                1795                1800

Gly  Asn  Phe  Ser  Ser  Asn  Asn  Lys  Asp  Glu  Gly  Lys  Ile  Tyr  Phe
          1805                1810                1815

Leu  Phe  Ser  Asp  Gly  Thr  Gln  Gly  Arg  Met  Gln  Ile  Val  Asn  Asp
          1820                1825                1830

Gly  Ile  Phe  Ala  Lys  Ile  Lys  Phe  Lys  Val  Lys  Ser  Thr  Ala  Ser
          1835                1840                1845

Asp  Gly  Thr  Tyr  Tyr  Ile  Arg  Lys  Asp  Ser  Val  Gly  Ala  Phe  Ser
          1850                1855                1860

Gly  Leu  Ile  Glu  Lys  Lys  Ile  Ile  Lys  Ile  Gly  Ala  Glu  Phe  Thr
          1865                1870                1875

Asp  Gly  Ser  Ile  Thr  Val  Arg  Ser  Leu  Thr  Pro  Thr  Pro  Thr  Val
          1880                1885                1890

Thr  Pro  Asn  Val  Ala  Ser  Pro  Thr  Pro  Thr  Lys  Val  Val  Ala  Glu
          1895                1900                1905

Pro  Thr  Ser  Asn  Gln  Pro  Ala  Gly  Pro  Gly  Pro  Ile  Thr  Gly  Thr
          1910                1915                1920

Ile  Pro  Thr  Ala  Thr  Thr  Thr  Ala  Thr  Ala  Thr  Pro  Thr  Lys  Ala
          1925                1930                1935

Ser  Val  Ala  Thr  Ala  Thr  Pro  Thr  Ala  Thr  Pro  Ile  Val  Val  Val
          1940                1945                1950

Glu  Pro  Thr  Ile  Val  Arg  Pro  Gly  Tyr  Asn  Lys  Asp  Ala  Asp  Leu
          1955                1960                1965

Ala  Val  Phe  Ile  Ser  Ser  Asp  Lys  Ser  Arg  Tyr  Glu  Glu  Ser  Ser
          1970                1975                1980

Ile  Ile  Thr  Tyr  Ser  Ile  Glu  Tyr  Lys  Asn  Ile  Gly  Lys  Val  Asn
          1985                1990                1995

Ala  Thr  Asn  Val  Lys  Ile  Ala  Ala  Gln  Ile  Pro  Lys  Phe  Thr  Lys
          2000                2005                2010

Val  Tyr  Asp  Ala  Ala  Lys  Gly  Ala  Val  Lys  Gly  Ser  Glu  Ile  Val
          2015                2020                2025

Trp  Met  Ile  Gly  Asn  Leu  Ala  Val  Gly  Glu  Ser  Tyr  Thr  Lys  Glu
          2030                2035                2040

Tyr  Lys  Val  Lys  Val  Asp  Ser  Leu  Thr  Lys  Ser  Glu  Glu  Tyr  Thr
          2045                2050                2055

Asp  Asn  Thr  Val  Thr  Ile  Ser  Ser  Asp  Gln  Thr  Val  Asp  Ile  Pro
          2060                2065                2070
```

```
Glu Asn Ile Thr Thr Gly Asn Asp Asp Lys Ser Thr Ile Arg Val
    2075                2080                2085

Met Leu Tyr Ser Asn Arg Phe Thr Pro Gly Ser His Ser Ser Tyr
    2090                2095                2100

Ile Leu Gly Tyr Lys Asp Lys Thr Phe Lys Pro Lys Gln Asn Val
    2105                2110                2115

Thr Arg Ala Glu Val Ala Ala Met Phe Ala Arg Ile Met Gly Leu
    2120                2125                2130

Thr Val Lys Asp Gly Ala Lys Ser Ser Tyr Lys Asp Val Ser Asn
    2135                2140                2145

Lys His Trp Ala Leu Lys Tyr Ile Glu Ala Val Thr Lys Ser Gly
    2150                2155                2160

Ile Phe Lys Gly Tyr Lys Asp Ser Thr Phe His Pro Asn Ala Pro
    2165                2170                2175

Ile Thr Arg Ala Glu Leu Ser Thr Val Ile Phe Asn Tyr Leu His
    2180                2185                2190

Leu Asn Asn Ile Ala Pro Ser Lys Val His Phe Thr Asp Ile Asn
    2195                2200                2205

Lys His Trp Ala Lys Asn Tyr Ile Glu Glu Ile Tyr Arg Phe Lys
    2210                2215                2220

Leu Ile Gln Gly Tyr Ser Asp Gly Ser Phe Lys Pro Asn Asn Asn
    2225                2230                2235

Ile Thr Arg Ala Glu Val Val Thr Met Ile Asn Arg Met Leu Tyr
    2240                2245                2250

Arg Gly Pro Leu Lys Val Lys Val Gly Ser Phe Pro Asp Val Ser
    2255                2260                2265

Pro Lys Tyr Trp Ala Tyr Gly Asp Ile Glu Glu Ala Ser Arg Asn
    2270                2275                2280

His Lys Tyr Thr Arg Asp Glu Lys Asp Gly Ser Glu Ile Leu Ile
    2285                2290                2295

Glu

<210> SEQ ID NO 2
<211> LENGTH: 1653
<212> TYPE: DNA
<213> ORGANISM: Artificial
<220> FEATURE:
<223> OTHER INFORMATION: Chemically synthesized oligonucleotide

<400> SEQUENCE: 2
atggacctcc tgtgcaagaa catgaagcac ctgtggttct tcctcctgct ggtggcggct    60
cccagatggg tcctgtcccg gctgcagctg caggagtcgg gcccaggcct gctgaagcct   120
tcggtgaccc tgtccctcac ctgcactgtc tcgggtgact ccgtcgccag tagttcttat   180 tactgggget gggtccgtca gcccccaggg aagggactcg agtggatagg gactatcaat   240
tttagtggca atatgtatta tagtccgtcc ctcaggagtc gagtgaccat gtcggcagac   300
atgtccgaga actccttcta tctgaaattg actctgtga ccgcagcaga cacggccgtc   360
tattattgtg cggcaggaca cctcgttatg ggatttgggg cccactgggg acagggaaaa   420
ctggtctccg tctctccagc ttccaccaag ggcccatccg tcttccccct ggcgccctgc   480
tccaggagca cctccgagag cacagccgcc ctgggctgcc tggtcaagga ctacttcccc   540
gaaccggtga cggtgtcgtg gaactcaggc gccctgacca gcggcgtgca caccttcccg   600
gctgtcctac agtcctcagg actctactcc ctcagcagcg tggtgaccgt gccctccagc   660
```

-continued

```
agcttgggca cgaagaccta cacctgcaac gtagatcaca agcccagcaa caccaaggtg    720
gacaagagag ttgagtccaa atatggtccc ccatgcccac cctgcccagc acctgagttc    780 gaaggggggac catcagtctt cctgttcccc ccaaaaccca aggacactct catgatctcc    840
cggacccctg aggtcacgtg cgtggtggtg gacgtgagcc aggaagaccc cgaggtccag    900
ttcaactggt acgtggatgg cgtggaggtg cataatgcca agacaaagcc gcgggaggag    960
cagttcaaca gcacgtaccg tgtggtcagc gtcctcaccg tcctgcacca ggactggctg   1020
aacggcaagg agtacaagtg caaggtctcc aacaaaggcc tcccgtcctc catcgagaaa   1080
accatctcca aagccaaagg gcagccccga gagccacagg tgtacaccct gcccccatcc   1140
caggaggaga tgaccaagaa ccaggtcagc ctgacctgcc tggtcaaagg cttctacccc   1200
agcgacatcg ccgtggagtg ggagagcaat gggcagccgg agaacaacta caagaccacg   1260
cctcccgtgc tggactccga cggctccttc ttcctctaca gcaggctaac cgtggacaag   1320
agcaggtggc aggaggggaa tgtcttctca tgctccgtga tgcatgaggc tctgcacaac   1380
cactacacac agaagagcct ctccctgtct ctgggtaaag ctagcaattc tcctcaaaat   1440
gaagtactgt acggagatgt gaatgatgac ggaaaagtaa actccactga cttgactttg   1500
ttaaaaagat atgttcttaa agccgtctca actctccctt cttccaaagc tgaaagaaac   1560
gcagatgtaa atcgtgacgg aagagttaat tccagtgatg tcacaatact ttcaagatat   1620
ttgataaggg taatcgagaa attaccaata taa                                1653
```

<210> SEQ ID NO 3
<211> LENGTH: 524
<212> TYPE: PRT
<213> ORGANISM: Artificial
<220> FEATURE:
<223> OTHER INFORMATION: Chemically synthesized peptide

<400> SEQUENCE: 3

```
Arg Leu Gln Leu Gln Glu Ser Gly Pro Gly Leu Leu Lys Pro Ser Val
 1               5                  10                  15

Thr Leu Ser Leu Thr Cys Thr Val Ser Gly Asp Ser Val Ala Ser Ser
            20                  25                  30

Ser Tyr Tyr Trp Gly Trp Val Arg Gln Pro Pro Gly Lys Gly Leu Glu
        35                  40                  45

Trp Ile Gly Thr Ile Asn Phe Ser Gly Asn Met Tyr Tyr Ser Pro Ser
    50                  55                  60

Leu Arg Ser Arg Val Thr Met Ser Ala Asp Met Ser Glu Asn Ser Phe
65                  70                  75                  80

Tyr Leu Lys Leu Asp Ser Val Thr Ala Ala Asp Thr Ala Val Tyr Tyr
                85                  90                  95

Cys Ala Ala Gly His Leu Val Met Gly Phe Gly Ala His Trp Gly Gln
            100                 105                 110

Gly Lys Leu Val Ser Val Ser Pro Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                    180                 185                 190
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser Asn Ser Pro Gln Asn Glu Val Leu Tyr Gly Asp Val Asn Asp Asp
    450                 455                 460

Gly Lys Val Asn Ser Thr Asp Leu Thr Leu Leu Lys Arg Tyr Val Leu
465                 470                 475                 480

Lys Ala Val Ser Thr Leu Pro Ser Ser Lys Ala Glu Lys Asn Ala Asp
                485                 490                 495

Val Asn Arg Asp Gly Arg Val Asn Ser Ser Asp Val Thr Ile Leu Ser
            500                 505                 510

Arg Tyr Leu Ile Arg Val Ile Glu Lys Leu Pro Ile
        515                 520

<210> SEQ ID NO 4
<211> LENGTH: 1635
<212> TYPE: DNA
<213> ORGANISM: Artificial
<220> FEATURE:
<223> OTHER INFORMATION: Chemically synthesized oligonucleotide

<400> SEQUENCE: 4
atgaaatgca gctgggtcat cttcttcctg atggcagtgg ttacaggggt caattcagag      60
gttcagctgc agcagtctgg ggctgagctt gtgaggccag ggccttagt caagttgtcc     120
```

-continued

```
tgcaaagctt ctggcttcaa cattaatgac tactatatcc actgggtgaa gcagcggcct      180
gaacagggcc tggagcggat tggatggatt gatcctgaca atggtaatac tatatatgac      240
ccgaagttcc agggcaaggc cagtataaca gcagacacat ccccaacac agcctacctg       300 cagctcagca gcctgacatc tgaggacact gccgtctatt actgtgctag aacccgatct      360
cctatggtta cgacggggtt tgtttactgg ggccaaggga ctgtggtcac tgtctctgca      420
gccaaaacga agggcccatc cgtcttcccc ctggcgccct gctccaggag cacctccgag      480
agcacagccg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacgaagacc      660
tacacctgca acgtagatca caagcccagc aacaccaagg tggacaagag agttgagtcc      720
aaatatggtc cccatgccc  accctgccca gcacctgagt tcgaagggg  accatcagtc      780 ttcctgttcc ccccaaaacc caaggacact ctcatgatct cccggacccc tgaggtcacg      840
tgcgtggtgg tggacgtgag ccaggaagac cccgaggtcc agttcaactg gtacgtggat      900
ggcgtggagg tgcataatgc caagacaaag ccgcgggagg agcagttcaa cagcacgtac      960
cgtgtggtca gcgtcctcac cgtcctgcac caggactggc tgaacggcaa ggagtacaag     1020
tgcaaggtct ccaacaaagg cctcccgtcc tccatcgaga aaaccatctc caaagccaaa     1080
gggcagcccc gagagccaca ggtgtacacc ctgcccccat cccaggagga gatgaccaag     1140
aaccaggtca gcctgacctg cctggtcaaa ggcttctacc ccagcgacat cgccgtggag     1200
tgggagagca atgggcagcc ggagaacaac tacaagacca cgcctcccgt gctggactcc     1260
gacggctcct tcttcctcta cagcaggcta accgtggaca agagcaggtg gcaggagggg     1320
aatgtcttct catgctccgt gatgcatgag gctctgcaca accactacac acagaagagc     1380
ctctccctgt ctctgggtaa agctagcaat tctcctcaaa atgaagtact gtacggagat     1440
gtgaatgatg acggaaaagt aaactccact gacttgactt tgttaaaaag atatgttctt     1500
aaagccgtct caactctccc ttcttccaaa gctgaaaaga acgcagatgt aaatcgtgac     1560
ggaagagtta attccagtga tgtcacaata ctttcaagat atttgataag ggtaatcgag     1620
aaattaccaa tataa                                                     1635
```

<210> SEQ ID NO 5
<211> LENGTH: 525
<212> TYPE: PRT
<213> ORGANISM: Artificial
<220> FEATURE:
<223> OTHER INFORMATION: Chemically synthesized peptide

<400> SEQUENCE: 5

```
Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Asn Asp Tyr
            20                  25                  30

Tyr Ile His Trp Val Lys Gln Arg Pro Glu Gln Gly Leu Glu Arg Ile
        35                  40                  45

Gly Trp Ile Asp Pro Asp Asn Gly Asn Thr Ile Tyr Asp Pro Lys Phe
    50                  55                  60

Gln Gly Lys Ala Ser Ile Thr Ala Asp Thr Ser Pro Asn Thr Ala Tyr
65                  70                  75                  80

Leu Gln Leu Ser Ser Leu Thr Ser Glu Asp Thr Ala Val Tyr Tyr Cys
                85                  90                  95
```

-continued

Ala Arg Thr Arg Ser Pro Met Val Thr Thr Gly Phe Val Tyr Trp Gly
            100                 105                 110

Gln Gly Thr Val Val Thr Val Ser Ala Ala Lys Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

Ala Ser Asn Ser Pro Gln Asn Glu Val Leu Tyr Gly Asp Val Asn Asp
    450                 455                 460

Asp Gly Lys Val Asn Ser Thr Asp Leu Thr Leu Leu Lys Arg Tyr Val
465                 470                 475                 480

Leu Lys Ala Val Ser Thr Leu Pro Ser Ser Lys Ala Glu Lys Asn Ala
                485                 490                 495

Asp Val Asn Arg Asp Gly Arg Val Asn Ser Ser Asp Val Thr Ile Leu
            500                 505                 510

```
Ser Arg Tyr Leu Ile Arg Val Ile Glu Lys Leu Pro Ile
    515                 520                 525
```

<210> SEQ ID NO 6
<211> LENGTH: 1638
<212> TYPE: DNA
<213> ORGANISM: Artificial
<220> FEATURE:
<223> OTHER INFORMATION: Chemically synthesized oligonucleotide

<400> SEQUENCE: 6

| | | | | | |
|---|---|---|---|---|---|
| atggacccca | aaggctccct | ttcctggaga | atacttctgt | ttctctccct | ggcttttgag | 60 |
| ttgtcgtacg | gagatgtgca | gcttcaggag | tcaggacctg | acctggtgaa | accttctcag | 120 |
| tcactttcac | tcacctgcac | tgtcactggc | tactccatca | ccagtggtta | tagctggcac | 180 |
| tggatccggc | agtttccagg | aaacaaactg | gaatggatgg | gctacatact | cttcagtggt | 240 |
| agcactaact | acaacccatc | tctgaaaagt | cgaatctcta | tcactcgaga | cacatccaag | 300 |
| aaccagttct | tcctgcagtt | gaattctgtg | actactgagg | acacagccac | atatttctgt | 360 |
| gcaagatcta | actatggttc | ctttgcttcc | tggggccaag | ggactctggt | cactgtctct | 420 |
| gcagccaaaa | caaagggccc | atccgtcttc | ccctggcgc  | cctgctccag | gagcacctcc | 480 |
| gagagcacag | ccgccctggg | ctgcctggtc | aaggactact | ccccgaacc  | ggtgacggtg | 540 |
| tcgtggaact | caggcgccct | gaccagcggc | gtgcacacct | tcccggctgt | cctacagtcc | 600 |
| tcaggactct | actccctcag | cagcgtggtg | accgtgccct | ccagcagctt | gggcacgaag | 660 |
| acctacacct | gcaacgtaga | tcacaagccc | agcaacacca | aggtggacaa | gagagttgag | 720 |
| tccaaatatg | gtccccatg  | cccaccctgc | ccagcacctg | agttcgaagg | gggaccatca | 780 |
| gtcttcctgt | tccccccaaa | acccaaggac | actctcatga | tctcccggac | ccctgaggtc | 840 |
| acgtgcgtgg | tggtggacgt | gagccaggaa | gaccccgagg | tccagttcaa | ctggtacgtg | 900 |
| gatggcgtgg | aggtgcataa | tgccaagaca | aagccgcggg | aggagcagtt | caacagcacg | 960 |
| taccgtgtgg | tcagcgtcct | caccgtcctg | caccaggact | ggctgaacgg | caaggagtac | 1020 |
| aagtgcaagg | tctccaacaa | aggcctcccg | tcctccatcg | agaaaaccat | ctccaaagcc | 1080 |
| aaagggcagc | cccgagagcc | acaggtgtac | accctgcccc | catcccagga | ggagatgacc | 1140 |
| aagaaccagg | tcagcctgac | ctgcctggtc | aaaggcttct | accccagcga | catcgccgtg | 1200 |
| gagtgggaga | gcaatgggca | gccggagaac | aactacaaga | ccacgcctcc | cgtgctggac | 1260 |
| tccgacggct | ccttcttcct | ctacagcagg | ctaaccgtgg | acaagagcag | gtggcaggag | 1320 |
| gggaatgtct | tctcatgctc | cgtgatgcat | gaggctctgc | acaaccacta | cacacagaag | 1380 |
| agcctctccc | tgtctctggg | taaagctagc | aattctcctc | aaaatgaagt | actgtacgga | 1440 |
| gatgtgaatg | atgacggaaa | agtaaactcc | actgacttga | ctttgttaaa | aagatatgtt | 1500 |
| cttaaagccg | tctcaactct | cccttcttcc | aaagctgaaa | agaacgcaga | tgtaaatcgt | 1560 |
| gacggaagag | ttaattccag | tgatgtcaca | atactttcaa | gatatttgat | aagggtaatc | 1620 |
| gagaaattac | aatataa | | | | | 1638 |

<210> SEQ ID NO 7
<211> LENGTH: 521
<212> TYPE: PRT
<213> ORGANISM: Artificial
<220> FEATURE:
<223> OTHER INFORMATION: Chemically synthesized peptide

<400> SEQUENCE: 7

-continued

```
Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr Ser Gly
             20                  25                  30

Tyr Ser Trp His Trp Ile Arg Gln Phe Pro Gly Asn Lys Leu Glu Trp
         35                  40                  45

Met Gly Tyr Ile Leu Phe Ser Gly Ser Thr Asn Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Phe Cys
                 85                  90                  95

Ala Arg Ser Asn Tyr Gly Ser Phe Ala Ser Trp Gly Gln Gly Thr Leu
                100                 105                 110

Val Thr Val Ser Ala Ala Lys Thr Lys Gly Pro Ser Val Phe Pro Leu
             115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
```

```
                    420               425               430
Tyr Thr Gln Lys Ser Leu Ser Leu Ser Leu Gly Lys Ala Ser Asn Ser
            435               440               445
Pro Gln Asn Glu Val Leu Tyr Gly Asp Val Asn Asp Asp Gly Lys Val
        450               455               460
Asn Ser Thr Asp Leu Thr Leu Leu Lys Arg Tyr Val Leu Lys Ala Val
465               470               475               480
Ser Thr Leu Pro Ser Ser Lys Ala Glu Lys Asn Ala Asp Val Asn Arg
                485               490               495
Asp Gly Arg Val Asn Ser Ser Asp Val Thr Ile Leu Ser Arg Tyr Leu
            500               505               510
Ile Arg Val Ile Glu Lys Leu Pro Ile
            515               520

<210> SEQ ID NO 8
<211> LENGTH: 1623
<212> TYPE: DNA
<213> ORGANISM: Artificial
<220> FEATURE:
<223> OTHER INFORMATION: Chemically synthesized oligonucleotide

<400> SEQUENCE: 8
atggaaaggc actggatctt tctcttcctg ttttcagtaa ctgcaggtgt ccactcccag      60
gtccagcttc agcagtctgg ggctgagctg caaaacctg gggcctcagt gaagatgtcc     120
tgcaaggctt ctggctacac ctttactacc tactggatgc actgggtaaa acagaggcct     180
ggacagggtc tggaatggat tggatacatt aatcctatca ctggttatac tgagtacaat     240
cagaagttca aggacaaggc caccttgact gcagacaaat cctccagcac agcctacatg     300
caactgagca gcctgacatc tgaggactct gcagtctatt actgtgcaag agagggttta     360
agtgctatgg actattgggg tcagggaacc tcagtcaccg tcacctcagc caaaacaacg     420
ggcccatccg tcttccccct ggcgccctgc tccaggagca cctccgagag cacagccgcc     480
ctgggctgcc tggtcaagga ctacttcccc gaaccggtga cggtgtcgtg gaactcaggc     540
gccctgacca gcggcgtgca caccttcccg gctgtcctac agtcctcagg actctactcc     600
ctcagcagcg tggtgaccgt gccctccagc agcttgggca cgaagaccta cacctgcaac     660
gtagatcaca agcccagcaa caccaaggtg gacaagagag ttgagtccaa atatggtccc     720
ccatgcccac cctgcccagc acctgagttc aagggggac catcagtctt cctgttcccc     780
ccaaaaccca aggacactct catgatctcc cggacccctg aggtcacgtg cgtggtggtg     840
gacgtgagcc aggaagaccc cgaggtccag ttcaactggt acgtggatgg cgtggaggtg     900
cataatgcca agacaaagcc gcgggaggag cagttcaaca gcacgtaccg tgtggtcagc     960
gtcctcaccg tcctgcacca ggactggctg aacggcaagg agtacaagtg caaggtctcc    1020
aacaaaggcc tcccgtcctc catcgagaaa accatctcca aagccaaagg cagccccga     1080
gagccacagg tgtacaccct gcccccatcc caggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccacg cctcccgtgc tggactccga cggctccttc    1260
ttcctctaca gcaggctaac cgtggacaag agcaggtggc aggaggggaa tgtcttctca    1320
tgctccgtga tgcatgaggc tctgcacaac cactacacac agaagagcct ctccctgtct    1380
ctgggtaaag ctagcaattc tcctcaaaat gaagtactgt acgagatgt gaatgatgac    1440
ggaaaagtaa actccactga cttgactttg ttaaaaagat atgttcttaa agccgtctca    1500
```

-continued

```
actctcccctt cttccaaagc tgaaaagaac gcagatgtaa atcgtgacgg aagagttaat    1560
tccagtgatg tcacaatact ttcaagatat ttgataaggg taatcgagaa attaccaata    1620
taa                                                                  1623
```

<210> SEQ ID NO 9
<211> LENGTH: 521
<212> TYPE: PRT
<213> ORGANISM: Artificial
<220> FEATURE:
<223> OTHER INFORMATION: Chemically synthesized peptide

<400> SEQUENCE: 9

| Gln | Val | Gln | Leu | Gln | Gln | Ser | Gly | Ala | Glu | Leu | Ala | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Met | Ser | Cys | Lys | Ala | Ser | Gly | Tyr | Thr | Phe | Thr | Thr | Tyr |
| | | | 20 | | | | | 25 | | | | | 30 | | |

| Trp | Met | His | Trp | Val | Lys | Gln | Arg | Pro | Gly | Gln | Gly | Leu | Glu | Trp | Ile |
| | | 35 | | | | | 40 | | | | | 45 | | | |

| Gly | Tyr | Ile | Asn | Pro | Ile | Thr | Gly | Tyr | Thr | Glu | Tyr | Asn | Gln | Lys | Phe |
| 50 | | | | | 55 | | | | | 60 | | | | | |

| Lys | Asp | Lys | Ala | Thr | Leu | Thr | Ala | Asp | Lys | Ser | Ser | Ser | Thr | Ala | Tyr |
| 65 | | | | | 70 | | | | | 75 | | | | | 80 |

| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |

| Ala | Arg | Glu | Gly | Leu | Ser | Ala | Met | Asp | Tyr | Trp | Gly | Gln | Gly | Thr | Ser |
| | | | 100 | | | | | 105 | | | | | 110 | | |

| Val | Thr | Val | Thr | Ser | Ala | Lys | Thr | Thr | Gly | Pro | Ser | Val | Phe | Pro | Leu |
| | | 115 | | | | | 120 | | | | | 125 | | | |

| Ala | Pro | Cys | Ser | Arg | Ser | Thr | Ser | Glu | Ser | Thr | Ala | Ala | Leu | Gly | Cys |
| 130 | | | | | 135 | | | | | 140 | | | | | |

| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |

| Gly | Ala | Leu | Thr | Ser | Gly | Val | His | Thr | Phe | Pro | Ala | Val | Leu | Gln | Ser |
| | | | | 165 | | | | | 170 | | | | | 175 | |

| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |

| Leu | Gly | Thr | Lys | Thr | Tyr | Thr | Cys | Asn | Val | Asp | His | Lys | Pro | Ser | Asn |
| | | 195 | | | | | 200 | | | | | 205 | | | |

| Thr | Lys | Val | Asp | Lys | Arg | Val | Glu | Ser | Lys | Tyr | Gly | Pro | Pro | Cys | Pro |
| | 210 | | | | | 215 | | | | | 220 | | | | |

| Pro | Cys | Pro | Ala | Pro | Glu | Phe | Glu | Gly | Gly | Pro | Ser | Val | Phe | Leu | Phe |
| 225 | | | | | 230 | | | | | 235 | | | | | 240 |

| Pro | Pro | Lys | Pro | Lys | Asp | Thr | Leu | Met | Ile | Ser | Arg | Thr | Pro | Glu | Val |
| | | | | 245 | | | | | 250 | | | | | 255 | |

| Thr | Cys | Val | Val | Val | Asp | Val | Ser | Gln | Glu | Asp | Pro | Glu | Val | Gln | Phe |
| | | | 260 | | | | | 265 | | | | | 270 | | |

| Asn | Trp | Tyr | Val | Asp | Gly | Val | Glu | Val | His | Asn | Ala | Lys | Thr | Lys | Pro |
| | | 275 | | | | | 280 | | | | | 285 | | | |

| Arg | Glu | Glu | Gln | Phe | Asn | Ser | Thr | Tyr | Arg | Val | Val | Ser | Val | Leu | Thr |
| | 290 | | | | | 295 | | | | | 300 | | | | |

| Val | Leu | His | Gln | Asp | Trp | Leu | Asn | Gly | Lys | Glu | Tyr | Lys | Cys | Lys | Val |
| 305 | | | | | 310 | | | | | 315 | | | | | 320 |

| Ser | Asn | Lys | Gly | Leu | Pro | Ser | Ser | Ile | Glu | Lys | Thr | Ile | Ser | Lys | Ala |
| | | | | 325 | | | | | 330 | | | | | 335 | |

```
Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser Asn Ser
                435                 440                 445

Pro Gln Asn Glu Val Leu Tyr Gly Asp Val Asn Asp Asp Gly Lys Val
        450                 455                 460

Asn Ser Thr Asp Leu Thr Leu Leu Lys Arg Tyr Val Leu Lys Ala Val
465                 470                 475                 480

Ser Thr Leu Pro Ser Ser Lys Ala Glu Lys Asn Ala Asp Val Asn Arg
                485                 490                 495

Asp Gly Arg Val Asn Ser Ser Asp Val Thr Ile Leu Ser Arg Tyr Leu
                500                 505                 510

Ile Arg Val Ile Glu Lys Leu Pro Ile
                515                 520

<210> SEQ ID NO 10
<211> LENGTH: 732
<212> TYPE: DNA
<213> ORGANISM: Artificial
<220> FEATURE:
<223> OTHER INFORMATION: Chemically synthesized oligonucleotide

<400> SEQUENCE: 10
atgcatcgca ccagcatggg catcaagatg gagtcacaga ttcaggcatt tgtattcgtg      60
tttctctggt tgtctggtgt tggcggagac attgtgatga cccagtctca caaattcatg    120
tccacatcag taggagacag ggtcagcgtc acctgcaagg ccagtcagga tgtgacttct    180
gctgtagcct ggtatcaaca aaaaccaggg caatctccta aactactgat ttactgggca    240
tccacccggc acactggagt ccctgatcgc ttcacaggca gtggatctgg gacagattat    300
actctcacca tcagcagtgt gcaggctgaa gacctggcac tttattactg tcaccaatat    360
tatagcgctc tcggacgttc ggtggaggc accaagctcg agatcaaacg aactgtggct    420
gcaccatctg tcttcatctt cccgccatct gatgagcagt tgaaatctgg aactgcctct    480
gttgtgtgcc tgctgaataa cttctatccc agagaggcca agtacagtg aaggtggat    540 aacgccctcc aatcgggtaa ctcccaggag agtgtcacag agcaggacag caaggacagc    600
acctacagcc tcagcagcac cctgacgctg agcaaagcag actacgagaa acacaaagtc    660
tatgcctgcg aagtcaccca tcagggcctg agctcgcccg tcacaaagag cttcaacagg    720
ggagagtgtt ag                                                        732

<210> SEQ ID NO 11
<211> LENGTH: 214
<212> TYPE: PRT
<213> ORGANISM: Artificial
<220> FEATURE:
```

<223> OTHER INFORMATION: Chemically synthesized peptide

<400> SEQUENCE: 11

Asp Ile Val Met Thr Gln Ser His Lys Phe Met Ser Thr Ser Val Gly
1               5                   10                  15

Asp Arg Val Ser Val Thr Cys Lys Ala Ser Gln Asp Val Thr Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Gly Gln Ala
65                  70                  75                  80

Glu Asp Leu Ala Leu Tyr Tyr Cys His Gln Tyr Ser Ala Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 1644
<212> TYPE: DNA
<213> ORGANISM: Artificial
<220> FEATURE:
<223> OTHER INFORMATION: Chemically synthesized oligonucleotide

<400> SEQUENCE: 12
atgggatggt catgtatcat ccttttttcta gtagcaactg caactggagt acattcacag      60
gtccaactgc agcagcctgg ggctgagctg gtgaggcctg ggacttcagt gaagttgtcc     120
tgcaaggctt ctggttacat ctttaccagc tactggatgc actgggtaaa gcagaggcct     180
ggacaaggcc ttgagtggat cggactgatt gatccttctg atagttatag taagtacaat     240
caaaagttca gggcaaggc cacattgact gtagacacat cctccagcac agcctacatg     300
cagctcagca gcctgacatc tgaggactct gcggtctatt actgtgcaag aggggagctc     360
agtgacttct ggggccaagg caccactctc acagtctcct cagccaaaac aacacccca     420 tcagtctatc cactggcccc tgggtgtgga gatacaactg gttcctctgt gactctggga     480
tgcctggtca aggctactt ccctgagtca gtgactgtga cttggaactc tggatccctg     540
tccagcagtg tgcacacctt cccagctctc ctgcagtctg gactctacac tatgagcagc     600
tcagtgactg tccctccag cacctggcca agtcagaccg tcacctgcag cgttgctcac     660
ccagccagca gcaccacggt ggacaaaaaa cttgagccca gcgggcccat ttcaacaatc     720

```
aacccctgtc ctccatgcaa ggagtgtcac aaatgcccag ctcctaacct cgagggtgga      780
ccatccgtct tcatcttccc tccaaatatc aaggatgtac tcatgatctc cctgacaccc      840
aaggtcacgt gtgtggtggt ggatgtgagc gaggatgacc cagacgtccg gatcagctgg      900
tttgtgaaca acgtggaagt acacacagct cagacacaaa cccatagaga ggattacaac      960
agtactatcc gggtggtcag tgccctcccc atccagcacc aggactggat gagtggcaag     1020
gagttcaaat gcaaggtcaa caacaaagac ctcccatcac ccatcgagag aaccatctca     1080
aaaattaaag ggctagtcag agctccacaa gtatacatct tgccgccacc agcagagcag     1140
ttgtccagga agatgtcag tctcacttgc ctggtcgtgg gcttcaaccc tggagacatc      1200
agtgtggagt ggaccagcaa tgggcataca gaggagaact acaaggacac cgcaccagtc     1260
ctggactctg acggttctta cttcatatac agcaagctcg atataaaaac aagcaagtgg     1320
gagaaaacag attccttctc atgcaacgtg agacacgagg gtctgaaaaa ttactacctg     1380
aagaagacca tctcccggtc tccgggtaaa gctagcaatt ctcctcaaaa tgaagtactg     1440
tacggagatg tgaatgatga cggaaaagta aactccactg acttgacttt gttaaaaaga     1500
tatgttctta agccgtctc aactctgcct tcttccaaag ctgaaaagaa cgcagatgta      1560
aatcgtgacg aagagttaa ttccagtgat gtcacaatac tttcaagata tttgataagg      1620
gtaatcgaga aattaccaat ataa                                              1644
```

<210> SEQ ID NO 13
<211> LENGTH: 528
<212> TYPE: PRT
<213> ORGANISM: Artificial
<220> FEATURE:
<223> OTHER INFORMATION: Chemically synthesized peptide

<400> SEQUENCE: 13

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Leu Ile Asp Pro Ser Asp Ser Tyr Ser Lys Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Glu Leu Ser Asp Phe Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Cys Gly Asp Thr Thr Gly Ser Ser Val Thr Leu Gly Cys Leu Val
    130                 135                 140

Lys Gly Tyr Phe Pro Glu Ser Val Thr Val Thr Trp Asn Ser Gly Ser
145                 150                 155                 160

Leu Ser Ser Ser Val His Thr Phe Pro Ala Leu Leu Gln Ser Gly Leu
                165                 170                 175

Tyr Thr Met Ser Ser Ser Val Thr Val Pro Ser Ser Thr Trp Pro Ser
            180                 185                 190

```
Gln Thr Val Thr Cys Ser Val Ala His Pro Ala Ser Ser Thr Thr Val
        195                 200                 205

Asp Lys Lys Leu Glu Pro Ser Gly Pro Ile Ser Thr Ile Asn Pro Cys
    210                 215                 220

Pro Pro Cys Lys Glu Cys His Lys Cys Pro Ala Pro Asn Leu Glu Gly
225                 230                 235                 240

Gly Pro Ser Val Phe Ile Phe Pro Pro Asn Ile Lys Asp Val Leu Met
                245                 250                 255

Ile Ser Leu Thr Pro Lys Val Thr Cys Val Val Asp Val Ser Glu
                260                 265                 270

Asp Asp Pro Asp Val Arg Ile Ser Trp Phe Val Asn Asn Val Glu Val
        275                 280                 285

His Thr Ala Gln Thr Gln Thr His Arg Glu Asp Tyr Asn Ser Thr Ile
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ser Pro Ile
                325                 330                 335

Glu Arg Thr Ile Ser Lys Ile Lys Gly Leu Val Arg Ala Pro Gln Val
            340                 345                 350

Tyr Ile Leu Pro Pro Pro Ala Glu Gln Leu Ser Arg Lys Asp Val Ser
        355                 360                 365

Leu Thr Cys Leu Val Val Gly Phe Asn Pro Gly Asp Ile Ser Val Glu
    370                 375                 380

Trp Thr Ser Asn Gly His Thr Glu Glu Asn Tyr Lys Asp Thr Ala Pro
385                 390                 395                 400

Val Leu Asp Ser Asp Gly Ser Tyr Phe Ile Tyr Ser Lys Leu Asp Ile
                405                 410                 415

Lys Thr Ser Lys Trp Glu Lys Thr Asp Ser Phe Ser Cys Asn Val Arg
            420                 425                 430

His Glu Gly Leu Lys Asn Tyr Tyr Leu Lys Lys Thr Ile Ser Arg Ser
        435                 440                 445

Pro Gly Lys Ala Ser Asn Ser Pro Gln Asn Glu Val Leu Tyr Gly Asp
    450                 455                 460

Val Asn Asp Asp Gly Lys Val Asn Ser Thr Asp Leu Thr Leu Leu Lys
465                 470                 475                 480

Arg Tyr Val Leu Lys Ala Val Ser Thr Leu Pro Ser Ser Lys Ala Glu
                485                 490                 495

Lys Asn Ala Asp Val Asn Arg Asp Gly Arg Val Asn Ser Ser Asp Val
            500                 505                 510

Thr Ile Leu Ser Arg Tyr Leu Ile Arg Val Ile Glu Lys Leu Pro Ile
        515                 520                 525

<210> SEQ ID NO 14
<211> LENGTH: 2061
<212> TYPE: DNA
<213> ORGANISM: Artificial
<220> FEATURE:
<223> OTHER INFORMATION: Chemically synthesized oligonucleotide

<400> SEQUENCE: 14
atggatccca aaggatccct ttcctggaga atacttctgt ttctctccct ggctttgag      60 ttgagctacg gactcgacga tctggatgca gtaaggatta agtggacac agtaaatgca    120 aaaccgggag acacagtaag aatacctgta agattcagcg gtataccatc caagggaata    180
```

-continued

```
gcaaactgtg actttgtata cagctatgac ccgaatgtac ttgagataat agagatagaa      240
ccgggagaca taatagttga cccgaatcct gacaagagct tgatactgc agtatatcct       300 gacagaaaga taatagtatt cctgtttgca aagacagcg aacaggagc gtatgcaata        360 actaaagacg gagtatttgc tacgatagta gcgaaagtaa aagaaggagc acctaacgga      420
ctcagtgtaa tcaaatttgt agaagtaggc ggatttgcga acaatgacct tgtagaacag      480 aagcacagt tctttgacgg tggagtaaat gttggagata aacagaaacc tgcaacacct      540
acaacacctg taacaacacc gacaacaaca gatgatctgg atgcactcga gatcatccca     600
gttgaggagg agaacccgga cttctggaac cgcgaggcag ccgaggccct gggtgccgcc     660
aagaagctgc agcctgcaca gacagccgcc aagaacctca tcatcttcct gggcgatggg     720 atggggggtgt ctacggtgac agctgccagg atcctaaaag gcagaagaa ggacaaactg     780 gggcctgagt tacccctggc catggaccgc ttcccatatg tggctctgtc aagacatac     840 aatgtagaca aacatgtgcc agacagtgga gccacagcca cggcctacct gtgcggggtc    900
aagggcaact tccagaccat tggcttgagt gcagccgccc gctttaacca gtgcaacacg    960
acacgcggca acgaggtcat ctccgtgatg aatcgggcca agaaagcagg gaagtcagtg   1020
ggagtggtaa ccaccacacg agtgcagcac gcctcgccag ccggcaccta cgcccacacg   1080
gtgaaccgca actggtactc ggacgccgac gtgcctgcct cggcccgcca ggaggggtgc   1140
caggacatcg ctacgcagct catctccaac atggacattg acgtgatcct aggtggaggc   1200
cgaaagtaca tgtttcgcat gggaacccca gaccctgagt acccagatga ctacagccaa   1260
ggtgggacca ggctggacgg gaagaatctg gtgcaggaat ggctggcgaa gcgccagggt   1320
gcccggtacg tgtggaaccg cactgagctc atgcaggctt ccctggaccc gtctgtgacc   1380
catctcatgg gtctctttga gcctggagac atgaaatacg agatccaccg agactccaca   1440
ctggacccct ccctgatgga gatgacagag gctgccctgc gcctgctgag caggaacccc   1500
cgcggcttct tcctcttcgt ggagggtggt cgcatcgacc atggtcatca tgaaagcagg   1560
gcttaccggg cactgactga gacgatcatg ttcgacgacg ccattgagag ggcgggccag   1620
ctcaccagcg aggaggacac gctgagcctc gtcactgccg accactccca cgtcttctcc   1680
ttcggaggct accccctgcg agggagctcc atcttcgggc tggcccctgg caaggcccgg   1740
gacaggaagg cctacacggt cctcctatac ggaaacggtc aggctatgt gctcaaggac   1800 ggcgccccggc cggatgttac cgagagcgag agcgggagcc ccgagtatcg gcagcagtca   1860
gcagtgcccc tggacgaaga gacccacgca ggcgaggacg tggcggtgtt cgcgcgcggc   1920
ccgcaggcgc acctggttca cggcgtgcag gagcagacct tcatagcgca cgtcatggcc   1980
ttcgccgcct gcctggagcc ctacaccgcc tgcgacctgg cgcccccgc cggcaccacc   2040 caccatcacc atcaccattg a                                              2061
```

<210> SEQ ID NO 15
<211> LENGTH: 662
<212> TYPE: PRT
<213> ORGANISM: Artificial
<220> FEATURE:
<223> OTHER INFORMATION: Chemically synthesized peptide

<400> SEQUENCE: 15

Leu Asp Asp Leu Asp Ala Val Arg Ile Lys Val Asp Thr Val Asn Ala
1               5                   10                  15

Lys Pro Gly Asp Thr Val Arg Ile Pro Val Arg Phe Ser Gly Ile Pro
            20                  25                  30

```
Ser Lys Gly Ile Ala Asn Cys Asp Phe Val Tyr Ser Tyr Asp Pro Asn
        35                  40                  45

Val Leu Glu Ile Ile Glu Ile Glu Pro Gly Glu Leu Ile Val Asp Pro
 50                  55                  60

Asn Pro Thr Lys Ser Phe Asp Thr Ala Val Tyr Pro Asp Arg Lys Met
 65                  70                  75                  80

Ile Val Phe Leu Phe Ala Glu Asp Ser Gly Thr Gly Ala Tyr Ala Ile
                 85                  90                  95

Thr Glu Asp Gly Val Phe Ala Thr Ile Val Ala Lys Val Lys Ser Gly
             100                 105                 110

Ala Pro Asn Gly Leu Ser Val Ile Lys Phe Val Glu Val Gly Gly Phe
         115                 120                 125

Ala Asn Asn Asp Leu Val Glu Gln Lys Thr Gln Phe Phe Asp Gly Gly
     130                 135                 140

Val Asn Val Gly Asp Thr Thr Glu Pro Ala Thr Pro Thr Thr Pro Val
145                 150                 155                 160

Thr Thr Pro Thr Thr Thr Asp Asp Leu Asp Ala Leu Glu Ile Ile Pro
                 165                 170                 175

Val Glu Glu Glu Asn Pro Asp Phe Trp Asn Arg Glu Ala Ala Glu Ala
                 180                 185                 190

Leu Gly Ala Ala Lys Lys Leu Gln Pro Ala Gln Thr Ala Ala Lys Asn
             195                 200                 205

Leu Ile Ile Phe Leu Gly Asp Gly Met Gly Val Ser Thr Val Thr Ala
         210                 215                 220

Ala Arg Ile Leu Lys Gly Gln Lys Lys Asp Lys Leu Gly Pro Glu Leu
225                 230                 235                 240

Pro Leu Ala Met Asp Arg Phe Pro Tyr Val Ala Leu Ser Lys Thr Tyr
                 245                 250                 255

Asn Val Asp Lys His Val Pro Asp Ser Gly Ala Thr Ala Thr Ala Tyr
             260                 265                 270

Leu Cys Gly Val Lys Gly Asn Phe Gln Thr Ile Gly Leu Ser Ala Ala
         275                 280                 285

Ala Arg Phe Asn Gln Cys Asn Thr Thr Arg Gly Asn Glu Val Ile Ser
     290                 295                 300

Val Met Asn Arg Ala Lys Lys Ala Gly Lys Ser Val Gly Val Val Thr
305                 310                 315                 320

Thr Thr Arg Val Gln His Ala Ser Pro Ala Gly Thr Tyr Ala His Thr
                 325                 330                 335

Val Asn Arg Asn Trp Tyr Ser Asp Ala Asp Val Pro Ala Ser Ala Arg
             340                 345                 350

Gln Glu Gly Cys Gln Asp Ile Ala Thr Gln Leu Ile Ser Asn Met Asp
         355                 360                 365

Ile Asp Val Ile Leu Gly Gly Gly Arg Lys Tyr Met Phe Arg Met Gly
     370                 375                 380

Thr Pro Asp Pro Glu Tyr Pro Asp Asp Tyr Ser Gln Gly Gly Thr Arg
385                 390                 395                 400

Leu Asp Gly Lys Asn Leu Val Gln Glu Trp Leu Ala Lys Arg Gln Gly
                 405                 410                 415

Ala Arg Tyr Val Trp Asn Arg Thr Glu Leu Met Gln Ala Ser Leu Asp
             420                 425                 430

Pro Ser Val Thr His Leu Met Gly Leu Phe Glu Pro Gly Asp Met Lys
         435                 440                 445
```

```
Tyr Glu Ile His Arg Asp Ser Thr Leu Asp Pro Ser Leu Met Glu Met
450                 455                 460

Thr Glu Ala Ala Leu Arg Leu Leu Ser Arg Asn Pro Arg Gly Phe Phe
465                 470                 475                 480

Leu Phe Val Glu Gly Gly Arg Ile Asp His Gly His His Glu Ser Arg
            485                 490                 495

Ala Tyr Arg Ala Leu Thr Glu Thr Ile Met Phe Asp Asp Ala Ile Glu
            500                 505                 510

Arg Ala Gly Gln Leu Thr Ser Glu Glu Asp Thr Leu Ser Leu Val Thr
            515                 520                 525

Ala Asp His Ser His Val Phe Ser Phe Gly Gly Tyr Pro Leu Arg Gly
            530                 535                 540

Ser Ser Ile Phe Gly Leu Ala Pro Gly Lys Ala Arg Asp Arg Lys Ala
545                 550                 555                 560

Tyr Thr Val Leu Leu Tyr Gly Asn Gly Pro Gly Tyr Val Leu Lys Asp
                565                 570                 575

Gly Ala Arg Pro Asp Val Thr Glu Ser Glu Ser Gly Ser Pro Glu Tyr
            580                 585                 590

Arg Gln Gln Ser Ala Val Pro Leu Asp Glu Glu Thr His Ala Gly Glu
            595                 600                 605

Asp Val Ala Val Phe Ala Arg Gly Pro Gln Ala His Leu Val His Gly
            610                 615                 620

Val Gln Glu Gln Thr Phe Ile Ala His Val Met Ala Phe Ala Ala Cys
625                 630                 635                 640

Leu Glu Pro Tyr Thr Ala Cys Asp Leu Ala Pro Pro Ala Gly Thr Thr
                645                 650                 655

His His His His His His
            660

<210> SEQ ID NO 16
<211> LENGTH: 2556
<212> TYPE: DNA
<213> ORGANISM: Artificial
<220> FEATURE:
<223> OTHER INFORMATION: Chemically synthesized oligonucleotide

<400> SEQUENCE: 16
atggatccca aaggatccct ttcctggaga atacttctgt ttctctccct ggcttttgag      60
ttgagctacg gactcgacga tctggatgca gtaaggatta agtggacac agtaaatgca      120 aaaccgggag acacagtaag aataacctgta agattcagcg gtataccatc caagggaata   180
gcaaactgtg actttgtata cagctatgac ccgaatgtac ttgagataat agagataaaa   240
ccgggagaat tgatagttga cccgaatcct gacaagagct tgatactgc agtatatcct    300 gacagaaaga taatagtatt cctgtttgca gaagacagcg gaacaggagc gtatgcaata   360
actaaagacg gagtatttgc tacgatagta gcgaaagtaa aatccggagc acctaacgga   420
ctcagtgtaa tcaaatttgt agaagtaggc ggatttgcga ataatgacct tgtagaacag   480
aagacacagt tctttgacgg tggagtaaat gttggagata caacagaacc tgcaacacct   540
acaacacctg taacaacacc gacaacaaca atgatctgg atgcagtaag gattaaagtg   600
gacacagtaa atgcaaaacc gggagacaca gtaaatatac ctgtaagatt cagtggtata   660
ccatccaagg gaatagcaaa ctgtgacttt gtatacagct atgacccgaa tgtacttgag   720
ataatagaga taaaaccggg agaattgata gttgacccga atcctaccaa gagctttgat   780
actgcagtat atcctgacag aaagatgata gtattcctgt ttgcggaaga cagcggaaca   840
```

```
ggagcgtatg caataactaa agacggagta tttgctacga tagtagcgaa agtaaaagaa    900
ggagcaccta acggactcag tgtaatcaaa tttgtagaag taggcggatt tgcgaacaat    960
gaccttgtag aacagaagac acagttcttt gacggtggag taaatgttgg agatacaaca   1020
gaacctgcaa cacctacaac acctgtaaca acaccgacaa caacagatga tctggatgca   1080
ctcgagatca tcccagttga ggaggagaac ccggacttct ggaaccgcga ggcagccgag   1140
gccctgggtg ccgccaagaa gctgcagcct gcacagacag ccgccaagaa cctcatcatc   1200
ttcctgggcg atgggatggg ggtgtctacg gtgacagctg ccaggatcct aaaagggcag   1260
aagaaggaca aactggggcc tgagttaccc ctggccatgg accgcttccc atatgtggct   1320
ctgtccaaga catacaatgt agacaaacat gtgccagaca gtggagccac agccacggcc   1380
tacctgtgcg gggtcaaggg caacttccag accattggct tgagtgcagc cgcccgcttt   1440
aaccagtgca acacgacacg cggcaacgag gtcatctccg tgatgaatcg ggccaagaaa   1500
gcagggaagt cagtgggagt ggtaaccacc acacgagtgc agcacgcctc gccagccggc   1560
acctacgccc acacggtgaa ccgcaactgg tactcggacg ccgacgtgcc tgcctcggcc   1620
cgccaggagg ggtgccagga catcgctacg cagctcatct ccaacatgga cattgacgtg   1680
atcctaggtg gaggccgaaa gtacatgttt cgcatgggaa ccccagaccc tgagtaccca   1740
gatgactaca gccaaggtgg gaccaggctg acgggaaga atctggtgca ggaatggctg   1800
gcgaagcgcc agggtgcccg gtacgtgtgg aaccgcactg agctcatgca ggcttccctg   1860
gacccgtctg tgacccatct catgggtctc tttgagcctg agacatgaa atacgagatc   1920
caccgagact ccacactgga cccctccctg atggagatga cagaggctgc cctgcgcctg   1980
ctgagcagga accccgcgg cttcttcctc ttcgtggagg gtggtcgcat cgaccatggt   2040
catcatgaaa gcagggctta ccgggcactg actgagacga tcatgttcga cgacgccatt   2100
gagagggcgg gccagctcac cagcgaggag gacacgctga gcctcgtcac tgccgaccac   2160
tcccacgtct tctccttcgg aggctacccc ctgcgaggga gctccatctt cgggctggcc   2220
cctggcaagg cccgggacag gaaggcctac acgtcctcc tatacggaaa cggtccaggc   2280
tatgtgctca aggacggcgc ccggccggat gttaccgaga gcgagagcgg gagccccgag   2340
tatcggcagc agtcagcagt gcccctggac gaagagaccc acgcaggcga ggacgtggcg   2400
gtgttcgcgc gcggcccgca ggcgcacctg gttcacggcg tgcaggagca gaccttcata   2460
gcgcacgtca tggccttcgc cgcctgcctg gagccctaca ccgcctgcga cctggcgccc   2520
cccgccggca ccacccacca tcaccatcac cattga                             2556
```

<210> SEQ ID NO 17
<211> LENGTH: 826
<212> TYPE: PRT
<213> ORGANISM: Artificial
<220> FEATURE:
<223> OTHER INFORMATION: Chemically synthesized oligonucleotide

<400> SEQUENCE: 17

Leu Asp Leu Asp Ala Val Arg Ile Lys Val Asp Thr Val Asn Ala Lys
1               5                   10                  15

Pro Gly Asp Thr Val Arg Ile Pro Val Arg Phe Ser Gly Ile Pro Ser
            20                  25                  30

Lys Gly Ile Ala Asn Cys Asp Phe Val Tyr Ser Tyr Asp Pro Asn Val
        35                  40                  45

Leu Glu Ile Ile Glu Ile Lys Pro Gly Glu Leu Ile Val Asp Pro Asn

-continued

```
            50                  55                  60
Pro Asp Lys Ser Phe Asp Thr Ala Val Tyr Pro Asp Arg Lys Ile Ile
65                  70                  75                  80

Val Phe Leu Phe Ala Glu Asp Ser Gly Thr Gly Ala Tyr Ala Ile Thr
                    85                  90                  95

Lys Asp Gly Val Phe Ala Thr Ile Val Ala Lys Val Lys Ser Gly Ala
                100                 105                 110

Pro Asn Gly Leu Ser Val Ile Lys Phe Val Glu Val Gly Gly Phe Ala
                115                 120                 125

Asn Asn Asp Leu Val Glu Gln Lys Thr Gln Phe Phe Asp Gly Gly Val
130                 135                 140

Asn Val Gly Asp Thr Thr Glu Pro Ala Thr Pro Thr Thr Pro Val Thr
145                 150                 155                 160

Thr Pro Thr Thr Thr Asp Asp Leu Asp Ala Val Arg Ile Lys Val Asp
                165                 170                 175

Thr Val Asn Ala Lys Pro Gly Asp Thr Val Asn Ile Pro Val Arg Phe
                180                 185                 190

Ser Gly Ile Pro Ser Lys Gly Ile Ala Asn Cys Asp Phe Val Tyr Ser
                195                 200                 205

Tyr Asp Pro Asn Val Leu Glu Ile Ile Glu Ile Lys Pro Gly Glu Leu
210                 215                 220

Ile Val Asp Pro Asn Pro Thr Lys Ser Phe Asp Thr Ala Val Tyr Pro
225                 230                 235                 240

Asp Arg Lys Met Ile Val Phe Leu Phe Ala Glu Asp Ser Gly Thr Gly
                245                 250                 255

Ala Tyr Ala Ile Thr Lys Asp Gly Val Phe Ala Thr Ile Val Ala Lys
                260                 265                 270

Val Lys Glu Gly Ala Pro Asn Gly Leu Ser Val Ile Lys Phe Val Glu
                275                 280                 285

Val Gly Gly Phe Ala Asn Asn Asp Leu Val Glu Gln Lys Thr Gln Phe
                290                 295                 300

Phe Asp Gly Gly Val Asn Val Gly Asp Thr Thr Glu Pro Ala Thr Pro
305                 310                 315                 320

Thr Thr Pro Val Thr Thr Pro Thr Thr Thr Asp Asp Leu Asp Ala Leu
                325                 330                 335

Glu Ile Ile Pro Val Glu Glu Glu Asn Pro Asp Phe Trp Asn Arg Glu
                340                 345                 350

Ala Ala Glu Ala Leu Gly Ala Ala Lys Lys Leu Gln Pro Ala Gln Thr
                355                 360                 365

Ala Ala Lys Asn Leu Ile Ile Phe Leu Gly Asp Gly Met Gly Val Ser
                370                 375                 380

Thr Val Thr Ala Ala Arg Ile Leu Lys Gly Gln Lys Lys Asp Lys Leu
385                 390                 395                 400

Gly Pro Glu Leu Pro Leu Ala Met Asp Arg Phe Pro Tyr Val Ala Leu
                405                 410                 415

Ser Lys Thr Tyr Asn Val Asp Lys His Val Pro Asp Ser Gly Ala Thr
                420                 425                 430

Ala Thr Ala Tyr Leu Cys Gly Val Lys Gly Asn Phe Gln Thr Ile Gly
                435                 440                 445

Leu Ser Ala Ala Ala Arg Phe Asn Gln Cys Asn Thr Thr Arg Gly Asn
                450                 455                 460

Glu Val Ile Ser Val Met Asn Arg Ala Lys Lys Ala Gly Lys Ser Val
465                 470                 475                 480
```

```
Gly Val Val Thr Thr Thr Arg Val Gln His Ala Ser Pro Ala Gly Thr
                485                 490                 495

Tyr Ala His Thr Val Asn Arg Asn Trp Tyr Ser Asp Ala Asp Val Pro
            500                 505                 510

Ala Ser Ala Arg Gln Glu Gly Cys Gln Asp Ile Ala Thr Gln Leu Ile
            515                 520                 525

Ser Asn Met Asp Ile Asp Val Ile Leu Gly Gly Arg Lys Tyr Met
        530                 535                 540

Phe Arg Met Gly Thr Pro Asp Pro Glu Tyr Pro Asp Tyr Ser Gln
545                 550                 555                 560

Gly Gly Thr Arg Leu Asp Gly Lys Asn Leu Val Gln Glu Trp Leu Ala
            565                 570                 575

Lys Arg Gln Gly Ala Arg Tyr Val Trp Asn Arg Thr Glu Leu Met Gln
            580                 585                 590

Ala Ser Leu Asp Pro Ser Val Thr His Leu Met Gly Leu Phe Glu Pro
            595                 600                 605

Gly Asp Met Lys Tyr Glu Ile His Arg Asp Ser Thr Leu Asp Pro Ser
            610                 615                 620

Leu Met Glu Met Thr Glu Ala Ala Leu Arg Leu Leu Ser Arg Asn Pro
625                 630                 635                 640

Arg Gly Phe Phe Leu Phe Val Glu Gly Gly Arg Ile Asp His Gly His
            645                 650                 655

His Glu Ser Arg Ala Tyr Arg Ala Leu Thr Glu Thr Ile Met Phe Asp
            660                 665                 670

Asp Ala Ile Glu Arg Ala Gly Gln Leu Thr Ser Glu Glu Asp Thr Leu
            675                 680                 685

Ser Leu Val Thr Ala Asp His Ser His Val Phe Ser Phe Gly Gly Tyr
            690                 695                 700

Pro Leu Arg Gly Ser Ser Ile Phe Gly Leu Ala Pro Gly Lys Ala Arg
705                 710                 715                 720

Asp Arg Lys Ala Tyr Thr Val Leu Leu Tyr Gly Asn Gly Pro Gly Tyr
            725                 730                 735

Val Leu Lys Asp Gly Ala Arg Pro Asp Val Thr Glu Ser Glu Ser Gly
            740                 745                 750

Ser Pro Glu Tyr Arg Gln Gln Ser Ala Val Pro Leu Asp Glu Glu Thr
            755                 760                 765

His Ala Gly Glu Asp Val Ala Val Phe Ala Arg Gly Pro Gln Ala His
            770                 775                 780

Leu Val His Gly Val Gln Glu Gln Thr Phe Ile Ala His Val Met Ala
785                 790                 795                 800

Phe Ala Ala Cys Leu Glu Pro Tyr Thr Ala Cys Asp Leu Ala Pro Pro
            805                 810                 815

Ala Gly Thr Thr His His His His His His
            820                 825

<210> SEQ ID NO 18
<211> LENGTH: 1326
<212> TYPE: DNA
<213> ORGANISM: Artificial
<220> FEATURE:
<223> OTHER INFORMATION: Chemically synthesized oligonucleotide

<400> SEQUENCE: 18
atggatccca aaggatccct ttcctggaga atacttctgt ttctctccct ggcttttgag    60
```

-continued

| | |
|---|---|
| ttgagctacg gactcgacga tctggatgca gtaaggatta aagtggacac agtaaatgca | 120 |
| aaaccgggag acacagtaag aatacctgta agattcagcg gtataccatc caagggaata | 180 |
| gcaaactgtg actttgtata cagctatgac ccgaatgtac ttgagataat agagatagaa | 240 |
| ccgggagaca taatagttga cccgaatcct gacaagagct tgatactgc agtatatcct | 300 |
| gacagaaaga taatagtatt cctgtttgca gaagacagcg gaacaggagc gtatgcaata | 360 |
| actaaagacg gagtatttgc tacgatagta gcgaaagtaa agaaggagc acctaacgga | 420 |
| ctcagtgtaa tcaaatttgt agaagtaggc ggatttgcga acaatgacct tgtagaacag | 480 |
| aagacacagt tctttgacgg tggagtaaat gttggagata caacagaacc tgcaacacct | 540 |
| acaacacctg taacaacacc gacaacaaca gatgatctgg atgcactcga ggcgcccctc | 600 |
| atcctgtctc ggattgtggg aggctgggag tgcgagaagc attcccaacc ctggcaggtg | 660 |
| cttgtggcct ctcgtggcag ggcagtctgc ggcggtgttc tggtgcaccc ccagtgggtc | 720 |
| ctcacagctg cccactgcat caggaacaaa agcgtgatct tgctgggtcg gcacagcctg | 780 |
| tttcatcctg aagacacagg ccaggtattt caggtcagcc acagcttccc acaccgctc | 840 |
| tacgatatga gcctcctgaa gaatcgattc ctcaggccag tgatgactc cagccacgac | 900 |
| ctcatgctgc tccgcctgtc agagcctgcc gagctcacgg atgctgtgaa ggtcatggac | 960 |
| ctgcccaccc aggagccagc actggggacc acctgctacg cctcaggctg ggcagcatt | 1020 |
| gaaccagagg agttcttgac cccaaagaaa cttcagtgtg tggacctcca tgttatttcc | 1080 |
| aatgacgtgt gcgcgcaagt tcaccctcag aaggtgacca agttcatgct gtgtgctgga | 1140 |
| cgctggacag ggggcaaaag cacctgctcg ggtgattctg ggggcccact tgtctgtaat | 1200 |
| ggtgtgcttc aaggtatcac gtcatggggc agtgaaccat gtgccctgcc cgaaaggcct | 1260 |
| tccctgtaca ccaaggtggt gcattaccgg aagtggatca aggacaccat cgtggccaac | 1320 |
| ccctga | 1326 |

<210> SEQ ID NO 19
<211> LENGTH: 417
<212> TYPE: PRT
<213> ORGANISM: Artificial
<220> FEATURE:
<223> OTHER INFORMATION: Chemically synthesized peptide

<400> SEQUENCE: 19

```
Leu Asp Asp Leu Asp Ala Val Arg Ile Lys Val Asp Thr Val Asn Ala
1               5                   10                  15

Lys Pro Gly Asp Thr Val Arg Ile Pro Val Arg Phe Ser Gly Ile Pro
                20                  25                  30

Ser Lys Gly Ile Ala Asn Cys Asp Phe Val Tyr Ser Tyr Asp Pro Asn
            35                  40                  45

Val Leu Glu Ile Ile Glu Ile Glu Pro Gly Glu Leu Ile Val Asp Pro
        50                  55                  60

Asn Pro Thr Lys Ser Phe Asp Thr Ala Val Tyr Pro Asp Arg Lys Met
65                  70                  75                  80

Ile Val Phe Leu Phe Ala Glu Asp Ser Gly Thr Gly Ala Tyr Ala Ile
                85                  90                  95

Thr Glu Asp Gly Val Phe Ala Thr Ile Val Ala Lys Val Lys Ser Gly
                100                 105                 110

Ala Pro Asn Gly Leu Ser Val Ile Lys Phe Val Glu Val Gly Gly Phe
            115                 120                 125

Ala Asn Asn Asp Leu Val Glu Gln Lys Thr Gln Phe Phe Asp Gly Gly
```

```
              130                 135                 140
Val Asn Val Gly Asp Thr Thr Glu Pro Ala Thr Pro Thr Thr Pro Val
145                 150                 155                 160

Thr Thr Pro Thr Thr Thr Asp Asp Leu Asp Ala Leu Glu Ala Pro Leu
                165                 170                 175

Ile Leu Ser Arg Ile Val Gly Gly Trp Glu Cys Glu Lys His Ser Gln
            180                 185                 190

Pro Trp Gln Val Leu Val Ala Ser Arg Gly Arg Ala Val Cys Gly Gly
        195                 200                 205

Val Leu Val His Pro Gln Trp Val Leu Thr Ala Ala His Cys Ile Arg
210                 215                 220

Asn Lys Ser Val Ile Leu Leu Gly Arg His Ser Leu Phe His Pro Glu
225                 230                 235                 240

Asp Thr Gly Gln Val Phe Gln Val Ser His Ser Phe Pro His Pro Leu
                245                 250                 255

Tyr Asp Met Ser Leu Leu Lys Asn Arg Phe Leu Arg Pro Gly Asp Asp
            260                 265                 270

Ser Ser His Asp Leu Met Leu Leu Arg Leu Ser Glu Pro Ala Glu Leu
        275                 280                 285

Thr Asp Ala Val Lys Val Met Asp Leu Pro Thr Gln Glu Pro Ala Leu
290                 295                 300

Gly Thr Thr Cys Tyr Ala Ser Gly Trp Gly Ser Ile Glu Pro Glu Glu
305                 310                 315                 320

Phe Leu Thr Pro Lys Lys Leu Gln Cys Val Asp Leu His Val Ile Ser
                325                 330                 335

Asn Asp Val Cys Ala Gln Val His Pro Gln Lys Val Thr Lys Phe Met
            340                 345                 350

Leu Cys Ala Gly Arg Trp Thr Gly Gly Lys Ser Thr Cys Ser Gly Asp
        355                 360                 365

Ser Gly Gly Pro Leu Val Cys Asn Gly Val Leu Gln Gly Ile Thr Ser
    370                 375                 380

Trp Gly Ser Glu Pro Cys Ala Leu Pro Glu Arg Pro Ser Leu Tyr Thr
385                 390                 395                 400

Lys Val Val His Tyr Arg Lys Trp Ile Lys Asp Thr Ile Val Ala Asn
                405                 410                 415

Pro

<210> SEQ ID NO 20
<211> LENGTH: 1554
<212> TYPE: DNA
<213> ORGANISM: Artificial
<220> FEATURE:
<223> OTHER INFORMATION: Chemically synthesized oligonucleotide

<400> SEQUENCE: 20
atggatccca aaggatccct ttcctggaga atacttctgt ttctctccct ggcttttgag      60
ttgagctacg gactcgacga tctggatgca gtaaggatta agtggacac  agtaaatgca     120 aaaccgggag acacagtaag aataccctgta agattcagcg gtataccatc caagggaata    180
gcaaactgtg actttgtata cagctatgac ccgaatgtac ttgagataat agagatagaa    240
ccgggagaca taatagttga cccgaatcct gacaagagct tgatactgc  agtatatcct    300 gacagaaaga taatagtatt cctgtttgca gaagacagcg gaacaggagc gtatgcaata    360
actaaagacg gagtatttgc tacgatagta gcgaaagtaa aagaaggagc acctaacgga    420
```

```
ctcagtgtaa tcaaatttgt agaagtaggc ggatttgcga acaatgacct tgtagaacag     480
aagacacagt tctttgacgg tggagtaaat gttggagata caacagaacc tgcaacacct     540
acaacacctg taacaacacc gacaacaaca gatgatctgg atgcactcga ggatcagatt     600
tgcattggtt accatgcaaa caactcgaca gagcaggttg acacaataat ggaaaagaac     660
gttactgtta cacatgccca agacatactg gaaaagaaac acaacgggaa gctctgcgat     720
ctagatggag tgaagcctct aattttgaga gattgtagcg tagctggatg gctcctcgga     780
aacccaatgt gtgacgaatt catcaatgtg ccggaatggt cttacatagt ggagaaggcc     840
aatccagtca atgacctctg ttacccaggg gatttcaatg actatgaaaa attgaaacac     900
ctattgagca gaataaacca ttttgagaaa attcagatca tccccaaaag ttcttggtcc     960
agtcatgaag cctcattagg ggtgagctca gcatgtccat accagggaaa gtcctccttt    1020
ttcagaaatg tggtatggct tatcaaaaag aacagtacat acccaacaat aaagaggagc    1080
tacaataata ccaaccaaga agatcttttg gtactgtggg ggattcacca tcctaatgat    1140
gcggcagagc agacaaagct ctatcaaaac ccaaccacct atatttccgt tgggacatca    1200
acactaaacc agagattggt accaagaata gctactagat ccaaagtaaa cgggcaaagt    1260
ggaaggatgg agttcttctg gacaatttta aagccgaatg atgcaatcaa cttcgagagt    1320
aatgaaaatt tcattgctcc agaatatgca tacaaaattg tcaagaaagg ggactcaaca    1380
attatgaaaa gtgaattgga atatggtaac tgcaacacca gtgtcaaac tccaatgggg    1440 gcgataaact ctagcatgcc attccacaat atacaccctc tcaccattgg ggaatgcccc    1500
aaatatgtga atcaaacag attagtcctt gcgcaccatc accatcacca ttga           1554

<210> SEQ ID NO 21
<211> LENGTH: 493
<212> TYPE: PRT
<213> ORGANISM: Artificial
<220> FEATURE:
<223> OTHER INFORMATION: Chemically synthesized peptide

<400> SEQUENCE: 21

Leu Asp Asp Leu Asp Ala Val Arg Ile Lys Val Asp Thr Val Asn Ala
1               5                   10                  15

Lys Pro Gly Asp Thr Val Arg Ile Pro Val Arg Phe Ser Gly Ile Pro
            20                  25                  30

Ser Lys Gly Ile Ala Asn Cys Asp Phe Val Tyr Ser Tyr Asp Pro Asn
        35                  40                  45

Val Leu Glu Ile Ile Glu Ile Glu Pro Gly Glu Leu Ile Val Asp Pro
    50                  55                  60

Asn Pro Thr Lys Ser Phe Asp Thr Ala Val Tyr Pro Asp Arg Lys Met
65                  70                  75                  80

Ile Val Phe Leu Phe Ala Glu Asp Ser Gly Thr Gly Ala Tyr Ala Ile
                85                  90                  95

Thr Glu Asp Gly Val Phe Ala Thr Ile Val Ala Lys Val Lys Ser Gly
            100                 105                 110

Ala Pro Asn Gly Leu Ser Val Ile Lys Phe Val Glu Val Gly Gly Phe
        115                 120                 125

Ala Asn Asn Asp Leu Val Glu Gln Lys Thr Gln Phe Phe Asp Gly Gly
    130                 135                 140

Val Asn Val Gly Asp Thr Thr Glu Pro Ala Thr Pro Thr Thr Pro Val
145                 150                 155                 160

Thr Thr Pro Thr Thr Thr Asp Asp Leu Asp Ala Leu Glu Asp Gln Ile
```

```
          165                 170                 175
Cys Ile Gly Tyr His Ala Asn Asn Ser Thr Glu Gln Val Asp Thr Ile
                180                 185                 190
Met Glu Lys Asn Val Thr Val Thr His Ala Gln Asp Ile Leu Glu Lys
            195                 200                 205
Lys His Asn Gly Lys Leu Cys Asp Leu Asp Gly Val Lys Pro Leu Ile
        210                 215                 220
Leu Arg Asp Cys Ser Val Ala Gly Trp Leu Leu Gly Asn Pro Met Cys
225                 230                 235                 240
Asp Glu Phe Ile Asn Val Pro Glu Trp Ser Tyr Ile Val Glu Lys Ala
                245                 250                 255
Asn Pro Val Asn Asp Leu Cys Tyr Pro Gly Asp Phe Asn Asp Tyr Glu
            260                 265                 270
Lys Leu Lys His Leu Leu Ser Arg Ile Asn His Phe Glu Lys Ile Gln
        275                 280                 285
Ile Ile Pro Lys Ser Ser Trp Ser Ser His Glu Ala Ser Leu Gly Val
290                 295                 300
Ser Ser Ala Cys Pro Tyr Gln Gly Lys Ser Ser Phe Phe Arg Asn Val
305                 310                 315                 320
Val Trp Leu Ile Lys Lys Asn Ser Thr Tyr Pro Thr Ile Lys Arg Ser
                325                 330                 335
Tyr Asn Asn Thr Asn Gln Glu Asp Leu Leu Val Leu Trp Gly Ile His
            340                 345                 350
His Pro Asn Asp Ala Ala Glu Gln Thr Lys Leu Tyr Gln Asn Pro Thr
        355                 360                 365
Thr Tyr Ile Ser Val Gly Thr Ser Thr Leu Asn Gln Arg Leu Val Pro
    370                 375                 380
Arg Ile Ala Thr Arg Ser Lys Val Asn Gly Gln Ser Gly Arg Met Glu
385                 390                 395                 400
Phe Phe Trp Thr Ile Leu Lys Pro Asn Asp Ala Ile Asn Phe Glu Ser
                405                 410                 415
Asn Gly Asn Phe Ile Ala Pro Glu Tyr Ala Tyr Lys Ile Val Lys Lys
            420                 425                 430
Gly Asp Ser Thr Ile Met Lys Ser Glu Leu Glu Tyr Gly Asn Cys Asn
        435                 440                 445
Thr Lys Cys Gln Thr Pro Met Gly Ala Ile Asn Ser Ser Met Pro Phe
    450                 455                 460
His Asn Ile His Pro Leu Thr Ile Gly Glu Cys Pro Lys Tyr Val Lys
465                 470                 475                 480
Ser Asn Arg Leu Val Leu Ala His His His His His
                485                 490

<210> SEQ ID NO 22
<211> LENGTH: 1293
<212> TYPE: DNA
<213> ORGANISM: Artificial
<220> FEATURE:
<223> OTHER INFORMATION: Chemically synthesized oligonucleotide

<400> SEQUENCE: 22
atggatctgg atgcagtaag gattaaagtg gacacagtaa atgcaaaacc gggagacaca      60
gtaaatatac ctgtaagatt cagtggtata ccatccaagg gaatagcaaa ctgtgacttt     120
gtatacagct atgacccgaa tgtacttgag ataatagaga taaaaccggg agaattgata     180
gttgacccga atcctaccaa gagctttgat actgcagtat atcctgacag aaagatgata     240
```

-continued

```
gtattcctgt tgcggaaga cagcggaaca ggagcgtatg caataactaa agacggagta      300
tttgctacga tagtagcgaa agtaaaagaa ggagcaccta acgggctcag tgtaatcaaa      360
tttgtagaag taggcggatt tgcgaacaat gaccttgtag aacagaagac acagttcttt      420
gacggtggag taaatgttgg agatacaaca gaacctgcaa cacctacaac acctgtaaca      480
acaccgacaa caacagatga tctggatgca gctagccttc taaccgaggt cgaaacgtac      540
gttctctcta tcatcccgtc aggcccctc aaagccgaga tcgcacagag acttgaagat      600
gtctttgcag ggaagaacac cgatcttgag gttctcatgg aatggctaaa gacaagacca      660
atcctgtcac ctctgactaa ggggatttta ggatttgtgt tcacgctcac cgtgcccagt      720
gagcggggac tgcagcgtag acgctttgtc caaaatgctc ttaatgggaa cggagatcca      780
aataacatgg acaaagcagt taaactgtat aggaagctta agagggagat aacattccat      840
ggggccaaag aaatagcact cagttattct gctggtgcac ttgccagttg tatgggcctc      900
atatacaaca ggatggggc tgtgaccact gaagtggcat ttggcctggt atgcgcaacc      960
tgtgaacaga ttgctgactc ccagcatcgg tctcataggc aaatggtgac aacaaccaat     1020
ccactaatca gacatgagaa cagaatggtt ctagccagca ctacagctaa ggctatggag     1080
caaatggctg gatcgagtga gcaagcagca gaggccatgg atattgctag tcaggccagg     1140
caaatggtgc aggcgatgag aaccattggg actcatccta gctccagtgc tggtctaaaa     1200
gatgatcttc ttgaaaattt gcaggcttac cagaaacgga tgggggtgca gatgcagcga     1260
ttcaagctcg agcaccacca ccaccaccac tga                                  1293
```

<210> SEQ ID NO 23
<211> LENGTH: 430
<212> TYPE: PRT
<213> ORGANISM: Artificial
<220> FEATURE:
<223> OTHER INFORMATION: Chemically synthesized peptide

<400> SEQUENCE: 23

```
Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
        35                  40                  45

Leu Glu Ile Ile Glu Ile Lys Pro Gly Glu Leu Ile Val Asp Pro Asn
    50                  55                  60

Pro Thr Lys Ser Phe Asp Thr Ala Val Tyr Pro Asp Arg Lys Met Ile
65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
            100                 105                 110

Pro Asn Gly Leu Ser Val Ile Lys Phe Val Glu Val Gly Gly Phe Ala
        115                 120                 125

Asn Asn Asp Leu Val Glu Gln Lys Thr Gln Phe Phe Asp Gly Gly Val
    130                 135                 140

Asn Val Gly Asp Thr Thr Glu Pro Ala Thr Pro Thr Pro Val Thr
145                 150                 155                 160

Thr Pro Thr Thr Thr Asp Asp Leu Asp Ala Ala Ser Leu Leu Thr Glu
                165                 170                 175
```

```
Val Glu Thr Tyr Val Leu Ser Ile Ile Pro Ser Gly Pro Leu Lys Ala
            180                 185                 190

Glu Ile Ala Gln Arg Leu Glu Asp Val Phe Ala Gly Lys Asn Thr Asp
        195                 200                 205

Leu Glu Val Leu Met Glu Trp Leu Lys Thr Arg Pro Ile Leu Ser Pro
    210                 215                 220

Leu Thr Lys Gly Ile Leu Gly Phe Val Phe Thr Leu Thr Val Pro Ser
225                 230                 235                 240

Glu Arg Gly Leu Gln Arg Arg Phe Val Gln Asn Ala Leu Asn Gly
                245                 250                 255

Asn Gly Asp Pro Asn Asn Met Asp Lys Ala Val Lys Leu Tyr Arg Lys
            260                 265                 270

Leu Lys Arg Glu Ile Thr Phe His Gly Ala Lys Glu Ile Ala Leu Ser
        275                 280                 285

Tyr Ser Ala Gly Ala Leu Ala Ser Cys Met Gly Leu Ile Tyr Asn Arg
    290                 295                 300

Met Gly Ala Val Thr Thr Glu Val Ala Phe Gly Leu Val Cys Ala Thr
305                 310                 315                 320

Cys Glu Gln Ile Ala Asp Ser Gln His Arg Ser His Arg Gln Met Val
                325                 330                 335

Thr Thr Thr Asn Pro Leu Ile Arg His Glu Asn Arg Met Val Leu Ala
            340                 345                 350

Ser Thr Thr Ala Lys Ala Met Glu Gln Met Ala Gly Ser Ser Glu Gln
        355                 360                 365

Ala Ala Glu Ala Met Asp Ile Ala Ser Gln Ala Arg Gln Met Val Gln
    370                 375                 380

Ala Met Arg Thr Ile Gly Thr His Pro Ser Ser Ser Ala Gly Leu Lys
385                 390                 395                 400

Asp Asp Leu Leu Glu Asn Leu Gln Ala Tyr Gln Lys Arg Met Gly Val
                405                 410                 415

Gln Met Gln Arg Phe Lys Leu Glu His His His His His
            420                 425                 430

<210> SEQ ID NO 24
<211> LENGTH: 9
<212> TYPE: PRT
<213> ORGANISM: Artificial
<220> FEATURE:
<223> OTHER INFORMATION: Chemically synthesized peptide

<400> SEQUENCE: 24

Gly Ile Leu Gly Phe Val Phe Thr Leu
1               5

<210> SEQ ID NO 25
<211> LENGTH: 661
<212> TYPE: PRT
<213> ORGANISM: Artificial
<220> FEATURE:
<223> OTHER INFORMATION: Chemically synthesized peptide

<400> SEQUENCE: 25

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
```

```
                35                  40                  45
Tyr Pro Glu Trp Thr Glu Ala Gln Arg Leu Asp Cys Trp Arg Gly Gly
 50                  55                  60

Gln Val Ser Leu Lys Val Ser Asn Asp Gly Pro Thr Leu Ile Gly Ala
 65                  70                  75                  80

Asn Ala Ser Phe Ser Ile Ala Leu Asn Phe Pro Gly Ser Gln Lys Val
                 85                  90                  95

Leu Pro Asp Gly Gln Val Ile Trp Val Asn Asn Thr Ile Ile Asn Gly
                100                 105                 110

Ser Gln Val Trp Gly Gln Pro Val Tyr Pro Gln Glu Thr Asp Asp
            115                 120                 125

Ala Cys Ile Phe Pro Asp Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ala Phe Thr
                195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
            435                 440                 445

Ser Ile Thr Gly Ser Leu Gly Pro Leu Leu Asp Gly Thr Ala Thr Leu
    450                 455                 460
```

```
Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
            485                 490                 495

Glu Ile Leu Gln Ala Val Pro Ser Gly Gly Asp Ala Phe Glu Leu
        500                 505                 510

Thr Val Ser Cys Gln Gly Gly Leu Pro Lys Glu Ala Cys Met Glu Ile
            515                 520                 525

Ser Ser Pro Gly Cys Gln Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
            565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 26
<211> LENGTH: 9
<212> TYPE: PRT
<213> ORGANISM: Artificial
<220> FEATURE:
<223> OTHER INFORMATION: Chemically synthesized peptide

<400> SEQUENCE: 26

Lys Thr Trp Gly Gln Tyr Trp Gln Val
1               5

<210> SEQ ID NO 27
<211> LENGTH: 9
<212> TYPE: PRT
<213> ORGANISM: Artificial
<220> FEATURE:
<223> OTHER INFORMATION: Chemically synthesized peptide

<400> SEQUENCE: 27

Ile Met Asp Gln Val Pro Phe Ser Val
1               5

<210> SEQ ID NO 28
<211> LENGTH: 9
<212> TYPE: PRT
<213> ORGANISM: Artificial
<220> FEATURE:
<223> OTHER INFORMATION: Chemically synthesized peptide

<400> SEQUENCE: 28

Ile Thr Asp Gln Val Pro Phe Ser Val
1               5
```

```
<210> SEQ ID NO 29
<211> LENGTH: 9
<212> TYPE: PRT
<213> ORGANISM: Artificial
<220> FEATURE:
<223> OTHER INFORMATION: Chemically synthesized peptide

<400> SEQUENCE: 29

Tyr Leu Glu Pro Gly Pro Val Thr Val
1               5

<210> SEQ ID NO 30
<211> LENGTH: 9
<212> TYPE: PRT
<213> ORGANISM: Artificial
<220> FEATURE:
<223> OTHER INFORMATION: Chemically synthesized peptide

<400> SEQUENCE: 30

Tyr Leu Glu Pro Gly Pro Val Thr Ala
1               5

<210> SEQ ID NO 31
<211> LENGTH: 204
<212> TYPE: PRT
<213> ORGANISM: Artificial
<220> FEATURE:
<223> OTHER INFORMATION: Chemically synthesized peptide

<400> SEQUENCE: 31

Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
        35                  40                  45

Leu Glu Ile Ile Glu Ile Lys Pro Gly Glu Leu Ile Val Asp Pro Asn
    50                  55                  60

Pro Thr Lys Ser Phe Asp Thr Ala Val Tyr Pro Asp Arg Lys Met Ile
65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
            100                 105                 110

Pro Asn Gly Leu Ser Val Ile Lys Phe Val Glu Val Gly Gly Phe Ala
        115                 120                 125

Asn Asn Asp Leu Val Glu Gln Lys Thr Gln Phe Phe Asp Gly Gly Val
    130                 135                 140

Asn Val Gly Asp Thr Thr Glu Pro Ala Thr Pro Thr Thr Pro Val Thr
145                 150                 155                 160

Thr Pro Thr Thr Thr Asp Asp Leu Asp Ala Ala Arg Ser Ala Phe Thr
                165                 170                 175

Ile Met Asp Gln Val Pro Phe Ser Ser Val Ser Val Ser Ala Ser Arg Lys
            180                 185                 190

Gly Ala Ala Ala Leu Glu His His His His His His
        195                 200

<210> SEQ ID NO 32
<211> LENGTH: 118
<212> TYPE: PRT
```

```
<213> ORGANISM: Artificial
<220> FEATURE:
<223> OTHER INFORMATION: Chemically synthesized peptide

<400> SEQUENCE: 32

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 33
<211> LENGTH: 9
<212> TYPE: PRT
<213> ORGANISM: Artificial
<220> FEATURE:
<223> OTHER INFORMATION: Chemically synthesized peptide

<400> SEQUENCE: 33

Ala Ala Gly Ile Gly Ile Leu Thr Val
1               5

<210> SEQ ID NO 34
<211> LENGTH: 10
<212> TYPE: PRT
<213> ORGANISM: Artificial
<220> FEATURE:
<223> OTHER INFORMATION: Chemically synthesized peptide

<400> SEQUENCE: 34

Glu Ala Ala Gly Ile Gly Ile Leu Thr Val
1               5                   10

<210> SEQ ID NO 35
<211> LENGTH: 10
<212> TYPE: PRT
<213> ORGANISM: Artificial
<220> FEATURE:
<223> OTHER INFORMATION: Chemically synthesized peptide

<400> SEQUENCE: 35

Glu Leu Ala Gly Ile Gly Ile Leu Thr Val
1               5                   10

<210> SEQ ID NO 36
<211> LENGTH: 204
<212> TYPE: PRT
<213> ORGANISM: Artificial
<220> FEATURE:
<223> OTHER INFORMATION: Chemically synthesized peptide

<400> SEQUENCE: 36
```

```
Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
                35                  40                  45

Leu Glu Ile Ile Glu Ile Lys Pro Gly Glu Leu Ile Val Asp Pro Asn
 50                  55                  60

Pro Thr Lys Ser Phe Asp Thr Ala Val Tyr Pro Asp Arg Lys Met Ile
 65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
                100                 105                 110

Pro Asn Gly Leu Ser Val Ile Lys Phe Val Glu Val Gly Gly Phe Ala
                115                 120                 125

Asn Asn Asp Leu Val Glu Gln Lys Thr Gln Phe Phe Asp Gly Gly Val
    130                 135                 140

Asn Val Gly Asp Thr Thr Glu Pro Ala Thr Pro Thr Thr Pro Val Thr
145                 150                 155                 160

Thr Pro Thr Thr Thr Asp Asp Leu Asp Ala Ala Arg Thr Ala Glu Glu
                165                 170                 175

Leu Ala Gly Ile Gly Ile Leu Thr Val Ile Leu Gly Ala Ser Arg Lys
                180                 185                 190

Gly Ala Ala Ala Leu Glu His His His His His
                195                 200
```

<210> SEQ ID NO 37
<211> LENGTH: 241
<212> TYPE: PRT
<213> ORGANISM: Artificial
<220> FEATURE:
<223> OTHER INFORMATION: Chemically synthesized peptide

<400> SEQUENCE: 37

```
Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
                35                  40                  45

Leu Glu Ile Ile Glu Ile Lys Pro Gly Glu Leu Ile Val Asp Pro Asn
 50                  55                  60

Pro Thr Lys Ser Phe Asp Thr Ala Val Tyr Pro Asp Arg Lys Met Ile
 65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
                100                 105                 110

Pro Asn Gly Leu Ser Val Ile Lys Phe Val Glu Val Gly Gly Phe Ala
                115                 120                 125

Asn Asn Asp Leu Val Glu Gln Lys Thr Gln Phe Phe Asp Gly Gly Val
    130                 135                 140

Asn Val Gly Asp Thr Thr Glu Pro Ala Thr Pro Thr Thr Pro Val Thr
145                 150                 155                 160
```

Thr Pro Thr Thr Thr Asp Asp Leu Asp Ala Ala Ser Asp Thr Thr Glu
            165                 170                 175

Ala Arg His Pro His Pro Pro Val Thr Thr Pro Thr Thr Asp Arg Lys
            180                 185                 190

Gly Thr Thr Ala Glu Glu Leu Ala Gly Ile Gly Ile Leu Thr Val Ile
            195                 200                 205

Leu Gly Gly Lys Arg Thr Asn Asn Ser Thr Pro Thr Lys Gly Glu Phe
        210                 215                 220

Cys Arg Tyr Pro Ser His Trp Arg Pro Leu Glu His His His His
225                 230                 235                 240

His

<210> SEQ ID NO 38
<211> LENGTH: 66
<212> TYPE: PRT
<213> ORGANISM: Artificial
<220> FEATURE:
<223> OTHER INFORMATION: Chemically synthesized peptide

<400> SEQUENCE: 38

Ala Ser Asp Thr Thr Glu Ala Arg His Pro His Pro Pro Val Thr Thr
1               5                   10                  15

Pro Thr Thr Thr Asp Arg Lys Gly Thr Thr Ala Glu Glu Leu Ala Gly
            20                  25                  30

Ile Gly Ile Leu Thr Val Ile Leu Gly Gly Lys Arg Thr Asn Asn Ser
        35                  40                  45

Thr Pro Thr Lys Gly Glu Phe Cys Arg Tyr Pro Ser His Trp Arg Pro
    50                  55                  60

Arg Leu
65

<210> SEQ ID NO 39
<211> LENGTH: 57
<212> TYPE: DNA
<213> ORGANISM: Artificial
<220> FEATURE:
<223> OTHER INFORMATION: Chemically synthesized oligonucleotide

<400> SEQUENCE: 39
cacggtcacc gtctccaaag cttccggagc tagcgagggc ggcagcctgg ccgcgct                57

<210> SEQ ID NO 40
<211> LENGTH: 70
<212> TYPE: DNA
<213> ORGANISM: Artificial
<220> FEATURE:
<223> OTHER INFORMATION: Chemically synthesized oligonucleotide

<400> SEQUENCE: 40
ggccggctcc tgcgaaggga gccggccggt cgcggccgct tacttcaggt cctcgcgcgg        60
cggtttgccg                                                               70

<210> SEQ ID NO 41
<211> LENGTH: 518
<212> TYPE: PRT
<213> ORGANISM: Artificial
<220> FEATURE:
<223> OTHER INFORMATION: Chemically synthesized peptide

<400> SEQUENCE: 41

Met Asp Leu Asp Ala Val Arg Ile Lys Val Asp Thr Val Asn Ala Lys

-continued

```
1               5                   10                  15
Pro Gly Asp Thr Val Asn Ile Pro Val Arg Phe Ser Gly Ile Pro Ser
                20                  25                  30
Lys Gly Ile Ala Asn Cys Asp Phe Val Tyr Ser Tyr Asp Pro Asn Val
                35                  40                  45
Leu Glu Ile Ile Glu Ile Lys Pro Gly Glu Leu Ile Val Asp Pro Asn
                50                  55                  60
Pro Thr Lys Ser Phe Asp Thr Ala Val Tyr Pro Asp Arg Lys Met Ile
 65                 70                  75                  80
Val Phe Leu Phe Ala Glu Asp Ser Gly Thr Gly Ala Tyr Ala Ile Thr
                85                  90                  95
Lys Asp Gly Val Phe Ala Thr Ile Val Ala Lys Val Lys Glu Gly Ala
                100                 105                 110
Pro Asn Gly Leu Ser Val Ile Lys Phe Val Glu Val Gly Gly Phe Ala
                115                 120                 125
Asn Asn Asp Leu Val Glu Gln Lys Thr Gln Phe Phe Asp Gly Gly Val
                130                 135                 140
Asn Val Gly Asp Thr Thr Glu Pro Ala Thr Pro Thr Thr Pro Val Thr
145                 150                 155                 160
Thr Pro Thr Thr Thr Asp Asp Leu Asp Ala Ala Ser Glu Gly Gly Ser
                165                 170                 175
Leu Ala Ala Leu Thr Ala His Gln Ala Cys His Leu Pro Leu Glu Thr
                180                 185                 190
Phe Thr Arg His Arg Gln Pro Arg Gly Trp Glu Gln Leu Glu Gln Cys
                195                 200                 205
Gly Tyr Pro Val Gln Arg Leu Val Ala Leu Tyr Leu Ala Ala Arg Leu
                210                 215                 220
Ser Trp Asn Gln Val Asp Gln Val Ile Arg Asn Ala Leu Ala Ser Pro
225                 230                 235                 240
Gly Ser Gly Gly Asp Leu Gly Glu Ala Ile Arg Glu Gln Pro Glu Gln
                245                 250                 255
Ala Arg Leu Ala Leu Thr Leu Ala Ala Ala Glu Ser Glu Arg Phe Val
                260                 265                 270
Arg Gln Gly Thr Gly Asn Asp Glu Ala Gly Ala Ala Asn Gly Pro Ala
                275                 280                 285
Asp Ser Gly Asp Ala Leu Leu Glu Arg Asn Tyr Pro Thr Gly Ala Glu
                290                 295                 300
Phe Leu Gly Asp Gly Gly Asp Val Ser Phe Ser Thr Arg Gly Thr Gln
305                 310                 315                 320
Asn Trp Thr Val Glu Arg Leu Leu Gln Ala His Arg Gln Leu Glu Glu
                325                 330                 335
Arg Gly Tyr Val Phe Val Gly Tyr His Gly Thr Phe Leu Glu Ala Ala
                340                 345                 350
Gln Ser Ile Val Phe Gly Gly Val Arg Ala Arg Ser Gln Asp Leu Asp
                355                 360                 365
Ala Ile Trp Arg Gly Phe Tyr Ile Ala Gly Asp Pro Ala Leu Ala Tyr
                370                 375                 380
Gly Tyr Ala Gln Asp Gln Glu Pro Asp Ala Arg Gly Arg Ile Arg Asn
385                 390                 395                 400
Gly Ala Leu Leu Arg Val Tyr Val Pro Arg Ser Ser Leu Pro Gly Phe
                405                 410                 415
Tyr Arg Thr Ser Leu Thr Leu Ala Ala Pro Glu Ala Ala Gly Glu Val
                420                 425                 430
```

```
Glu Arg Leu Ile Gly His Pro Leu Pro Leu Arg Leu Asp Ala Ile Thr
            435                 440                 445

Gly Pro Glu Glu Glu Gly Gly Arg Leu Glu Thr Ile Leu Gly Trp Pro
        450                 455                 460

Leu Ala Glu Arg Thr Val Val Ile Pro Ser Ala Ile Pro Thr Asp Pro
465                 470                 475                 480

Arg Asn Val Gly Gly Asp Leu Asp Pro Ser Ser Ile Pro Asp Lys Glu
                485                 490                 495

Gln Ala Ile Ser Ala Leu Pro Asp Tyr Ala Ser Gln Pro Gly Lys Pro
            500                 505                 510

Pro Arg Glu Asp Leu Lys
            515

<210> SEQ ID NO 42
<211> LENGTH: 614
<212> TYPE: PRT
<213> ORGANISM: Artificial
<220> FEATURE:
<223> OTHER INFORMATION: Chemically synthesized peptide

<400> SEQUENCE: 42

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Ser Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Met Ala Thr Tyr Phe Cys
                85                  90                  95

Ala Arg Gly Asp Phe Arg Tyr Tyr Tyr Phe Asp Tyr Trp Gly Gln Gly
            100                 105                 110

Thr Thr Leu Thr Gly Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Thr Thr Glu Pro Ala Thr Pro Thr Thr Pro Val Thr Thr Pro Thr Thr
450                 455                 460

Thr Asp Asp Leu Asp Ala Val Arg Ile Lys Val Asp Thr Val Asn Ala
465                 470                 475                 480

Lys Pro Gly Asp Thr Val Asn Ile Pro Val Arg Phe Ser Gly Ile Pro
                485                 490                 495

Ser Lys Gly Ile Ala Asn Cys Asp Phe Val Tyr Ser Tyr Asp Pro Asn
            500                 505                 510

Val Leu Glu Ile Ile Glu Ile Lys Pro Gly Glu Leu Ile Val Asp Pro
        515                 520                 525

Asn Pro Thr Lys Ser Phe Asp Thr Ala Val Tyr Pro Asp Arg Lys Met
530                 535                 540

Ile Val Phe Leu Phe Ala Glu Asp Ser Gly Thr Gly Ala Tyr Ala Ile
545                 550                 555                 560

Thr Lys Asp Gly Val Phe Ala Thr Ile Val Ala Lys Val Lys Glu Gly
                565                 570                 575

Ala Pro Asn Gly Leu Ser Val Ile Lys Phe Val Glu Val Gly Gly Phe
            580                 585                 590

Ala Asn Asn Asp Leu Val Glu Gln Lys Thr Gln Phe Phe Asp Gly Gly
        595                 600                 605

Val Asn Val Gly Asp Thr
    610

<210> SEQ ID NO 43
<211> LENGTH: 308
<212> TYPE: PRT
<213> ORGANISM: Artificial
<220> FEATURE:
<223> OTHER INFORMATION: Chemically synthesized peptide

<400> SEQUENCE: 43

Leu Asp Asp Leu Asp Ala Val Arg Ile Lys Val Asp Thr Val Asn Ala
1               5                   10                  15
```

```
Lys Pro Gly Asp Thr Val Arg Ile Pro Val Arg Phe Ser Gly Ile Pro
             20                  25                  30

Ser Lys Gly Ile Ala Asn Cys Asp Phe Val Tyr Ser Tyr Asp Pro Asn
         35                  40                  45

Val Leu Glu Ile Ile Glu Ile Glu Pro Gly Asp Ile Ile Val Asp Pro
     50                  55                  60

Asn Pro Asp Lys Ser Phe Asp Thr Ala Val Tyr Pro Asp Arg Lys Ile
65              70                  75                  80

Ile Val Phe Leu Phe Ala Glu Asp Ser Gly Thr Gly Ala Tyr Ala Ile
             85                  90                  95

Thr Lys Asp Gly Val Phe Ala Thr Ile Val Ala Lys Val Lys Glu Gly
             100                 105                 110

Ala Pro Asn Gly Leu Ser Val Ile Lys Phe Val Glu Val Gly Gly Phe
             115                 120                 125

Ala Asn Asn Asp Leu Val Glu Gln Lys Thr Gln Phe Phe Asp Gly Gly
             130                 135                 140

Val Asn Val Gly Asp Thr Thr Glu Pro Ala Thr Pro Thr Thr Pro Val
145                 150                 155                 160

Thr Thr Pro Thr Thr Thr Asp Asp Leu Asp Ala Leu Glu Ala Asp Gln
             165                 170                 175

Gly Gln Asp Arg His Met Ile Arg Met Arg Gln Leu Ile Asp Ile Val
             180                 185                 190

Asp Gln Leu Lys Asn Tyr Val Asn Asp Leu Val Pro Glu Phe Leu Pro
             195                 200                 205

Ala Pro Glu Asp Val Glu Thr Asn Cys Glu Trp Ser Ala Phe Ser Cys
             210                 215                 220

Phe Gln Lys Ala Gln Leu Lys Ser Ala Asn Thr Gly Asn Asn Glu Arg
225                 230                 235                 240

Ile Ile Asn Val Ser Ile Lys Lys Leu Lys Arg Lys Pro Pro Ser Thr
             245                 250                 255

Asn Ala Gly Arg Arg Gln Lys His Arg Leu Thr Cys Pro Ser Cys Asp
             260                 265                 270

Ser Tyr Glu Lys Lys Pro Pro Lys Glu Phe Leu Glu Arg Phe Lys Ser
             275                 280                 285

Leu Leu Gln Lys Met Ile His Gln His Leu Ser Ser Arg Thr His Gly
             290                 295                 300

Ser Glu Asp Ser
305
```